(12) United States Patent
Dervan et al.

(10) Patent No.: US 6,559,125 B1
(45) Date of Patent: May 6, 2003

(54) POLYAMIDE-ALKYLATOR CONJUGATES AND RELATED PRODUCTS AND METHOD

(75) Inventors: Peter B. Dervan, San Marino, CA (US); Nicholas Wurtz, Pasadena, CA (US); Aileen Chang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/772,315

(22) Filed: Jan. 26, 2001

Related U.S. Application Data
(60) Provisional application No. 60/178,821, filed on Jan. 28, 2000.

(51) Int. Cl.[7] .................. A61K 38/00; A01N 43/04; C12Q 1/68; C07H 21/00
(52) U.S. Cl. ............... 514/12; 514/2; 514/44; 435/6; 536/23.1; 536/24.3; 536/25.3
(58) Field of Search .............. 435/6; 536/23.1, 536/24.3, 25.3; 514/2, 44, 12

(56) References Cited

U.S. PATENT DOCUMENTS

| | | | |
|---|---|---|---|
| 4,766,142 A | 8/1988 | Acramone et al. | 514/422 |
| 5,017,599 A | 5/1991 | Lazzari et al. | 514/422 |
| 5,049,579 A | 9/1991 | Lazzari et al. | 514/422 |
| 5,175,182 A | 12/1992 | Mongelli et al. | 514/428 |
| 5,273,991 A | 12/1993 | Lee | 514/397 |

(List continued on next page.)

FOREIGN PATENT DOCUMENTS

| | | |
|---|---|---|
| EP | 0 388 948 B1 | 12/1993 |
| JP | 11-171886 | 6/1999 |
| JP | 11-189594 | 7/1999 |
| WO | WO 94/20463 | 9/1994 |
| WO | WO 97/03957 | 2/1997 |

(List continued on next page.)

OTHER PUBLICATIONS

Iida et al. Yuki Gosei Kagaku Kyokaishi 2000, 58(10), pp. 975–987. abstract only.*
Bachelerie et al., "HIV Enhancer Activity Perpetuated by NF–kB Induction on Infection of Monocytes," Nature, vol. 350:709–712, 1991.
Chen et al., "Assembly of Recombinant TFIID Reveals Differential Coactivator Requirements for Distinct Transcriptional Activators," Cell, vol. 79:93–105, 1994.
Chen et al., "Design, Synthesis and Evaluation of Novel Bismustard Cross–Linked Lexitropsins," Bioorganic & Medicinal Chemistry Letters, vol. 5, No. 19: 2223–2228, 1995.
Ding et al., "Synthesis and Antiviral Activity of Three Pyrazole Analogues of Distamycin A," ACTA Chem. Scand., vol. 48: 498–505, 1994.

(List continued on next page.)

*Primary Examiner*—Jezia Riley
(74) *Attorney, Agent, or Firm*—Michael A. Whittaker; Foley & Lardner

(57) ABSTRACT

The present invention is based on the surprising and unexpected discovery of new and useful polyamide-alkylator conjugates. As a result of their DNA binding properties, polyamides deliver reactive moieties for covalent reaction at specific DNA sequences and thereby inhibit DNA-protein interactions. Thus, site specific alkylation of DNA is a useful tool to regulate gene expression. In addition to competing with transcription factors or promoters, the conjugates of the present invention will be used to target a gene's coding region. This will allow using synthetic chemistry to create a new class of gene specific "knockout" reagents which will be useful in biological disciplines.

31 Claims, 23 Drawing Sheets

U.S. PATENT DOCUMENTS

| | | | |
|---|---|---|---|
| 5,310,752 A | 5/1994 | Lazzari et al. | 514/422 |
| 5,502,068 A | 3/1996 | Lown et al. | 514/397 |
| 5,808,087 A | 9/1998 | Matsunaga et al. | 548/306.1 |
| 5,821,258 A | 10/1998 | Matsunaga et al. | 514/394 |
| 5,843,937 A | 12/1998 | Wang et al. | 514/202 |
| 5,852,011 A | 12/1998 | Matsunaga et al. | 514/228.2 |
| 5,998,140 A | 12/1999 | Dervan et al. | 435/6 |
| 6,090,947 A | 7/2000 | Dervan et al. | 548/312.4 |
| 6,143,901 A | 11/2000 | Dervan | 548/312.4 |
| 6,153,642 A | 11/2000 | Cozzi et al. | 514/414 |
| 6,165,980 A | 12/2000 | Cozzi et al. | 514/19 |
| 6,177,408 B1 | 6/2001 | Cozzi et al. | 514/17 |

FOREIGN PATENT DOCUMENTS

| | | |
|---|---|---|
| WO | WO 97/28123 | 8/1997 |
| WO | WO 97/30975 | 8/1997 |
| WO | WO 98/04524 | 2/1998 |
| WO | WO 98/21202 | 5/1998 |
| WO | WO 98/35702 | 8/1998 |
| WO | WO 98/37066 | 8/1998 |
| WO | WO 98/37067 | 8/1998 |
| WO | WO 98/37087 | 8/1998 |
| WO | WO 98/45284 | 10/1998 |
| WO | WO 98/49142 | 11/1998 |
| WO | WO 98/50058 | 11/1998 |
| WO | WO 98/50582 | 11/1998 |
| WO | WO 99/50265 | 10/1999 |
| WO | WO 99/50266 | 10/1999 |
| WO | WO 99/64413 | 12/1999 |

OTHER PUBLICATIONS

Duval–Valentin et al., "Specific Inhibition of Transcription by Triple Helix–Forming Oligoonucleotides," Proc. Natl. Acad. Sci., USA, vol. 89:504–508, 1992.

Gottesfeld et al., "Regulation of Gene Expression by Small Molecules," Nature, vol. 387:202–205, 1997.

Gupta et al., "Novel DNA–directed Alkylating Agents Consisting of Naphthalimide, Nitogen Mustard and Lexitropsin Moieties: Synthesis, DNA Sequence Specificity and Biological Evaluation," Anti–Cancer Drug Design, vol. 11: 581–596, 1996.

Herman et al., "Stereochemical Control of the DNA Binding Affinity, Sequence Specificity, and Orientation Preference of Chiral Hairpin Polyamides in the Minor Groove," J. Am. Chem. Soc., vol. 120:1382–1391, 1998.

Jones et al. "Control of RNA Initiation and Elongation at the HIV–1 Promoter," Annual Rev. Biochem., vol. 63:717–743, 1994.

Kim et al., "Replication of Type 1 Human Immunodeficiency Viruses Containing Linker Substitution Mutations in the ~201 to ~'30 region of the Long terminal Repeat," J. Virol, vol. 67:1658–1662, 1993.

Love et al., "Structural Basis for DNA Bending by the Architectural Transcription Factor LEF–1," Nature, vol. 376:791–795, 1995.

Maher et al., "Analysis of Promoter–Specific Repression by Triple–Helical DNA Complexes in a Eukaryotic Cell–Free Transcription System," Biochemistry, vol. 31:70–81, 1992.

Maldonado et al., "News on Initiation and Elongation of Transcription by RNA Polymerase II," Current Opinion in Cell Biology, vol. 7:352–361, 1995.

Milton et al., "Total Chemical Synthesis of a D–Enzyme: The Enantiomers of HIV–1 Protease Show Demonstration of Reciprocal Chiral Substrate Specificity," Science, vol. 256:1445–1448, 1992.

Moser et al., "Sequence Specific Cleavage of Double Helixal DNA by Triple Helix Formation," Science, vol. 238:645–650, 1987.

Perkins et al., "An Interaction Between the DNA–Binding Domains of RelA(p65) and Sp1 Mediates Human Immunodeficiency Virus Gene Activation," Mol. Cell. Biol., vol. 14:6570–6583, 1994.

Schnolzer et al., "In situ Neutralization in Boc–chemistry Solid Phase Peptide Synthesis," Intl. J. Peptide Protein Res., vol. 40:180–193, 1992.

Sheridan et al., "Activation of the HIV–1 Enhancer by the LEF–1 HMG Protein on Nucleosome–assembled DNA in Vitro," Genes & Dev., vol. 9:2090–2104, 1995.

Swalley et al., "Discrimination of 5'–GGGG–3', 5'GCGC–3', and 5'GGCC–3' Sequences in the Minor Groove of DNA by Eight–Ring Hairpin Polyamides," J. Am. Chem. Soc., vol. 119:6953–6991, 1997.

Swalley et al., "A Pyrrole–Imidazole Polyamide Motif for recognition of Eleven Base Pair Sequences in the Minor Groove of DNA," Chem–Eur. J., vol. 3:1600–1607, 1997.

Trauger et al., "Cooperative Hairpin Dimers for Recognition of DNA by Pyrrole–Imidazole Polyamides," Angewandte Chemie–International Edition, vol. 37:1421–1423, 1998.

Trauger et al., "Extension of Sequence–Specific Recognition in the Minor Groove of DNA by Pyrrole–Imidazole Polyamides to 9–13 Base Pairs," J. Am. Chem. Soc., vol. 118:6160–6166, 1996.

Trauger et al., "Recognition of 16 Base Pairs in the Minor Groove of DNA by a Pyrrole–Imidazole Polyamide Dimer," J. Am. Chem. Soc., vol. 120:3534–3535, 1998.

Trauger et al., "Recognition of DNA by Designed Ligands at Subnanomolar Conceentrations," Nature, vol. 382:559–561, 1996.

Turner et al., "Recognition of Seven Base Pair Sequences in the Minor Groove of DNA by Ten–Ring Pyrrole–Imidazole Polyamide Hairpins," J. Am. Chem. Soc., vol. 119:7636–7644, 1997.

Waterman et al., "Purification of TCF–1x, A T–Cell–Specific Transcription Factor That Activates the T–Cell receptor cX Gene Enhancer in a Context–Dependent Manner," New Biologist, vol. 2:621–636, 1990.

Arcamone et al, "Synthesis, DNA–Binding Properties and Antitumor Activity of Novel Distamycle Derivatives," J.Med.Chem., vol. 32:774–778, 1989.

Baird et al., "Solid Phase Synthesis of Polyamides Containing Imidazole and Pyrrole Amino Acids," J. Am. Chem. Soc., vol. 118:6141–6146, 1996.

Baraldi et al., "Heterocyclic Analogs of DNA Minor groove Alkylating Agents," Current Pharmaceutical Design, vol. 4:249–276, 1998.

Baraldi et al., "Structure–Activity Relationship of Novel Tallimustine Derivatives: Synthesis and Antitumor Activity," Biorganic and Medicinal Chemistry Letters, vol. 6, No. 11:1247–1252, 1996.

Berna et al, "Tallimustine, an Effective Antileukemic Agent in a Severe Combined Immunodeficient Mouse Model of Adult Myelogenous Leukemia, Induces Remissions in a Phase I Study," Clinical Cancer Research, vol. 3:2377–2384, 1997.

Boger et al., "1,2,9,9a–Tetrahydrocyclopropra[c]benz[e] indol–4–one (CBI) Analogs of CC–1065 and the Duocarmycins: Synthesis and Evaluation," Bioorganic and Medicinal Chemistry, vol. 3, No. 11:1429–1453, 1995.

Boger et al., "An Efficient Synthesis of 1,2,9,9a–Tetrahydrocyclopropra[c]benz[e]indol–4–one (CBI): An enhanced and Simplified Analog of the CCD–1065 and Duocarmycin Alkylation Subunite," J.Org.Chem, vol. 60: 1271–1275, 1995.

Boger et al., "An Efficient Synthesis of 1,2,9,9a–Tetrahydrocyclopropra[c]benz[e]indol–4–one (CBI): A Simplified Analogue of the CC–1065 Alkylation Subunit," J.Org.Chem, vol. 57: 2873–2876, 1992.

Boger et al, "CBI–CDPBO1 and CBI–CDPBI1:CC–1065 Analogs Containing Deep–seated Modifications in the DNA Binding Subunit," Bioorganic and Medicinal Chemistry, vol. 3, No. 6, 761–775, 1995.

Boger et al., "CC–1065 and the Duocarmycins: Understanding their Biological Function through Mechanistic Study," Angew.Chem.Int.Ed.Engl., vol. 35, 1438–1474, 1996.

Boger, et al., "DNA Alkylation Properties of the Duocarmycins⊗+)–Duocarmycin A, Epi–(+)–Duocarmycin A, Ent–(–)–Duocarmycin A and Epi,Ent–(–)–Duocarmycin A," Bioorganic and Medicinal Chemistry Letters, vol. 2, No. 7: 759–765, 1992.

Boger et al., "DNA Alkylation Properties of Enhanced Funuctional Analogs of CC–1065 Incorporating the 1,2,9,9a–Tetrahydrocyclopropra[c]benz[e]indol–4–one (CBI) Alkylation Subunit," Journal of the American Chemical Society, vol. 114, No. 14, 5487–5496, 1992.

Boger, et al., A Potent, Simple Derivative of an Analog of the CC–1065 Alkylation Subunit, Bioorganic and Medicinal Chemistry Letters, vol. 1, No. 1: 55–58, 1991.

Boger et al., "Reversed and Sandwiched Analogs of Duocarmycin SA: Establishment of the Origin of the Sequence–Selective Alkylation of DNA and New Insights into the Source of Catalysis," J.Am.Chem.Soc., vol. 119: 4987–4998, 1997.

Boger et al., "Synthesis of N–(tert–Butyloxycarbonyl)–CBI, CBI–CDPI1, and CBI–DCPI2; Enhanced Functional Analogues of CC–1065 Incorporating the 1,2,9,9a–Tetrahydrocyclopropa[c]benx[e]indol–4–one (CBI) Left–hand Subunit," J. Org. Chem. vol. 55:5823–5832, 1999.

Bremer et al., "Inhibition of Major–Groove–Binding Proteins by Pyrrole–Imidazole Polyamides with an Arg–Pro–Arg Positive Patch," Chem. & Biol., vol. 5:119–133, 1998.

Brooks et al., "Structure–Activity Relationship of a Series of C–terminus Modified Aminoalkyl, Diaminoalkyl– and Anilino–containing Analogues of the Benzoic Acid Mustard Distamycin Derivative Tallimustine: Synthesis, DNA Binding and Cytotoxicity Studies," Bioorganic and Medicinal Chemistry, vol. 5, No. 8: 1497–1501, 1997.

Brooks et al., "Synthesis, DNA Binding, Cytotoxicity and Sequence Specificity of a Series of Imidazole–containing Analogs of the Benzole Acid Mustard Distamycin Derivative Tallimustine Containing an Alkylating Group at the C–terminus," Anti–Cancer Drug Design, vol. 12: 591–606, 1997.

Church, et al., "N–(2–Chloroethyl)–N–nitrosourceas Covalently Bound to Nonionic and Monocationic Lexitropsin Dipeptides. Synthesis, DNA Affinity Binding Charcteristic and Reactions with 32P–End–Labeled DNA," Biochemistry, vol. 29: 6827–6838, 1990.

Ciucci et al., "Backbone and Benzoyl Mustard Carrying Moiety Modifies DNA Interactions of Distamycin Analogues," Nucleic Acids Research, vol. 24, No. 7:311–315, 1996.

Cozzi et al., "Novel Phenyl Nitrogen Mustard and Half–Mustard Derivatives of Amidino–Modified Distamycin," Bioorganic & Medicinal Chemistry Letters, vol. 7, No. 23: 2979–2984, 1997.

Cozzi et al., "Novel Phenyl Nitrogen Mustard and Half–Mustard Derivatives of Distamycin A," Bioorganic and Medicinal Chemistry Letters, vol. 7, No. 23: 2285–2290, 1997.

Dervan et al., "Sequence–specific DNA Recognition by Polyamides," Current Opinion in Chemical Biology, vol. 3:688–693, 1999.

Dickinson et al., "Inhibition of RNA Polymerase II Transcription in Human Cells by Synthetic DNA–binding Ligands," Proc. Natl. Acad. Sci., USA, vol. 95:12890–12895, 1998.

Ebbinghaus et al., "Inhibition of Transcription Elongation in the HER–2/neu Coding Sequence by Tri–plex–Directed Covalent Modification of the Template Strand," Biochemistry, vol. 38:619–628, 1999.

Fujiwara et al., "Modulation of Sequence Specificity of Duocarmycin–Dependent DNA Alkylation by Pyrrole–Imidazole Triamides," J. Am. Chem. Soc., vol. 121:7706–7707, 1999.

Iverson et al., "Adenine Specific DNA Chemical Sequencing Reaction," Nucleic Acid Research, vol. 15:7823–7830, 1987.

Johnston et al., "Autoradiography Using Storage Phophor Technology," Electrophoresis, vol. 11:355–360, 1990.

Kundu et al., "The Alkylating Properties of Chlorambucil," Pharmacology Biochemistry and Behavior, vol. 49:621–624, 1994, Lukhtanov et al., "Sequencing and Structure Dependence of the Hybridization–Triggered Reaction of Oligonucleotides Bearing Conjugated Cyclopropapyrroloindole," J. Am. Chem. Soc., vol. 119:6214–6225, 1997.

Matsuba et al., "A Novel Synthetic DNA Minor Groove Binder, MS–247: Antitumor Activity and Cytotoxic Mechanism," Cancer Chemother Pharmocol, vol. 46: 1–9, 2000.

Maxam et al., "Sequencing DNA by Labeling the End and Breaking at Bases: DNA Segments, End Labels, Clevage Reactions, Polyacrylamide Gels, and Strategies," Molekulyarnaya Biologiya, vol. 20:461–509, 1986.

Reynolds et al., "Reaction of the Antitumor Antibiotic CC–1065 with DNA," Biochemistry, vol. 24:6228–6237, 1985.

Tagliabue et al., "Combination of the New Minor Groove Alkylator Tallimustine and Melphalan," European Journal of Cancer, vol. 33: 284–287, 1997.

Tao et al., "Sequence–Specific DNA Alkylation by Hybrid Molecules Between Segement A of Duocarmycin A and Pyrrole/Imidazole Diamide," Agnew. Chem. Intl. Ed., vol. 38, No. 5, pp. 650–653, 1999.

Tao et al., "Rational Design of Sequence–Specific DNA Alkylating Agents Based on Duocarymcin A and Pyrrole~imidazole Hairpin Polyamides," J. Am. Chem. Soc., vol. 121:4961–4967, 1999.

White et al., "Recognition of the Four Watson–Crick Base Pairs in the DNA Minor Groove by Synthetic Ligands," Nature, vol. 391:468–471, 1998.

Wyatt et al., "Sequence Specificity of Alkylation for a Series of Nitrogen Mustard–Containing Analogues of Distamycin of Increasing Binding Site Size: Evidence for Increased Cytotoxicity with Enhanced Sequence Specificity," Biochemistry, vol. 34:13034–13041, 1995.

Wyatt et al., "The Sequence Specificity of Alkylation for a Series of Benzoid Acid Mustard and Imidazole–containing Distamycin Analogues: The Importance of Local Sequence Conformation," Nucleic Acids Research, vol. 25: 2359–2364, 1997.

* cited by examiner

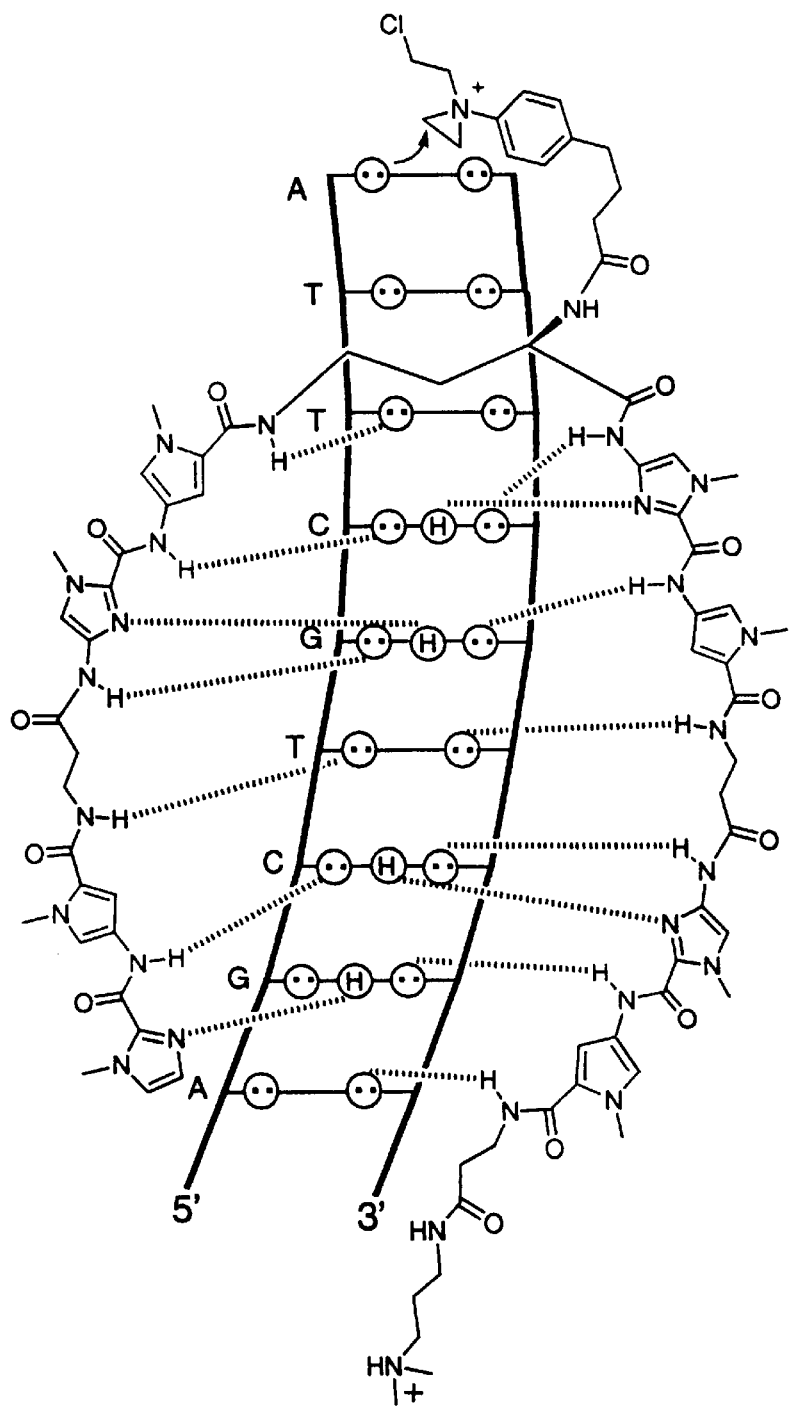
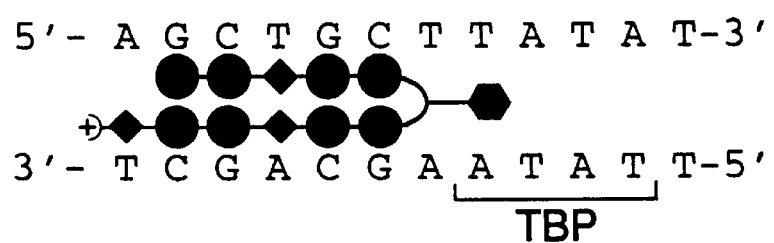
FIG. 1

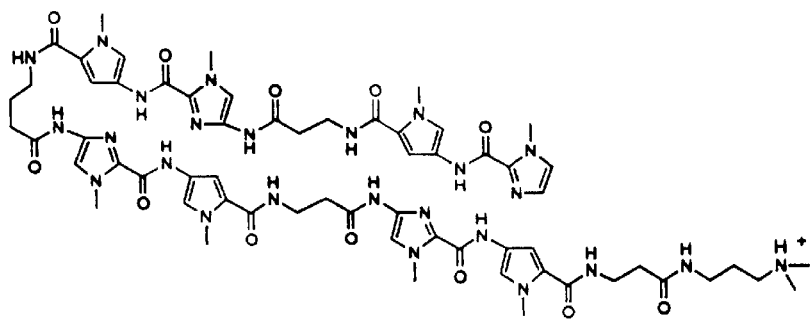
(1) ImPy-β-ImPy-γ-ImPy-β-ImPy-β-Dp
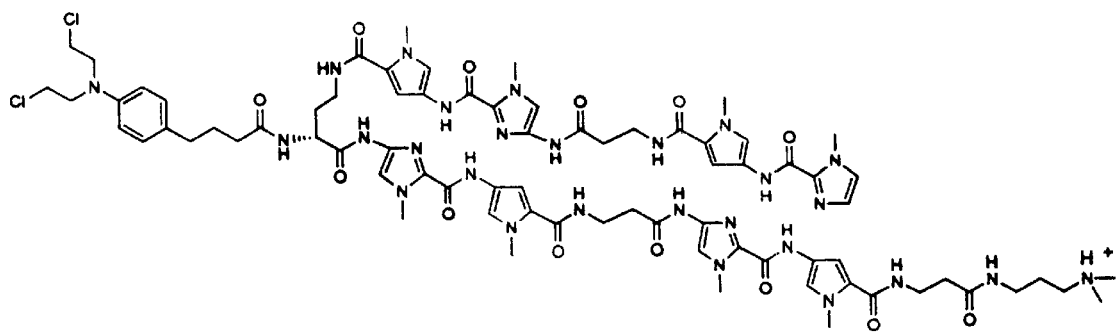
(2) ImPy-β-ImPy-(R)$^{CHL}$γ-ImPy-β-ImPy-β-Dp
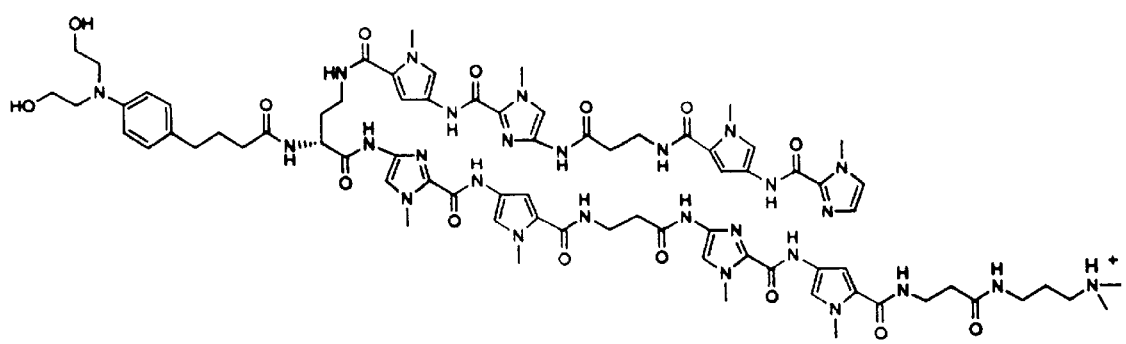
(3) ImPy-β-ImPy-(R)$^{CHL(OH)_2}$γ-ImPy-β-ImPy-β-Dp
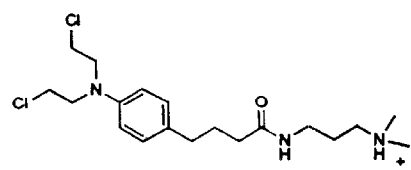
FIG. 3 (4) 4-{4-[bis(2-chloroethyl)amino]phenyl}-N-[3-(dimethylamino)propyl]butanamide

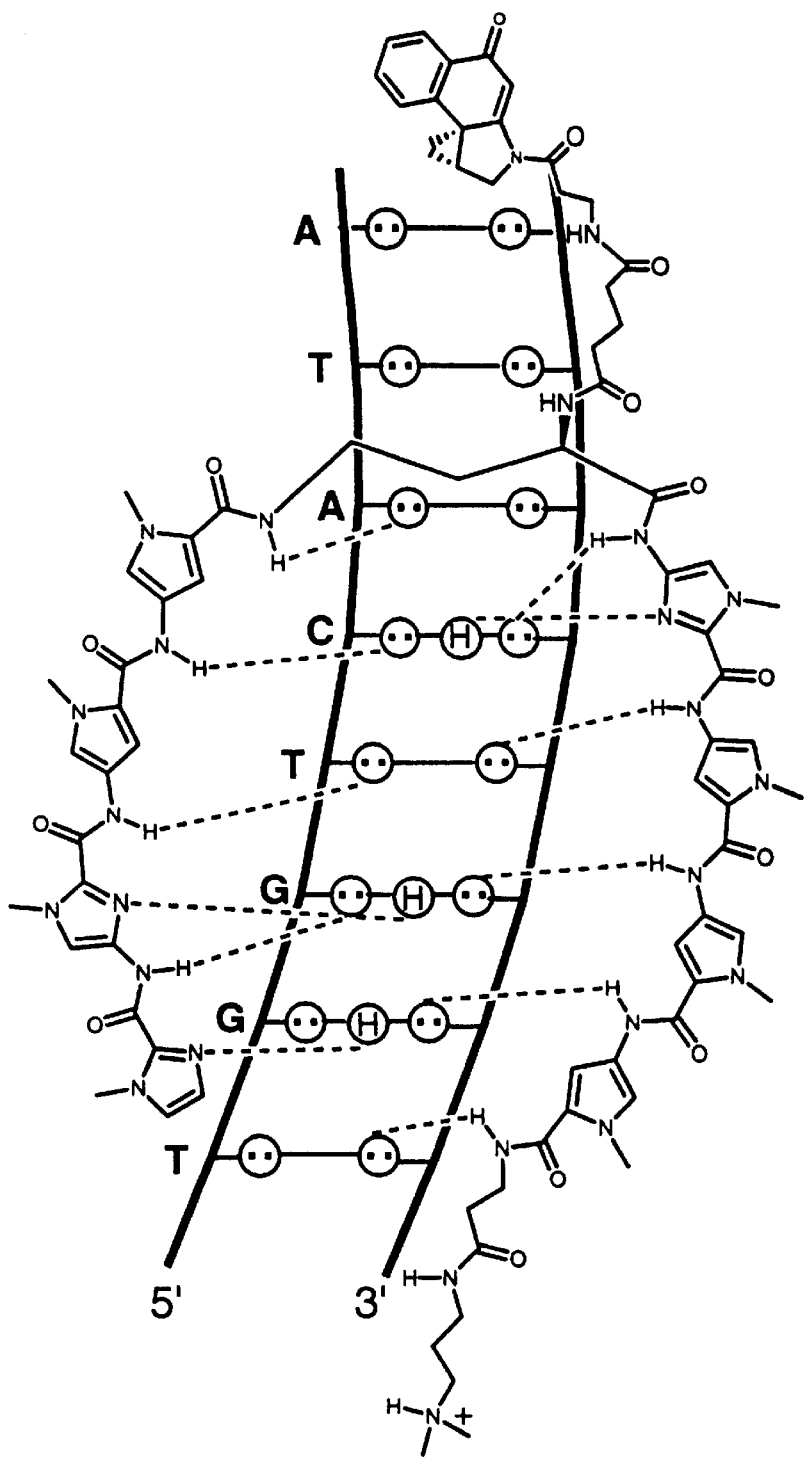
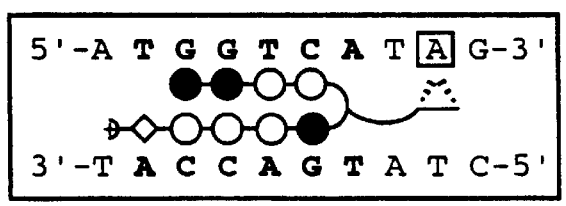
FIG. 10

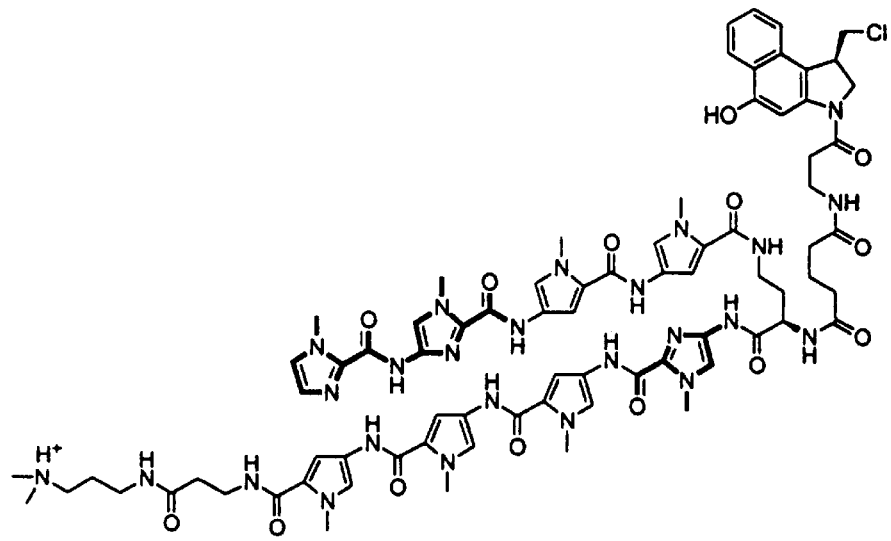
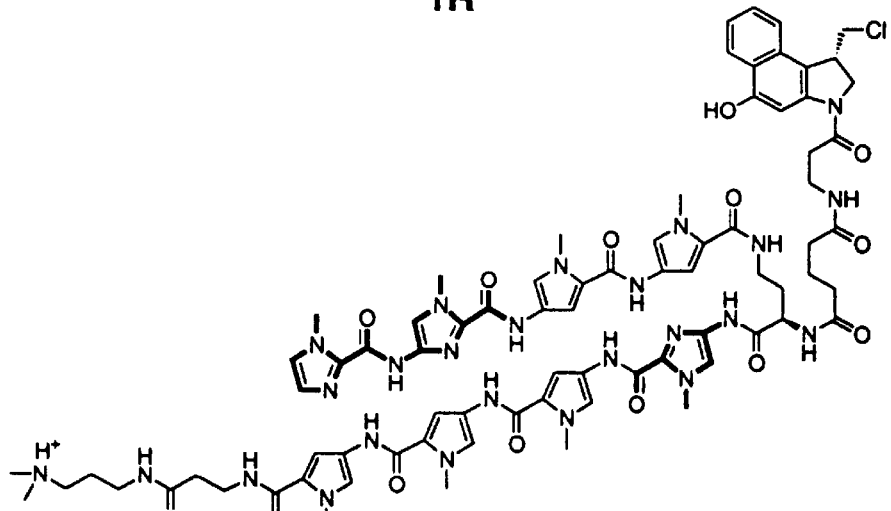
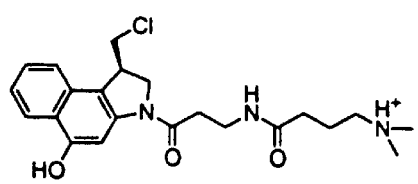
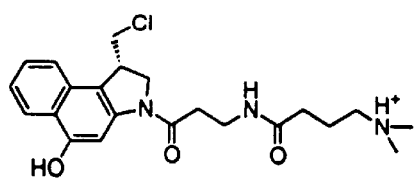
FIG. 12

POLYAMIDE-ALKYLATOR CONJUGATES AND RELATED PRODUCTS AND METHOD

This application claims the benefit of application No. 60/178,821, filed Jan. 28, 2000.

U.S. GOVERNMENT RIGHTS

The U.S. Government may have certain rights in this invention pursuant to Grant No. GM-27681 awarded by the National Institutes of Health.

FIELD OF THE INVENTION

This invention relates to polyamide-alkylator conjugates and related products, including methods of using such conjugates as well as methods relating to their synthesis.

BACKGROUND OF THE INVENTION

None of the following discussion of the background of the invention, which is provided solely to aid the reader in understanding the invention, is admitted to be or to describe prior art to the invention.

The design of synthetic ligands capable of reading information stored in the DNA double helix has been a long-standing goal of chemistry and molecular biology. Cell-permeable small molecules, which target predetermined nucleotide sequences in double-stranded nucleic acids, particularly double-stranded DNA (dsDNA), are useful in regulating, or modulating, gene-expression. Small molecules specifically targeted to any predetermined DNA sequence would be useful tools in molecular biology and potentially in human medicine.

Oligodeoxynucleotides that recognize the major groove of double-helical DNA via triple-helix formation bind to a broad range of sequences with high affinity and specificity. See Moser, et al., *Science, vol.* 238:645–650 (1987), Duvaivalentin, et al., *Proc. Nat'l Acad. Sci. USA, vol.* 89:504–508 (1992), Maher, et al., *Biochemistry, vol.* 31:70–81 (1992). Although oligonucleotides and their analogs have been shown to interfere with gene expression, the triple helix approach so far has been limited to purine tracks and suffers from poor cellular uptake.

Another recent approach to targeting specific nucleotide sequences in dsDNA has involved molecules known as "polyamides." See U.S. Ser. No. 08/607,078, PCT/US97/03332, U.S. Ser. Nos. 08/837,524, 08/853,525, PCT/US97/12733, U.S. Ser. No. 08/853,522, PCT/US97/12722, PCT/US98/06997, PCT/US98/02444, PCT/US98/02684, PCT/US98/01006, PCT/US98/03829, and PCT/US98/0714 all of which are incorporated herein by reference in their entirety, including any drawings. As described in the foregoing references, polyamides comprise polymers of amino acids covalently linked by amide bonds. Preferably, the amino acids used to form these polymers include N-methylpyrrole (Py) and N-methylimidazole (Im). Polyamides containing pyrrole (Py), and imidazole (Im) amino acids are synthetic ligands that have an affinity and specificity for DNA comparable to naturally occurring DNA binding proteins Trauger, J. W., Baird, E. E. & Dervan, P. B. (1996), *Nature* 382, 559–561; Swalley, S. E., Baird, E. E. & Dervan, P. B. (1997), *J. Am. Chem. Soc.* 119, 6953–6961; Turner, J. M., Baird, E. E. & Dervan, P. B. (1997), *J. Am. Chem. Soc.* 119, 7636–7644; Trauger, J. W., Baird, E. E. & Dervan, P. B. (1998), *Angewandte Chemie-International Edition* 37, 1421–1423; and Dervan, P. B. & Burli, R. W. (1999), *Current Opinion in Chemical Biology* 3, 688–693.

The particular order of amino acids in such polyamides, and their pairing in dimeric, antiparallel complexes formed by association of two polyamide polymers, determines the sequence of nucleotides in dsDNA with which the polymers preferably associate. The development of pairing rules for minor groove binding polyamides derived from N-methylpyrrole (Py) and N-methylimidazole (Im) amino acids provided a useful code to control target nucleotide base pair sequence specificity. Specifically, an Im/Py pair in adjacent polymers was found to distinguish G•C from C•G and both of these from A•T or T•A base pairs. A Py/Py pair was found to specify A•T from G•C but could not distinguish A•T from T•A. More recently, it has been discovered that inclusion of a new aromatic amino acid, 3-hydroxy-N-methylpyrrole (Hp) (made by replacing a single hydrogen atom in Py with a hydroxy group), in a polyamide and paired opposite Py enables A•T to be discriminated from T•A by an order of magnitude. Utilizing Hp together with Py and Im in polyamides provides a code to distinguish all four Watson-Crick base pairs (i.e.. A•T, T•A, G•C, and C•G) in the minor groove of dsDNA, as described in Table 1.

TABLE 1

| Pairing Code for Minor Groove Recognition | | | | |
|---|---|---|---|---|
| Pair | G · C | C · G | T · A | A · T |
| Im/Py | + | − | − | − |
| Py/Im | − | + | − | − |
| Hp/Py | − | − | + | − |
| Py/Hp | − | − | − | + |

Favored (+), disfavored (−)

As discussed above, a number of different polyamide motifs have been reported in the literature, including "hairpins," "H-pins," "overlapped," "slipped," and "extended" polyamide motifs. Specifically, hairpin polyamides are those wherein the carboxy terminus of one amino acid polymer is linked via a linker molecule, typically aminobutyric acid or a derivative thereof to the amino terminus of the second polymer portion of the polyamide. Indeed, the linker amino acid γ-aminobutyric acid (γ), when used to connect first and second polyamide polymer portions, or polyamide subunits, C→N in a "hairpin motif," enables construction of polyamides that bind to predetermined target sites in dsDNA with more than 100-fold enhanced affinity relative to unlinked polyamide subunits. See, for example, Turner, et al., *J. Am. Chem. Soc., vol.* 119:7636–7644 (1997), Trauger, et al., *Angew. Chemie. Int. Ed. Eng., vol.* 37: 1421–1423 (1997), Turner, et al., *J. Am. Chem. Soc., vol.* 120:6219–6226 (1998), and Trauger, et al., *J. Am. Chem. Soc., vol.* 120:3534–3535 (1998). Paired β-alanine residues (β/β), restore the curvature of the dimer for recognition of larger binding sites and in addition, code for AT/TA base pairs Trauger, J. W., Baird, E. E., Mrksich, M. & Dervan, P. B. (1996), *J. Am. Chem. Soc.* 118, 6160–6166; Swalley, S. E., Baird, E. E. & Dervan, P. B. (1997), *Chem.-Eur. J.* 3, 1600–1607; and Trauger, J. W., Baird, E. E. & Dervan, P. B. (1998), *J. Am. Chem. Soc.* 120, 3534–3535. Eight ring hairpin polyamides can bind a 6 base pair match sequence at subnanomolar concentrations with good sensitivity to mismatch sequences. Dervan, P. B. et al. *Curr. Opin. Chem. Biol.* 1999, 3,688–693. Moreover, eight-ring hairpin polyamides (comprised of two four amino acid polymer portions linked C→N) have been found to regulate transcription and permeate a variety of cell types in culture. See Gottesfield, J. M.; et al., *Nature, vol.* 387:202–205 (1997).

An H-pin polyamide motif, i.e., wherein two paired, antiparallel polyamide subunits are linked by a linker covalently attached to an internal polyamide pair, have also been reported. Another polyamide motif that can be formed between linked or unlinked polyamide subunits is an "extended" motif, wherein one of the polyamide subunits comprises more amino acids than the other, and thus has a single-stranded region. See U.S. Ser. No. 08/607,078. In contrast, an "overlapped" polyamide is one wherein the antiparallel polyamide subunits completely overlap, whereas in a "slipped" binding motif, the two subunits overlap only partially, with the C-terminal portions not associating with the N-terminal regions of the other subunit. See U.S. Ser. No. 08/607,078.

DNA alkylation by Duocarmycin A segment—hairpin polyamide conjugates is described in Tao et al., J. Am. Chem. Soc. 1999, 121:4961–4967. Alkylation by one such conjugate was reported to proceed with efficiency at nanomolar concentration against a particular DNA sequence. Other Duocarmycin A experiments we reported in Fujiwara, et al. J. Am. Chem. Soc. 1999, 121:7706–7702 and Tao, et al. Agnew. Chem. Int. Ed. 1999, 38; No. 5, pages 650–653.

SUMMARY OF THE INVENTION

The present invention is based on the surprising and unexpected discovery of new and useful polyamide-alkylator conjugates. As a result of their DNA binding properties, polyamides deliver reactive moieties for covalent reaction at specific DNA sequences and thereby inhibit DNA-protein interactions. This site specific alkylation of DNA is a useful tool to regulate gene expression. In addition to competing with transcription factors or promoters, the conjugates of the present invention will be used to target a gene's coding region. This will allow use of synthetic chemistry to create a new class of gene specific "knockout" reagents which will be useful in biological disciplines.

We have designed and synthesized a class of hairpin polyamides equipped with DNA alkylating agents and characterized the specificity and yield of covalent modification. In one instance Bis(dichloroethylamino)benzene derivatives of the well-characterized alkylator chlorambucil (CHL) were attached to the γ-turn of an eight ring hairpin polyamide targeted to the HIV promoter. The hairpin polyamide-CHL conjugate binds and selectively alkylates predetermined sites in the HIV promoter at subnanomolar concentrations. Cleavage sites were determined on both strands of a restriction fragment containing the HIV-1 promoter revealing good specificity and high yield of alkylation. The ability of polyamide-CHL conjugates to sequence specifically alkylate double stranded DNA in high yield and at low concentration indicates their use as regulators of gene expression in cell culture and complex organisms.

In another instance, we synthesised and characterized an eight-ring hairpin polyamide conjugated at the γ-turn to both enantiomers of 1-(chloromethyl)-5-hydroxy-1,2-dihydro-3H-benz[e]indole (seco-CBI), an alkylating moiety related to CC-1065. We attached the seco-CBI unit to the hairpin turn. In addition, we used the two different diastereomers which afforded opposite strand reactivity in the minor groove depending on mirror image (FIG. 11) (SEQ ID NO:17). Alkylation yield and specificity were determined on a restriction fragment containing six base pair match and mismatch sites. Alkylation was observed at a single adenine flanking the polyamide binding site, and strand selective cleavage could be achieved based on the enantiomer of seco-CBI chosen. At 1 nM concentrations of polyamide-seco-CBI conjugate, near quantitative cleavage was observed after 12 hours. Thus, these bifunctional molecules are useful for targeting coding regions of genes and inhibition of transcription.

Thus, in one aspect, the invention provides a polyamide-alkylator conjugate. The conjugate contains an alkylator linked to a polyamide. The polyamide contains at least one pyrrole or imidazole amino acid and may bind DNA with subnanomolar binding affinity. The alkylator is linked to the y-aminobutyric acid (or other turn moiety) of a hairpin polyamide or the alkylator selectively alkylates only one strand of a double-stranded DNA. By "turn moiety" is meant a chemical group that operates to orient two strands or segments of a polyamide substantially parallel to one another. Preferred turn moieties are those which comprise an aliphatic chain, for example, aminobutyric acid, with the latter being particularly preferred. Particularly preferred aminobutyric acids include γ-aminobutyric acid, particularly substituted derivatives thereof, for example, (R)-2,4-diaminobutyric acid. Preferably, the conjugate of the invention has separate domains for DNA binding (e.g., the polyamide region of the conjugate) and DNA covalent attachment (e.g., the alkylation region of the conjugate).

The term "polyamide" is used to describe a minor groove-targeting polypeptide, which is a polymer of amino acids chemically bound by amide linkages (CONH). An "amino acid" is defined as an organic molecule containing both an amino group ($NH_2$) and a carboxylic acid (COOH). The polyamides of this invention may be comprised of imidazole carboxamides, pyrrole carboxamides, aliphatic amino acids, aromatic amino acids and any chemical modifications thereof. In preferred embodiments, the polyamide is a hairpin polyamide, for example a hairpin polyamide that contains eight or more heterocyclic rings, wherein each of the eight heterocylic rings is a pyrrole ring or an imidazole ring. The polyamide preferably binds DNA with subnanomolar binding affinity, which is measured as described in examples herein.

As used herein "polyamide" preferably refers to a polymer derived from subunits chosen from the set below, in the form of the corresponding carboxamides:

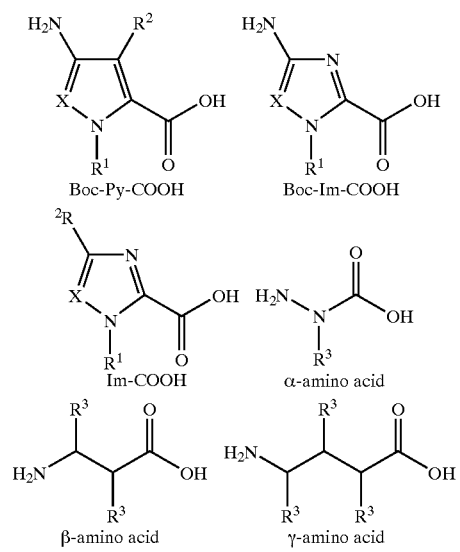

where $R^1$ is $C_{1-100}$ alkyl (preferably $C_{1-10}$ alkyl such as methyl, ethyl, isopropyl), $C_{1-100}$ alkylamine (preferably $C_{1-10}$ alkylamine such as ethylamine), $C_{1-100}$ alkyldiamine (preferably $C_{1-10}$ alkyldiamine such as N,N-dimethylpropylamine), a $C_{1-100}$ alkylcarboxylate (preferably a $C_{1-10}$ alkylcarboxylate such as $CH_2COOH$), $C_{1-100}$ alkenyl (preferably $C_{1-10}$ alkenyl such as $CH_2CH=CH_2$), or a $C_{1-100}$ alkynyl (preferably $C_{1-10}$ alkenyl such as $CH_2CH\equiv CH_3$), or a $C_{1-100}L$, where L groups can be independently chosen from biotin, oligodeoxynucleotide, N-ethylnitrosourea, fluorescein, bromoacetamide. iodoacetamide, DL-α-lipoic acid, acridine, ethyl red, 4-(psoraen-8-yloxy)-butyrate, tartaric acid, (+)-α-tocopheral;

where $R^2$ and $^2R$ are independently chosen from H, $NH_2$, OH, SH, Cl, Br, F, N-acetyl, or N-formyl;

where $R^3$ is H, $NH_2$, OH, SH, Br, Cl, F, OMe, $CH_2OH$, $CH_2SH$, $CH_2NH_2$; and where X is chosen from N, CH, COH, $CCH_3$, $CNH_2$, CCl, CF.

More preferably, "polyamide" refers to a polymer of comprising one or more subunits of the formula (II), below

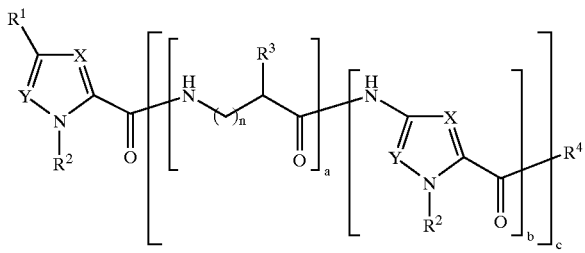

where $R^1$ is chosen from H, $NH_2$, SH, Cl, Br, F, N-acetyl, or N-formyl;

where $R^2$ is $C_{1-100}$ alkyl (preferably $C_{1-10}$ alkyl such as methyl, ethyl, isopropyl), $C_{1-100}$ alkylamine (preferably $C_{1-10}$ alkylamine such as ethylamine), $C_{1-100}$ alkyldiamine (preferably $C_{1-10}$ alkyldiamine such as N,N-dimethylpropylamine), a $C_{1-100}$ alkylcarboxylate (preferably a $C_{1-10}$ alkylcarboxylate such as $CH_2COOH$), $C_{1-100}$ alkenyl (preferably $C_{1-10}$ alkenyl such as $CH_2CH=CH_2$), or a $C_{1-100}$ alkynyl (preferably $C_{1-10}$ alkynyl such as $-C_2C\equiv CH_3$), or a $C_{1-100}L$, where L groups can be independently chose from biotin, oligodeoxynucleotide, N-ethylnitrosourea, fluorescein, bromoacetamide, iodoacetamide, DL-α-lipoic acid, acridine, ethyl red, 4-(psoraen-8-yloxy)-butyrate, tartaric acid, (+)-α-tocopherol;

where $R^3$ is chosen from H, $NH_2$, OH, SH, Br, Cl, F, Ome, $CH_2OH$, $CH_2SH$, $CH_2NH_2$;

where $R^4$ is $-NH$ $(CH_2)_{0-100}NR^5R^6$ or $NH(CH_2)_mCO$ $NH(CH_2)_{0-100}$ $NR^5R^6$ or $NHR^5$ or $NH(CH_2)_m$ $CONHR^5$; Where $R^5$ and $R^6$ are independently chosen from H, Cl, NO, N-acetyl, benzyl, $C_{1-100}$ alkyl, $C_{1-100}$ alkylamine, $C_{1-100}$ alkyldiamine, $C_{1-100}$ alkylcarboxylate, $C_{1-100}$ alkenyl, a $C_{1-100}$ alkynyl; where m is an integer value ranging from 0 to 12;

where X and Y are chosen from the following, N, CH, COH, $CCH_3$, $CNH_2$, CCl, CF;

a is an integer chosen from values of 0 or 1 b is an integer chosen integer values ranging from 1 to 5; and c is an integer value ranging from 2 to 10.

Hereinafter, N-methylpyrrolecarboxamide may be referred to as "Py", N-methylimidazolecarboxamide may be referred to as "Im", γ-aminobutyric acid may be referred to as "γ", β-alanine may be referred to as "β", glycine may be referred to as "G", dimethylaminopropylamide may be referred to as "Dp", and ethylenediaminetetraacetic acid may be referred to as "EDTA".

By "alkylator" is meant a compound that reacts with and adds an alkyl group to another molecule. In preferred embodiments, the alkylator is reactive with DNA at about 37 degrees celsius, the alkylator is substantially inert in aqueous media, and/or the conjugate is present in a buffer and the alkylator is non-reactive with the buffer. The alkylator may be cyclophosphamide, nitrosoureas, mitozolomide, anthramycin, bromoacetyl, a nitrogen mustard, a derivative of chlorambucil (such as a Bis(dichloroethylamino)benzene derivative), seco-CBI, mitomycin, initomycin C, or (+)-CC-1065. Seco-CBI is a precursor to 1,2,9,9a-tetrahydrocyclopropa[1,2-c]benz[1,2-e]indol-4-one (CBI), [Boger, D. L. et al. Bioorgan. Med. Chem. 1995, 3, 1429–1453; and Boger, D. L. and Johnson, D. S. Angew. Chem., Int. Ed. Engl.1996, 35, 1438–1474] an analogue of the natural product (+)-CC-1065. CBI shows increased reactivity to DNA as well as increased stability to solvolysis. [Boger, D. L. and Munk, S. A. J. Am. Chem. Soc. 1992, 114, 5487–5496.] The seco agents readily close to the cyclopropane forms and have equivalent reactivity as compared to CBI, but have been shown to have longer shelf lives. [Boger, D. L. et al. Bioorg. Med. Chem. Lett. 1991, 1, 55–58.]

By "linked" is meant that there is a chemical connection between the polyamide and the alkylator. Preferably the linkage is a covalent bond, but the term linked also encompasses non-convalent interactions such as hydrogen bonding, Van der Waals interactions, hydrophobic interactions, and ionic bonding.

In certain preferred embodiments, the alkylator is linked (e.g., covalently linked) to the γ-aminobutyric acid of the polyamide (in particular, the alkylator may be covalently attached to a chiral α-amino group on the γ-aminobutyric acid of the polyamide), while in other preferred embodiments the alkylator selectively alkylates only one strand of a double-stranded DNA (i.e., only the 5' strand or only the 3' strand). For example, the alkylator may selectively alkylate only one strand of a double-stranded DNA when the polyamide portion of the conjugate interacts with the DNA (e.g., is covalently bound to the DNA). As noted above, in other preferred embodiments the polyamide binds to DNA with subnanomolar binding affinity.

As used herein, "subnanomolar affinity" means binding that is characterized by a dissociation constant, $K_d$, of less than 1 nM, as measured by DNase I footprint titration. Preferably, polyamides and/or conjugates of the present invention are characterized by subnanomolar binding affinity for the identified target DNA sequence. As used herein, the "selectivity" of the binding of a polyamide or conjugate to a DNA sequence is the ratio of the dissociation constant, $K_d$, as measured by DNase I footprint titration of binding the polyamide or conjugate to a mismatch DNA sequence divided by the corresponding dissociation constant of the binding of the polyamide or conjugate to the identified target DNA sequence. Preferably, polyamides and/or conjugates of the present invention are characterized by a selectivity of about 5 or greater, more preferably a selectivity of greater that about 10. Of course any combination of the above embodiment is possible, i.e., the alkylator may selectively alkylate only one strand of dsDNA and the polyamide may bind DNA with subnanomolar binding affinity.

The conjugate preferably is capable of sequence specific alkylation of DNA, including sequence specific alkylation of DNA in the minor groove. Thus, the conjugate can be designed to target a predetermined DNA sequence. The conjugate preferably alkylates an adenine adjacent to the binding site and/or has sub-nanomolar binding affinity for the DNA. Preferably, the conjugate is also selective, for example the conjugate has at least 20-fold (more preferably about 100-fold) greater affinity for a target site than for a site differing from the target site by two amino acids. Preferably, a conjugate will interact with its target nucleotide base pair sequence with an affinity, as measured by DNase footprint titration, of less than about 100 nM, preferably less than about 10 nM, more preferably less than about 1.0 nM, even more preferably less than about 0.1 nM. Thus, the conjugates of the invention have substantially the same binding affinity and specificity as the polyamide.

The rate of alkylation is an important measure of polyamide-alkylator ,conjugates. The conjugates of the invention preferably alkylate the DNA at a rate whereby alkylation is at least half completed at one or more match sites in about 2.2 hours, more preferably alkylate the DNA at a rate whereby final cleavage yield on the bottom strand of the DNA is about 45% and even more preferably alkylate the DNA at a rate whereby final cleavage yield on the bottom strand of the DNA is about 96%.

In another aspect, the invention provides a composition containing a conjugate of the invention in a pharmaceutically acceptable carrier. A method of making the composition of the invention is also provided and involves the step of providing a conjugate of the invention in a pharmaceutically acceptable carrier. Pharmaceutical formulations of the invention are described in detail in a section below.

In yet another aspect, the invention features a method of using a conjugate or composition of the invention to deliver a reactive moiety for covalent reaction at one or more DNA sequences. The method involves the step of administering the conjugate or the composition to an organism and thereby modulates DNA-protein interactions and/or gene expression comprising. In a preferred embodiment, the DNA is in the coding region of a gene. Again, detailed procedures for administration are provided in a separate section below. Administration preferably is of a therapeutically effective amount of the agent being administered.

A "therapeutically effective" amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein, A "thereapeutically effective amount," in reference to the treatment of a cancer refers to an amount sufficient to bring about one or more of the following results: reduce the size of the cancer, inhibit the metastasis of the cancer, inhibit the growth of the cancer, stop the growth of the cancer, relieve discomfort due to the cancer, or prolong the life of a patient inflicted with the cancer. A "therapeutically effective amount", in reference to the treatment of a cell proliferative disorder other than a cancer refers to an amount sufficient to bring about one or more of the following results: inhibit the growth cells causing the disorder, relieve discomfort due to the disorder, or prolong the life of a patient suffering from the disorder.

The invention also features a method of treating an organism by using two or more conjugates of the invention to selectively remove undesired gene segments or integrated viral DNA's from a host genome in vivo. The term "treating" refers to having a therapeutic effect and at least partially alleviating or abrogating an abnormal condition in the organism. The term "treating" preferably refers to ameliorating a symptom of the abnormal condition in a group of patients to whom the conjugate is administered relative to a control group that does not receive the conjugate. The effect of the treatment can be monitored by measuring a change or an absence of a change in cell phenotype, a change or an absence of a change in cell proliferation. The term "treating" or "treatment" does not necessarily mean total cure. Any alleviation of any undesired symptom of the disease to any extent or the slowing down of the progress of the disease can be considered treatment. Furthermore, treatment may include acts which may worsen the patient's overall feeling of well being or appearance. For example, the administration of chemotherapy in cancer patients which may leave the patients feeling "sicker" is still considered treatment. The method of treatment involves the steps of administering two or more conjugates of the invention to the organism having undesired gene segments or integrated viral DNA's and thereby selectively removing the undesired gene segments or the integrated viral DNA's. The conjugates preferably are selected so that one alkylates the initial amino acid of the sequence to be removed and the other conjugate targets the terminal amino acid of such a sequence. The term "organism" relates to any living entity comprised of at least one cell. An organism can be as simple as one eukaryotic cell or as complex as a mammal. The organism is preferably a mammal, more preferably a human. The term "mammal" refers preferably to such organisms as mice, rats, rabbits, guinea pigs, sheep, and goats, more preferably to cats, dogs, monkeys, and apes.

In another aspect, the invention features a method of making a conjugate of the invention. The method involves the steps of coupling the alkylator to the polyamide under conditions whereby the polyamide links to the alkylator and forms the polyamide-alkylator conjugate. Detailed procedures for making preferred conjugates of the invention are provided in the examples below and those skilled in the art would be able to make other conjugates of the invention based on these examples. A hairpin polyamide-bromoacrylic acid conjugate can be synthesized in an analogous manner. The free amino of the (R)-2,4 diaminobutyric acid in the γ-turn position of the polyamide can be coupled to bromoacrylic acid with EDC as the coupling agent.

Other aspects of the invention feature a cell containing a conjugate of the invention and a method of making such a cell by providing the conjugate to a cell under conditions whereby the conjugate enters the cell. Also featured is a method of using such a cell which involves the step of administering a test compound to the cell and measuring the effect of the test compound on the cell. Another method of using such a cell is in a method of treating an organism which involves the step of administering the cell to an organism in need of such treatment.

Other aspects relate to methods of using the conjugates of the invention. One area of application relates to the modulation of gene expression. "Modulation" refers to activating, increasing, enhancing, derepressing, reducing, decreasing, inhibiting, or preventing expression of a gene. Thus, some conjugatess positively affect, or up-regulate, gene expression, while others negatively affect, or down regulate, gene expression. A "gene" refers to genetic locus that encodes one or more gene products. As those in the art will appreciate, a gene can encode more than one gene product by virtue of differential mRNA splicing. Gene products include proteins (e.g., enzymes, receptors, antibodies, growth factors, and hormones) and RNA molecules, particularly tRNAs, ribosomal RNAs and other RNAs which are subunits of multi-component complexes (e.g., telomerase), and catalytic RNAs (e.g., ribozymes). To achieve the desired level of modulation in systems comprising cells, it is necessary to deliver a sufficient quantity of a conjugate according to the invention to the cells.

In some embodiments, the use of conjugates according to the invention can modulate the expression of more than one gene. For example, more than one conjugate, each of which specifically modulates a particular gene, can be delivered. Alternatively, the conjugate may directly influence the expression of more than one gene. For example, if the conjugate targets a nucleotide base pair sequence found in a regulatory region of more than one gene, modulation of expression of multiple genes may occur. Alternatively, the conjugate may exhibit its expression-modulating effects indirectly, or by a combination of direct and indirect effects. For instance, if the conjugate inhibits expression of a phosphatase that removes phosphates from a plurality of proteins, the expression of genes regulated by pathways that involve the phosphatase will be affected.

Certain embodiments of this aspect concern modulation of gene expression in vitro. "In vitro" includes both in situ and cell-free environments (e.g., a cell extract or in a well-defined reaction medium). Thus, the conjugatess of the invention can be used to modulate gene expression in cultured cells, such as may be used in ex vivo therapy or research.

Other embodiments of this aspect relate to the modulation of gene expression in vivo, some of which concern therapeutic purposes. As used herein, a "therapeutic purpose" includes both therapy (i.e., treatment of an existing condition) and prophylaxis (i.e., prevention). Representative examples of a therapeutic purpose include treatment of a disease associated with aberrant expression of the gene of interest (as occurs in certain cancers and genetic diseases, for example), as well as treatment of a disease associated with the presence of a pathogen (a virus or a bacterial or eukaryotic pathogenic organism).

Conjugates according to the invention can be used for therapeutic purposes in conjunction with a vast array of organisms, including both animals and plants. Preferred animals amenable to application of the therapeutic and prophylactic methods herein described include animals of agricultural importance, for example, avian (particularly poultry), bovine, equine, ovine, and porcine animals, companion animals such as dogs and cats, and humans. With regard to plants, preferred plants include those of agricultural importance, including cereals, grains, and grasses. Similarly, conjugatess according to the invention can be developed to control pests, e.g., certain insects and rodents.

The summary of the invention described above is non-limiting and other features and advantages of the invention will be apparent from the following description of the preferred embodiments, and from the claims.

BRIEF DESCRIPTION OF THE DRAWINGS

FIG. 1 shows, at the top, the hydrogen-bonding model and alkylation mechanism of polyamide-chlorambucil conjugate ImPy-βImPy-(R)$^{CHL}$γ-ImPy-β-ImPy-β-Dp (2) bound to the minor groove of 5'-AGCTGCT-3'. Circles with two dots represent the lone pairs of N3 purines and O2 of pyrimidines. Circles containing an H represent the N2 hydrogens of guanines. Putative hydrogen bonds are illustrated by dotted lines. Py and Im rings are represented as blue and red rings, respectively. The putative alkylating intermediate is green. Bottom, model of polyamide conjugate 2 (SEQ ID NO:1) bound to the match site 5'-AGCTGCT-3'. Red and blue circles represent imidazole (Im) and pyrrole (Py) polya- mide rings, respectively. Blue diamonds and green hexagons represent β-alanine (β) and chlorambucil (CHL) respectively. (R)-2,4-diaminobutyric acid ((R)γ) and dimethylaminopropylamide (Dp) are depicted as a curved line and a plus sign, respectively.

FIG. 3 depicts the structures of polyamides 1–3 and a nonspecific alkylator 4. ImPy-β-ImPy-γ-ImPy-β-ImPy-β-Dp, 1; ImPy-β-ImPy-(R)$^{CHL}$γ-ImPy-β-ImPy-β-Dp, 2; ImPy-β-ImPy-(R)$^{CHL(OH)}$γ-ImPy-β-ImPy-β-Dp, 3; 4-{4-[bis (2-chloroethyl)amino]phenyl}-N-[3-(dimethylamino) propyl]butanamide, 4.

FIG. 10, at the top, shows a hydrogen bond model of the polyamide-DNA complex formed by the polyamide-DNA complex formed by the polyamide ImImPyPy-γ$^{(S-CBI)}$-ImPyPyPy-β-Dp bound to the minor groove of 5'-TGGTCA-3'. Circles with dots represent lone pairs of N3 purines and O2 of pyrimidines. Circles containing an H represent the N2 hydrogen of G. Putative hydrogen bonds are illustrated by dotted lines. FIG. 10, at the bottom (SEQ ID NO:16), shows a binding model for polyamide ImImPyPy-γ$^{(S-CBI)}$-ImPyPyPy-β-Dp with a 5'-TGGTCA-3' site. Shaded and nonshaded circles denote imidazole (Im) and pyrrole (Py) rings, respectively. Diamonds and hatched triangles represent β-alanine (β) and (S)-CBI, respectively. (R)-2,4-diaminobutyric acid (γ) and dimethylaminopropylamine (Dp) are depicted as a curved line and a plus sign, respectively.

FIG. 12 is an illistration of the 277 base pair EcoRI/ HindIII restriction fragment with the position of the sequence indicated. The binding sites for polyamide 1', 5'-AGGACT-3' and 5'-TGGTCA-3' are boxed.

Figures 18A, 18B, 18C, 18D:
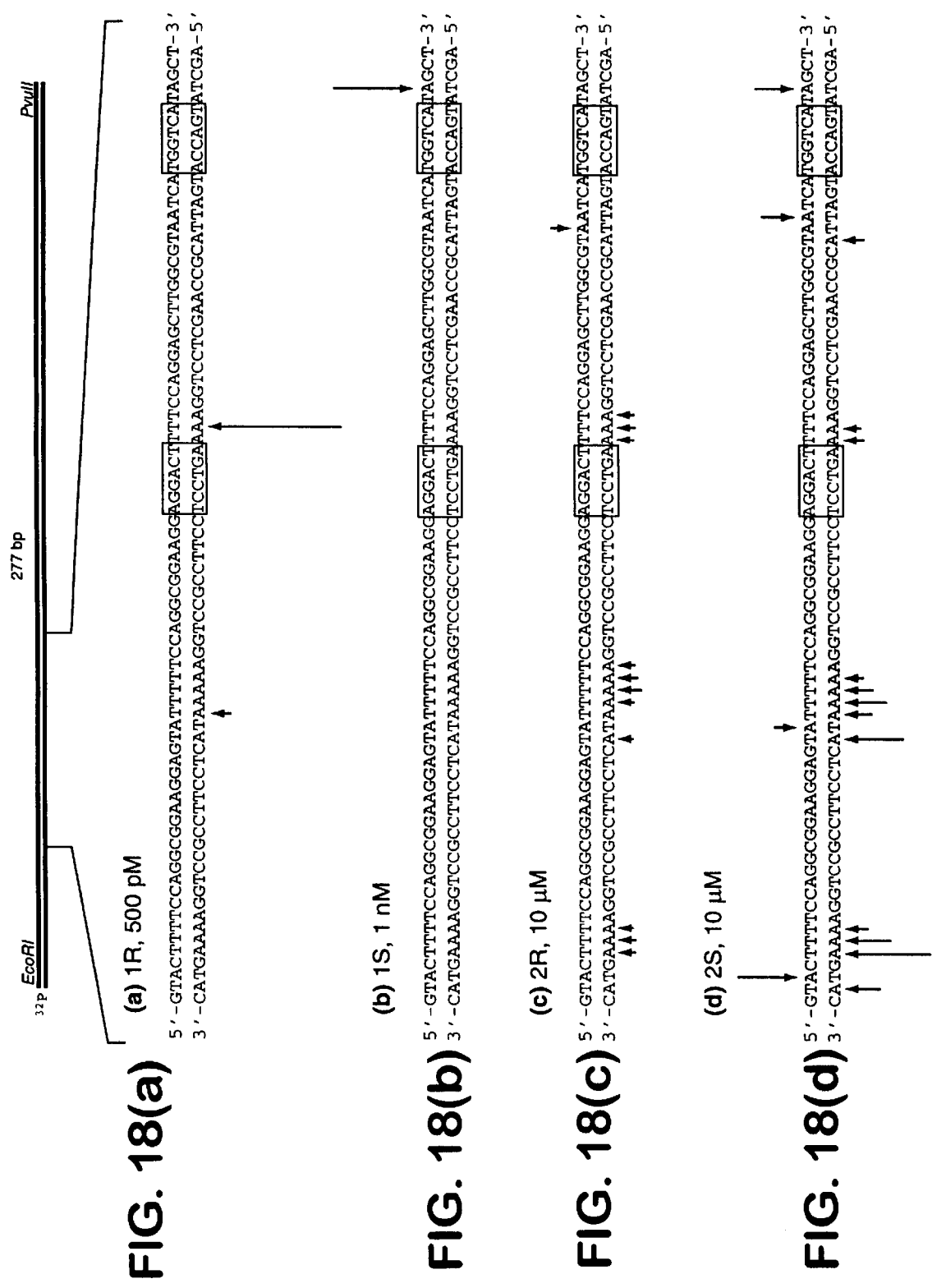

FIG. 18 is an illustration of the 277 bp restriction fragment (SEQ ID NO:19) with the position of the sequence indicated. Cleavage patterns are shown for (a) ImImPyPy-$\gamma^{(R\text{-}seco\text{-}CBI)}$-ImPyPyPy-$\beta$-Dp (1R), 500 pM; (b) ImImPyPy-$\gamma^{(S\text{-}seco\text{-}CBI)}$-ImPyPyPy-$\beta$-Dp (1S), 1 nM; (c) (R)-seco-CBI-$\beta$-dimethyl-$\gamma$ (2R), 10 $\mu$M; and (d) (S)-seco-CBI-$\beta$-dimethyl-$\gamma$ (2S), 10 $\mu$M.

DETAILED DESCRIPTION OF THE INVENTION

Figure 2:
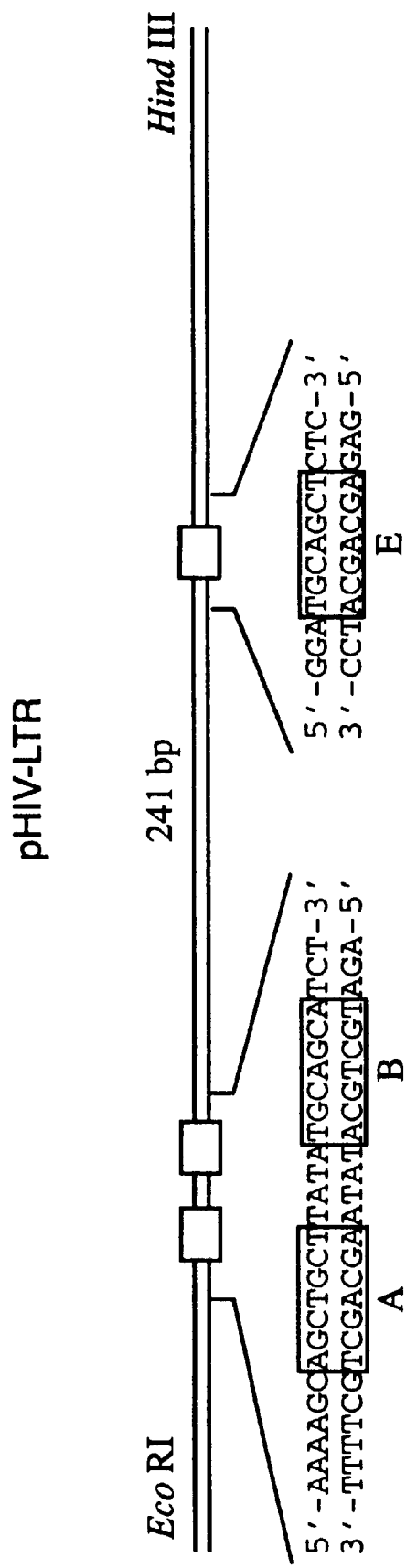
FIG. 2 is an illustration of the 241 bp pHIV-LTR EcoRI/HindIII restriction fragment with the position of the sequences indicated (SEQ ID NOS: 2 and 3). The binding sites 5'-AGCTGCT-3',5'-TGCAGCA-3' and 5'-TGCAGCT-3' are highlighted in blue.

The present invention is based on the surprising discovery of novel polyamide-alkylator conjugates. The polyamide portion of the conjugate is preferably a hairpin polyamide. Those skilled in the art are aware of various known hairpin polyamides, for example as described in the various patent applications incorporated by reference above in the Background of the Invention Section. Given this same information, those skilled in the art can also design and synthesize novel hairpin polyamides that can be used in the present invention. Especially preferred polyamides are those that bind DNA with subnanomolar binding affinity. Again, such polyamides are known and additional such polyamides can be designed and made using the information described in the applications referenced above. The alkylator portion of the conjugate also can be any known or later discovered alkylator. Preferred alkylators are chiral enatiomers that can selectively alkylate only one strand of a dsDNA. The design, synthesis, and use of such conjugates is described in detail below.

I. Polyamide Synthesis

Any suitable method can be employed to synthesize polyamides used in conjugates of the invention. Such methods include those performed in solution and those performed on a solid support. The latter method is particularly preferred when synthesizing relatively small quantities (e.g., less than one gram) of a plurality of polyamides, as may occur in the production of a library of polyamides for screening against one or more target sequences. Moreover, solid phase methods may be adapted to machine-assisted protocols, thereby enabling automated or semi-automated methods to be carried out.

Representative embodiments of such methods relate to the solid phase synthesis of polyamides comprising seven or more units. For purposes of this illustrative description, all units are amino acids. However, this need not be so in each of these embodiments. Such embodiments are derived by modification of in situ neutralization methods described by Kent and coworkers (Schnolzer, et al., Int. *J. Peptide Protein Res., vol.* 40:180–193 (1992); Milton, et al. *Science, vol.* 252:1445–48 (1992)), and can be performed as described in U.S. Ser. No. 08/607,078.

To summarize, such methods preferably begin by obtaining or preparing a suitable solid support, for example, a polystyrene resin. Suitable supports include Boc-Py-PAM/BAM resins, Boc-Py-G-PAM/Boc-Py-$\beta$-PAM resins, and the corresponding Boc-Im resins. Preferably, the resin will contain a linker, and optionally a spacer, molecule that enables facile attachment and removal of the desired polyamide. If necessary for subsequent manipulations, the resin is then deprotected, for example, by washing it with dichloromethane followed by Boc group removal using 65% trifluoroacetic acid (TFA)/35% dichloromethane/0.5 M thiophenol for 20 min., followed by washing first with dichloromethane and then with dimethylformamide (DMF).

A protected and activated carboxy terminal amino acid (wherein the amino group is protected and the carboxylic group is activated, es., Boc-Py, Boc-Im-OBt, Fmoc-Py-Obt, Fmoc-Im-Obt, and particularly a Boc-protected allyl ester-Py monomer), or an intermediate amino acid polymer (e.g., an amino acid dimer or trimer), is then reacted with the activated amino functionality of the resin. Diisopropylethylamine is preferably present during the coupling reaction. The use of high concentrations of amino acids is preferred to enhance coupling reaction rates. After approximately 45 min., the resin is washed with DMF. When coupling amino-protected Py to the amino functionality of Im, it is preferable to use a Py monomer activated as a symmetric anhydride rather than an -OBt ester, using the protocol described by Ding, et. al., *Acta Chem. Scand., vol.* 23:751 (1963), as modified in U.S. Ser. No. 08/607,078.

Assembly of the polyamide is continued by the sequential addition of the remaining amino acids. After coupling of the final amino acid to the nascent polyamide, the amino group is deprotected. When an allyl group is present, it can be removed by a palladium catalyst. The polyamide can then be released from the resin by any suitable chemistry, e.g., by treatment with dimethylaminopropylamine.

Polyamides made in accordance herewith are preferably purified prior to use. RP-HPLC is a particularly preferred purification method. Irrespective of the purification method employed, purity levels exceeding about 90%, preferably above about 95%, and even more preferably above about 99%, are desirable.

II. Screening Methods

Another aspect of the present invention concerns methods of screening compounds made in accordance herewith (or any polyamide-alkylator conjugate) to identify one or more conjugates capable of binding to a selected target nucleotide sequence in a double-stranded nucleic acid (the screening substrate), particularly duplex DNA. Such methods involve combining one or more test compounds to be screened, or a mixture containing the test compound(s), in an appropriate assay system. Typically, the assay system employs a double-stranded nucleic acid containing one or more test sequences, i.e., the nucleotide sequence(s) with which one or more of the test compound(s) will hopefully interact, and one or more other substances (e.g., nucleic acids, polypeptides, small molecules, polysaccharides, etc.) each of which interacts with the same or a different specific nucleotide sequence in duplex nucleic acid molecules, i.e., the control sequence, which control sequence(s) are also present in the assay mixture. Moreover, as those in the art will appreciate, the test and control sequences can be the same, partially the same (e.g., overlapping by one or more base pairs), or different. When different, they may be separated by one or more base pairs, but are preferably juxtaposed, i.e., not overlapping and not separated by any nucleotide base pairs. Indeed, the test and control sequences can be present on different screening substrates.

Suitable test systems typically include a duplex nucleic acid molecule (preferably dsDNA) containing at least one test sequence, and preferably at least one control sequence. In those instances when a screening substrate comprises only a test sequence, and does not contain a screening sequence, or vice versa, the assay will also contain a second screening substrate containing the test or control sequence not found on the first screening substrate. The screening substrate(s) may contain one or more copies of the test and/or screening sequences.

The test sequence(s) can be obtained in a number of ways. For example, such sequences can be randomly generated (for example, by automated oligonucleotide synthesis) for a shotgun approach. Alternatively, one or more specific sequences (e.g., a specific promoter implicated in the manifestation of a particular disease) may be incorporated into the screening substrate.

Preferred control sequences for use in such assays include regulatory regions of disease-associated genes (e.g., genes implicated in cancer or autoimmune disease) and of genes of pathogens (e.g., viruses and eukaryotic and prokaryotic pathogens). In such instances, the binding substances employed will preferably be the proteins (or DNA binding domains thereof) known or suspected to interact with such sequences in vivo. Alternatively, the control sequence/binding substance used may be part of a well characterized protein/nucleic acid system, for example, the lac operator and repressor of *E. coli* or the $o_L$-$o_R$/cro repressor of phage lambda. Indeed, essentially any well characterized duplex nucleic acid/corresponding binding substance interaction can be readily adapted to the instant methods.

In preferred embodiments, the duplex nucleic acid-binding substance used in the assay system comprises a DNA binding protein (or portion thereof that interacts with dsDNA) that binds with high affinity (preferably with subnanomolar affinity) to a control sequence, e.g., the polypeptide's cognate binding site, in a manner that is preferably substantially independent of the sequences overlapping with or adjacent or juxtaposed to the control sequence. However, the polypeptide (or other duplex nucleic acid-binding substance) should be sensitive to high affinity binding (which, with respect to this aspect of the invention, means a substance with a $K_a$ of less than about 100 nM, preferably less than about 10 nM, particularly less than about 1 nM) of a compound to a test sequence, especially when the test sequence is the same as, overlapping with, or juxtaposed to (including being located on a separate screening substrate molecule) the control sequence.

To function properly, the duplex nucleic acid binding substance should be present in an amount that saturates the control sequence(s). For each assay, the test molecule is incubated in an assay mixture also containing the screening substrate(s) and binding substances for a period of time sufficient to permit equilibrium binding to be established between the test molecule(s), binding substance(s), and test and control sequences. The conditions under which such assays are performed are preferably in vitro conditions, although the instant methods can readily be adapted for application in cultured cells. Indeed, in preferred methods, test compounds identified in an in vitro assay as having the desired activity (e.g., subnanomolar binding affinity and the ability to substantially prevent, inhibit, or otherwise disrupt the interaction of a binding substance with its particular binding site on a screening substrate) are then subjected to screening in cultured cells to confirm their inhibitory activity on binding substance/duplex nucleic acid interactions. Those compounds exhibiting the desired activity profile are then typically for further studies, including those conducted in vivo.

Typically, in performing such screening assays the amount of binding substance bound to the control sequence of the screening substrate is compared before and after the addition of the test molecule or mixture. In preferred embodiments, comparison of a binding substance-bound to free dsDNA can be accomplished using a gel band-shift assay, filter-binding assay, or a capture/detection assay. Alternatively, indirect detection can be also be performed, for example, by comparing the activity of a restriction enzyme's cleavage of its cognate restriction site in the presence or absence of the test compound, or by examining the level of expression of a reporter gene (as may be detected at the nucleic acid or protein level, or by detection of some other signal, e.g., the amount of light generated by an assay system in which the gene, the expression of which is to be modulated, is luciferase.

Thus, screening methods according to the invention include those in which binding substance/duplex nucleic acid interactions are directly assayed (e.g., a gel shift assay), as well as those involving more indirect methods, e.g., detection of reporter gene expression. The methods of the invention may also be carried out on one or few test compounds or, alternatively, be performed on a high throughput basis, wherein 100–10,000 or more test compounds are screened against one or more test sequences. Such high throughput methods are particularly useful in conjunction with the solid state polyamide synthesis and conjugate synthesis methods described herein.

III. Compositions

The conjugates described herein can be administered to cells in vitro or in vivo. In addition, conjugates according to the invention can also be used in cell-free environments, for example, in experiments wherein cell extracts containing a fraction which contains double-stranded nucleic acid (e.g., a fraction containing nuclei, nuclear DNA, mitochondria, or miotochondrial DNA) or in experiments using dsDNA (e.g., duplexed oligonucleotides substantially complementary over at least a portion of their lengths, restriction fragments, plasmids, etc.). Thus, the intended application for a conjugate according to the invention will typically dictate the ultimate product composition, as those in the art will appreciate.

For example, wherein a conjugate according to the invention is to be used therapeutically (e.g., as an animal, particularly a human, medicine), it is formulated into an appropriate therapeutic composition. Similarly, if the conjugate is to be used in a diagnostic application, it will be incorporated into an appropriate composition for such application.

In its most simple form, a composition according to the invention may simply comprise a conjugate according to the invention, preferably as a salt. More typically, however, a composition according to the invention will comprise a conjugate and one or more other compounds. Such other compounds, or excipients, may or may not have independent or activity.

The term "pharmaceutically acceptable" or "pharmaceutical" as used herein refers to solutions or components of the pharmaceutical composition that do not prevent the therapeutic compound from exerting a therapeutic effect and do not cause unacceptable adverse side effects. For purposes of brevity, when used herein "pharmaceutical" shall be understood to include both human and other animal (e.g., domestic and other animal species, particularly those of agricultural importance) application. Examples of pharmaceutically acceptable reagents are provided in *The United States Pharmacopeia The National Formulary*, United States Pharmacopeial Convention, Inc., Rockville, Md. 1990 and *FDA Inactive Ingredient Guide* 1990, 1996 issued by the Division of Drug Information Resources (both are hereby incorporated by reference herein, including any drawings). Unacceptable side effects vary for different diseases or conditions to be treated or prevented. Generally, the severity of the disorder being treated will dictate the severity of the toxic effects that will be tolerated. Unacceptable side effects for different diseases are known in the art.

The term "physiologically acceptable" defines a carrier, diluent, or excipient that does not cause significant irritation to an organism and preferably does not abrogate the biological activity and properties of the compound or other active ingredients, if any.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water (or another solvent) that will dissolve the compound (s) of interest as well as stabilize the biologically active form of the compound(s) and other active ingredient(s), if present. Many salts dissolved in buffered solutions are utilized as diluents in the art. One commonly used buffered solution is phosphate buffered saline because it mimics the salt conditions of human blood. Because buffer salts can control the pH of a solution at low concentrations, a diluent rarely modifies the biological activity of a compound having biological activity.

The term "solvent" as used herein refers to a chemical that facilitates solubilization of a compounds according to the invention. Examples of solvents include, but are not limited to, pharmaceutically acceptable alcohols, such as ethanol, benzyl alcohol, and glycerol; polyoxyhydrocarbyl compounds (e.g., a water soluble carbohydrate such as glucose, sucrose, maltotriose, and the like; a water soluble carbohydrate derivative such as gluconic acid and mannitol, oligosaccharides; and water soluble polymers such as polyvinylpyrrolidone, polyvinyl alcohol, polyethers such as polyoxyalkylenes, including polyethylene glycol (PEG) and derivatives thereof, or other water soluble mixed oxyalkylene polymers and the polymeric form of ethylene glycol), pharmaceutically acceptable surfactants, and pharmaceutically acceptable oils.

The term "pharmaceutically acceptable surfactant" as used herein refers to a compound that can solubilize compounds of the invention into aqueous solutions, if necessary. Preferably for parenteral formulations, the surfactant is a non-ionic surfactant. A "pharmaceutically acceptable oil" is an oil such as mineral oil or vegetable oil and the like.

A. Formulation

For example, when a conjugate according to the invention is to be used to treat a human disease or disorder, it will typically be human patient per se, or in pharmaceutical compositions where they are mixed with other active ingredients, as in combination therapy, and/or one or more suitable carriers, excipient(s) (i.e., a more or less inert substance added to a composition to confer a suitable consistency or to enable a drug to be formed), adjuvants, stabilizers, and vehicles. The composition may be in solid, liquid, gel, or aerosol form. Techniques for formulation of the conjugates of the instant application may be found in "Remington's Pharmaceutical Sciences," Mack Publishing Co., Easton, Pa. (1995)

The pharmaceutical compositions of the present invention may be manufactured in a manner that is itself known, e.g., by means of conventional mixing, dissolving, granulating, dragee-making, levigating, emulsifying, encapsulating, entrapping, spray drying, or lyophilizing processes.

Proper formulation is dependent upon the route of administration chosen. For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the conjugates can be formulated readily by combining the active compound(s) with pharmaceutically acceptable carriers, excipients, etc. well known in the art. Such carriers excipients, etc. enable the compounds of the invention to be formulated as tablets, pills, dragees, capsules, liquids, gels, syrups, slurries, suspensions, and the like. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitoi; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. In certain non-human applications, such compositions may be included in food preparations.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active conjugate doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the conjugates for use according to the present invention are conveniently delivered in the form of powder, or more preferably, as an aerosol spray from a pressurized pack, nebulizer, or metered dose inhaler, with the use of a suitable propellant, e.g., dichlorodifluoromethane, trichlorofluoromethane, dichlorotetrafluoroethane, carbon dioxide, or other suitable gas.

Conjugates, can also be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions, emulsions in oily or aqueous vehicles, and lyophilized powders for reconstitution in an appropriate solution (e.g., sterile pyrogen-free water) prior to use, and may contain formulatory agents such as suspending, stabilizing, and/or dispersing agents.

In particular, pharmaceutical formulations for parenteral administration include aqueous solutions of the active compounds in water-soluble form. Additionally, suspensions of the active compounds may be prepared as appropriate oily injection suspensions. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In addition to the formulations described previously, the conjugates of the invention may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Other delivery systems for the pharmaceutical compositions compounds may also be employed. For example, liposomes and emulsions are well known examples of delivery vehicles or carriers for hydrophobic drugs. Use of delivery vehicles such as liposomes affords the opportunity to provide one or more targeting moieties in the composition, thereby enabling the conjugate to be delivered to a particular cell or tissue. Cell and tissue targeting techniques and moieties are known in the art, and will vary depending upon the particular application.

Additionally, conjugates may be delivered using a sustained-release system, such as semi-permeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the conjugate, additional strategies for protein stabilization may be employed.

For non-animal application, for example, to plants, the compositions of the invention will typically comprise the conjugate in a solution which can be sprayed on the plants or included in irrigation water. Alternatively, solid dosage forms that can be broadcast upon or near the targeted plant (or seeds) can also be prepared in accordance with methods known in the art.

Many of the conjugates of the invention may be provided as salts with pharmaceutically compatible counterions. Pharmaceutically compatible salts may be formed with many acids, including, but not limited to, hydrochloric, sulfuric, acetic, lactic, tartaric, malic, succinic, etc. acid. Salts tend to be more soluble in aqueous or other protonic solvents than are the corresponding free base forms.

IV. Administration

In a therapeutic or prophylactic context, the term "administering" relates to a method of incorporating or delivering a conjugate of the invention into cells or tissues of an organism, be it an animal or a plant. As those in the art will appreciate, depending upon application, administration can be either in vivo (i.e., to a living animal or plant) or in vitro (e.g., to cultured cells). With regard to in vivo administration to an animal (e.g., a human), many administration techniques exist, including, but not limited to, oral, parenteral (e.g. intravenous, intramuscular, subcutaneous, intraperitoneal, and intraarticular injection), and aerosol administration. The compounds may also be administered in a depot or sustained release formulation. For in vitro (including ex vivo) therapy, multiple administration techniques also exist, including cell microinjection techniques, simple diffusion, and carrier techniques.

To affect gene expression in a cell, which may include causing an increase or a decrease in the expression of one or more genes, an effective quantity of one or more conjugates is delivered to and internalized by the cell, be it in vivo or in vitro. Effective extracellular concentrations of polyamides that can modulate gene expression range from about 0.01 nanomolar (nM) to about 1 micromolar ($\mu$M), more preferably from about 0.1 nM to about 0.1 $\mu$M, particularly from about 1 nM to about 0.05 $\mu$M, especially about 10 nM to about 0.75 $\mu$M. Gottesfeld, et.al., Nature, vol. 387:202–205 (1997).

Notwithstanding the foregoing, those in the art will appreciate that, with regard to therapeutic or prophylactic treatment, the selection of the precise concentration, composition, and delivery regimen will be influenced by, inter alia, the specific pharmacological properties of the particular composition, the intended use, the nature and severity of the condition being treated or prevented, the age, weight, gender, and physical condition of the intended recipient, as well as the route of administration. Such considerations are within the purview of the skilled artisan. For example, to determine effective amounts and concentrations of conjugates in vitro, a suitable number of cells is plated on tissue culture plates and various quantities of one or more conjugates are added to separate wells. Expression of the particular gene(s) whose expression is(are) to be modulated following exposure to the compound can be monitored in the cells or medium by detecting the amount of the protein gene product present as determined by various techniques utilizing specific antibodies, including ELISA and Western blotting. Alternatively, gene expression following exposure to a polyamide can be monitored by detecting the amount of messenger RNA present, as determined by various techniques, including Northern blotting and RT-PCR.

Similarly, to determine effective amounts and concentrations of conjugates for in vivo administration, a sample of body tissue or fluid, such as plasma, blood, urine, cerebrospinal fluid, saliva, or biopsy of skin, muscle, liver, brain or other appropriate tissue source, can be analyzed. Gene expression following exposure to a polyamide can be monitored by detecting the amount of the protein gene product present as determined by various techniques utilizing specific antibodies, including ELISA and Western blotting. Alternatively, gene expression following exposure to the compound can be monitored by the detecting the amount of messenger RNA present as determined by various techniques, including northern blot and RT-PCR. Such determinations can also be made by these and others techniques applied to cells from an organism of the type to be treated (or an animal model therefore) before and after administration of a composition according to the invention. These and other strategies known in the art can be readily adapted to a given application for a particular conjugate.

V. Applications

A. Modulation of Gene Expression

The conjugates described herein are useful for modulating expression of one or more genes in vitro or in vivo. Such modulation is typically accomplished by delivering a quantity of a conjugate according to the invention sufficient to interact with a specific nucleotide sequence present in double-stranded nucleic acid (e.g., dsDNA), preferably a regulatory sequence, and cause a change in expression of a gene functionally associated with such regulatory sequence. Such sequences include promoters, enhancers, repressor binding sites, and any other nucleotide sequence targeted by a DNA binding protein or other substance in a cell that can affect transcription. Cellular events involved in transcription include nucleosome formation and dissociation, formation of RNA transcription complexes, transcription initiation, etc.

Genes the expression of which can be modulated in accordance with this invention include cellular or viral genes. Such cellular genes include both eukaryotic and prokaryotic genes. The cellular gene(s) can be present in original, native cells, in cells transfected or transformed with a recombinant DNA construct comprising the cellular gene, or in an in vitro, cell-free system, for example, as a reporter gene. Similarly, a viral gene can be present in a cell or in an in vitro, cell-free system.

The conjugates of the present invention can act as specific inhibitors or activators of gene transcription in vivo or in vitro as therapeutic or prophylactic agents in treating disease conditions related to the transcription of at least one cellular or viral gene.

Certain embodiments of the present invention concern the use of a unique or rare sequence adjacent to or overlapping with the binding sites for common transcription factors as the target sequences for the design of conjugates. It has been found that sequences adjacent to the binding sites for required transcription factors are unique, i.e., are not associated with genes in the current publicly available nucleic acid databases.

Many protein coding genes utilize both gene- and tissue-specific transcription factors as well as general transcription factors for transcription of mRNA by RNA polymerase II. The binding sites for these protein factors are found in numerous genes, whereas the sequences adjacent to or overlapping with these binding sites tend to be unique for each gene. Conjugates can be designed which target sequences adjacent to or overlapping with the binding sites for these transcription factors, as well as to the binding sequences for these factors. Conjugates that target these sequences will interfere with the binding of the protein factors to DNA and thereby inhibit transcription by RNA Polymerase II.

In other embodiments, conjugates can be designed and synthesized that recognize and bind the sequences immediately adjacent to, or overlapping with, the site at which the minor groove-binding protein TATA-box binding protein (TBB) binds to TATA DNA can be designed. DNA sequences adjacent to or overlapping with TATA elements are gene-specific, whereas TATA elements are found in many protein-coding genes. For example, a hairpin polyamide bound to a sequence adjacent to the HIV-1 TATA element has been shown to inhibit HIV-1 promoter-specific transcription by RNA polymerase II. A conjugate designed to selectively bind this site would be useful to treating diseases associated with HIV-1 infection.

In other embodiments, the conjugates will recognize and bind to an identified target sequence adjacent to the transcription factor protein binding site of a cellular gene, for example, a constitutively expressed gene under basal transcription control (e.g., the gene encoding the 5S ribosomal subunit).

In yet other preferred embodiments, the minor groove transcription factor protein of the cellular gene is TBP. Such preferred cellular genes include oncogenes such as LEF-1, Ets-1 and her-2/neu. Other such preferred cellular genes include genes encoding cytokines such as interleukins, including IL-2, IL-5 and IL-13, tumor necrosis factors, including TNF-alpha and TNF-beta, growth factors, including TGF-beta, and colony stimulating factors, including GM-CSF.

Using the above described rules, a sequence-specific conjugate can be designed that selectively binds to an identified target site adjacent to the binding site of a DNA binding protein, e.g., transcription factor. As used herein, "adjacent" includes conjugate binding sites wherein an end nucleotide base pair of the binding site is immediately contiguous to an end nucleotide of the DNA binding protein binding site, and conjugate binding sites separated from the protein binding site by from one to about 20, preferably from 1 to about 10 or fewer intervening nucleotide base pairs. The binding affinity of such a designed conjugate should be greater than the binding affinity of the native transcriptional element in order to inhibit transcription. The binding affinity can be ascertained by competitive inhibition experiments against a native transcription factor. "Overlapping" refers to a conjugate binding site wherein one to five nucleotide base pairs of the compound's binding site are shared with the binding site of the DNA binding protein.

A "promoter" is a regulatory sequence of dsDNA involved in the binding of RNA polymerase to initiate transcription of a gene. A "gene" is a segment of DNA which codes for a "gene product", typically a peptide, polypeptide, or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code, and other signals, such as polyadenylation signals. "Gene products" also include RNA molecules, for example, tRNAs, small nuclear RNAs, ribosomal RNAs, and catalytic RNAs (e.g., ribozymes). A "gene of interest" refers to a gene the expression of which is desired to be modulated using a conjugate according to the invention.

Promoters are often upstream ("5' to") the transcription initiation site of the corresponding gene. Other regulatory sequences of DNA in addition to promoters are known, including sequences involved with the binding of transcription factors, including response elements that are the DNA sequences bound by inducible factors. "Enhancers" comprise yet another group of regulatory sequences of DNA that can increase the utilization of promoters, and can function in either orientation (5'→3' or 3'→5') and in any location (upstream or downstream) relative to the promoter. In some embodiments, the regulatory sequence has a positive activity, i.e., binding of an endogenous ligand (e.g., a transcription factor) to the regulatory sequence increases transcription, thereby resulting in increased expression of the corresponding target gene. In such a case, interference with transcription by binding a polyamide to a regulatory sequence would reduce or abolish expression of a gene.

A promoter can also include or be adjacent to a regulatory sequence known in the art as a "silencer". A silencer generally has a negative regulatory effect on expression of the gene. In such cases, expression of a gene may be increased (also referred to as gene "activation" or "derepression") directly by using a conjugate according to the invention, e.g., a polyamide, to prevent binding of a factor to a silencer regulatory sequence, or indirectly by using such a compound to block transcription of a factor that interacts with a silencer.

To affect gene expression in a cell, which may include causing an increase or a decrease in gene expression, a quantity of one or more conjugates effective to modulate transcription is contacted with the cell and internalized by the cell. The cell may be contacted by the polyamide in vivo or in vitro. Effective transcription inhibiting extracellular concentrations of polyamides that can module gene expression range from about 10 nanomolar to about 1 micromolar. Gottesfeld, J. M., et al., *Nature* 387:202–205 (1997). To determine effective amounts and concentrations of polyamides in vitro, a suitable number of cells is plated on tissue culture plates and various quantities of one or more polyamides are added to separate wells. Gene expression following exposure to a conjugate can be monitored in the cells or in the medium by detecting the amount of the protein gene product present as determined by various techniques utilizing specific antibodies, including ELISA and Western blot. Alternatively, gene expression following exposure to a conjugate can be monitored by detecting the amount of messenger RNA present as determined by various techniques, including Northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a conjugate can be monitored by detecting the amount of the protein gene product present as determined by various techniques utilizing specific antibodies, including ELISA and Western blot. Alternatively, gene expression following exposure to a conjugate can be monitored by detecting the amount of messenger RNA present as determined by various techniques, including Northern blot and RT-PCR.

1. Inhibition

The present invention provides conjugates, which inhibit the transcription of DNA upstream or downstream of transcriptional factors such as the 5S RNA gene transcriptional factor TFIIIA, the minor groove-binding protein TATA-box binding protein (TBP), Ets-1, and LEF-1. Such compounds can act as gene-specific inhibitors of transcription since they are selective for the sequences flanking these protein binding sites that are, in turn, gene-specific.

2. Activation

In addition to being useful to inhibit gene transcription, the conjugates according to the invention can also be used to activate transcription of one or more genes. Such activation will typically involve interference with, or inhibition of, binding of a repressor protein or a similar molecule to a specific regulatory region of the gene of interest. Accordingly, the methods used to design and synthesize conjugates, to inhibit gene transcription can similarly be applied in the context of activation of a gene of interest.

A. Treatment/Prophylaxis

As will be clear to those in the art, the conjugates described herein can be used to treat or prevent a variety of diseases and other conditions associated with the expression of one or more genes, and will thus have many applications, including. anti-viral, anti-bacterial, anti-fungal, and anti-cancer applications.

In the treatment context, an appropriate amount of a conjugates according to the invention will be administered to an organism known to have, or suspected of having, a particular disease or disorder. In addition, conjugates can be used prophylactically to prevent the development of an unwanted disease or disorder by preventing undesirable gene expression. In either context, the conjugates will be administered in accordance with the teachings provided herein.

A representative example of how conjugates according to the invention can be used in a therapeutic context concerns HIV. A recent review summarizes current knowledge of the protein factors required for the control of RNA initiation and elongation by RNA polymerase II at the HIV-1 promoter (Jones, K. A. and B. M. Peterlin. 1994. Control of RNA initiation and elongation at the HIV-1 promoter. *Annu. Rev. Biochem.*, 63:717–743). For HIV, the template for synthesis of both new viral RNA and messenger RNA (for viral protein synthesis) is the integrated provirus. HIV-1 utilizes the transcription machinery of the host cell but encodes its own trans-activators, Tat and Rev, that are responsible for RNA elongation and utilization.

The HIV-1 promoter is located in the U3 region of the leftward (5') long terminal repeat. The core promoter and enhancer elements span a region of approximately 250 base pairs and include TTA and initiator elements ad the binding sites for the following cellular transcription factors: Sp1, NF-κB, LEF-1, Ets-1 and USF. Sequences upstream of the NF-κB sites contribute only marginally to HIV-1 promoter activity enter in vitro or in transfected cell lymphoid cell lines. Waterman, M. L. and K. A. Jones, *New Biologist*, 2:621–636 (1990). However, these upstream sequences, and presumably the protein factors which bind these upstream sequences, are important for viral replication, and hence promoter activity, in peripheral blood lymphocytes and in some T cell lines. Kim, J., et al., *J. Virol*, 67:1658–1662 (1993).

Two of the binding sites in the upstream region correspond to recognition sites for activator proteins that are lymphoid cell specific (or highly enriched in T cells) and are shared with the promoter of the T cell receptor (TCRα) gene: these are the Ets-1 and LEF-1 transcription factors. The essential role of the upstream region has been reproduced in vitro (Sheridan, P. L., et al., *Genes Dev.*, 9:2090–2104 (1995)). LEF-1 and Ets-1 are believed to act in concert to prevent nucleosome-mediated repression in vivo. Inhibition of formation of this complex may represent a viable target for HIV-1 therapy. LEF-1 belongs to the HMG family of proteins and binds DNA as a monomer in the minor groove, resulting in a large distortion of the DNA helix (unwinding and bending) (Love, J. J., et al., *Nature*, 376:791–795 (1995)).

In addition, LEF-1 possesses a strong trans-activation domain that retains its function when engineering into other DNA-binding proteins (Giese, K., et al., *Genes Dev.*, 9:995–1008 (1995)).

The HIV-1 promoter also contains tandem binding sites for NF-κB, a factor that is strongly induced by HIV infection (Bachelerie, F., et al., *Nature*, 350:709–712 (1991)), and multiple binding sites for the general transcription factor Sp1. NF-κB contacts both Sp1 and the TBP subunit of the basal transcription factor TFIID. Perkins, N. D., et al., *Mol. Cell. Biol.*, 14:6570–6583 (1994). Additionally, Sp1 has been shown to interact with the TAFL110 subunit of TFIID (110 kDa TBP-associated factor) (Chen, J. L., et al., *Cell*, 79:93–105, 1994). The binding of TFIID via the TBP interaction with the TATA element nucleates the assembly of the complete RNA polymerase II transcription complex (reviewed in Maldonado, E. and D. Reinberg, *Current Opinion in Cell Biology*, 7:352–361, 1995). Thus, NF-κB may function through recruitment of Sp1 and TFIID to the HIV-1 promoter via these protein-protein interactions. Accordingly, blocking the NF-κB-DNA and/or Sp1-DNA interaction is another target for HIV therapy.

Since these factors, and especially Sp1 and TFIID, are utilized for the expression of a wide range of cellular genes, the binding sites for these factors are not ideal targets for HIV-specific inhibition (or any gene-specific inhibition). However, the sequences adjacent to these sites that are unique to HIV-1 proviral DNA are excellent candidate targets for the design of inhibitory conjugates.

Organisms suitable for administration of conjugates according to the invention include any plant or animal containing, or suspected to contain, a gene the expression of which would be desirable to modulate. Preferred animals include mammalian, fish, and avian species. Particularly preferred mammals include humans and bovine, canine, equine, feline, ovine, and porcine animals. Particularly preferred avian and fish species are those of commercial or ecological significance. Preferred plants include commercially or ecologically significant trees, grains, grasses, and cereals.

B. Diagnostics

Conjugates according to the present invention are also useful for detecting the presence of double-stranded nucleic acid, particularly dsDNA, containing a specific sequence of nucleotide base pairs for diagnostic or preparative purposes. For example, a sample containing dsDNA can be contacted by a sequence-specific conjugate linked to a solid substrate, thus enabling isolation of dsDNA comprising the desired sequence. Alternatively, conjugates linked to a suitable detectable marker, such as biotin, a hapten, a radioisotope, or a dye molecule, can be contacted by a sample containing dsDNA suspected to contain the desired target nucleotide base pair sequence. Such bifunctional compounds complexed to dsDNA can then be detected using an appropriate detection system known to those skilled in the art. For example, DNA associated with a conjugate linked to biotin can be detected by a streptavidin/alkaline phosphatase system.

Other diagnostic applications the conjugate according to the invention include double-stranded nucleic acid, particularly dsDNA, sequencing on a solid support comprising a plurality of conjugates specific for different nucleotide base pair sequences.

The present invention also provides diagnostic systems, preferably in kit form, comprising conjugates according to the invention. Representative embodiments of such systems include kits for assaying for the presence in a cell or tissue sample of a dsDNA sequence bound by a particular conjugate according to the invention. Such systems include, in an amount sufficient to perform at least one assay, one or more specific conjugates according to the invention as a separately packaged reagent. Instructions for use of the packaged reagent(s) are also typically included. As used herein, the term "package" refers to a solid matrix or material such as glass, plastic (e.g., polyethylene, polypropylene, or polycarbonate), paper, foil, and the like capable of holding within fixed limits such conjugate(s). Thus, for example, a package can be a glass vial used to contain milligram quantities of a contemplated conjugate, a microliter plate well to which microgram quantities of a contemplated conjugate have been operatively affixed, i.e., linked so as to be capable of being bound by the target sequence in dsDNA, or a glass slide to which a plurality (i.e., more than one, and to 100,00 or more) of such conjugates are operatively affixed, as may be the case in certain nucleic acid sequencing methods using the instant conjugates. When necessary, such diagnostic systems preferably also include a detectable label or other indicator capable of signaling the binding of the contemplated conjugate to its target sequence. As noted above, numerous detectable labels, such as biotin, and other indicators, such as enzyme-linked (direct or indirect) streptavidin, are well known in the art.

C. Research Reagents

The conjugates described herein will also find utility as research reagents. For example, administration of such compounds to cultured cells will enable the production of cells having desired phenotypes. Such phenotypes may be useful for a variety of purposes, including the study of the effects of other compounds on the expression levels of one or more genes. Alternatively, conjugates according to the invention can also be used to produce "knock-out" mutations wherein actual changes at the genetic level are unnecessary.

Conjugates according to the invention will also find use in in vitro research applications. For example, addition of a conjugates that inhibits binding of a restriction enzyme to its cognate restriction site will prevent cleavage of a particular DNA containing such restriction site. In another example, in vitro transcription systems can be regulated by the addition of one or more appropriate conjugates.

V. Sequence Specific Covalent Attachment in the DNA Minor Groove by Small Molecules In order to inhibit gene expression when bound to the coding region of genes, and in order to inhibit elongation by the RNA polymerase enzymes, we have used a high affinity class of DNA binders and designed and made bifunctional molecules which covalently attach to predetermined sequences in the minor groove of DNA. Thus, the present invention provides hairpin polyamides with separate domains for DNA binding and DNA covalent attachment as new research tools for the field of functional genomics.

A. Hairpin polyamide-bis(dichloroethylamino)benzene conjugates

Nitrogen mustards are well characterized DNA alkylators with little sequence specificity. Baird, E. E. & Dervan, P. B. (1996), *J. Am. Chem. Soc.* 118, 6141–6146. A freely diffusing bis(dichloroethylamino)benzene moiety such as chlorambucil reacts with the more nucleophilic N7 of guanine in the major groove, but will alkylate the N3 of adenine in the minor groove when attached to minor groove DNA binding ligands. Zhi-Fu, T., Fujiwara, T., Saito, I. & Sugiyama, H. (1999), *J. Am. Chem. Soc.* 121, 4961–4967; and Baraldi, P. G., Cacciari, B., Guiotto, A., Romagnoli, R., Zaid, A. N. & Spalluto, G. (1998), *Current Pharmaceutical Design* 4, 249–276.

The combination of subnanomolar binding hairpin polyamides and bis(dichloroethylamino)benzene derivatives creates a class of bifunctional agents that bind to predetermined DNA sequences with high affinity and specificity for subsequent covalent reactions at N3 of adenine. Key design issues are sites of attachment of the functional domains and the choice of linker length and flexibility. In order to target the adenines adjacent to polyamide binding sites, we chose to attach bis(dichloroethylamino)benzene derivatives to the chiral α-amino group on the γ-turn of a pyrrole/imidazole hairpin polyamide.

Polyamide 1 has been shown to bind the sequence 5'-WGCWGCW-3' adjacent to both sides of the TATA box in the HIV promoter with high affinity ($K_a=2.0\times10^{10}$ $M^{-1}$). Gottesfeld, J. M., Neely, L., Trauger, J. W., Baird, E. E. & Dervan, P. B. (1997). Nature 387, 202–205. Substitutions at the α position of the γ-turn using (R)-2,4-diaminobutyric acid potentially have only a modest effect on DNA binding affinity or specificity. Herman, D. M., Baird, E. E. & Dervan, P. B. (1998). J. Am. Chem. Soc. 120, 1382–1391. We chose this as the point of attachment of a nondiffusible electrophile which would react at the N3 of adenine adjacent to the polyamide binding site The reagent chlorambucil (CHL), 4-[bis(2-chloroethyl) amino]benzene butanoic acid, contains a simple flexible linker and this proved adequate for the initial design-synthesis effort. Since alkylation by the electrophile results in irreversible binding, a non-alkylating conjugate 3 in which the chlorides have been replaced with hydroxyls was also synthesized as a control to investigate energetic penalty (or lack thereof) on polyamide binding affinity and specificity for the target sequence. In addition compound 4 will serve as a control to compare alkylation of the alkylating moiety unlinked to a polyamide.

Here, we provide hairpin polyamides which selectively alkylate and cleave DNA in the minor groove. Alkylation adducts and cleavage yields were determined using thermal cleavage assays on a 241 base pair restriction fragment and 120 base pair synthetic oligonucleotides. DNA binding affinity and specificity were determined by DNase I footprinting of the non-reactive conjugate 3.

B. Synthesis of Conjugates

Figure 4:
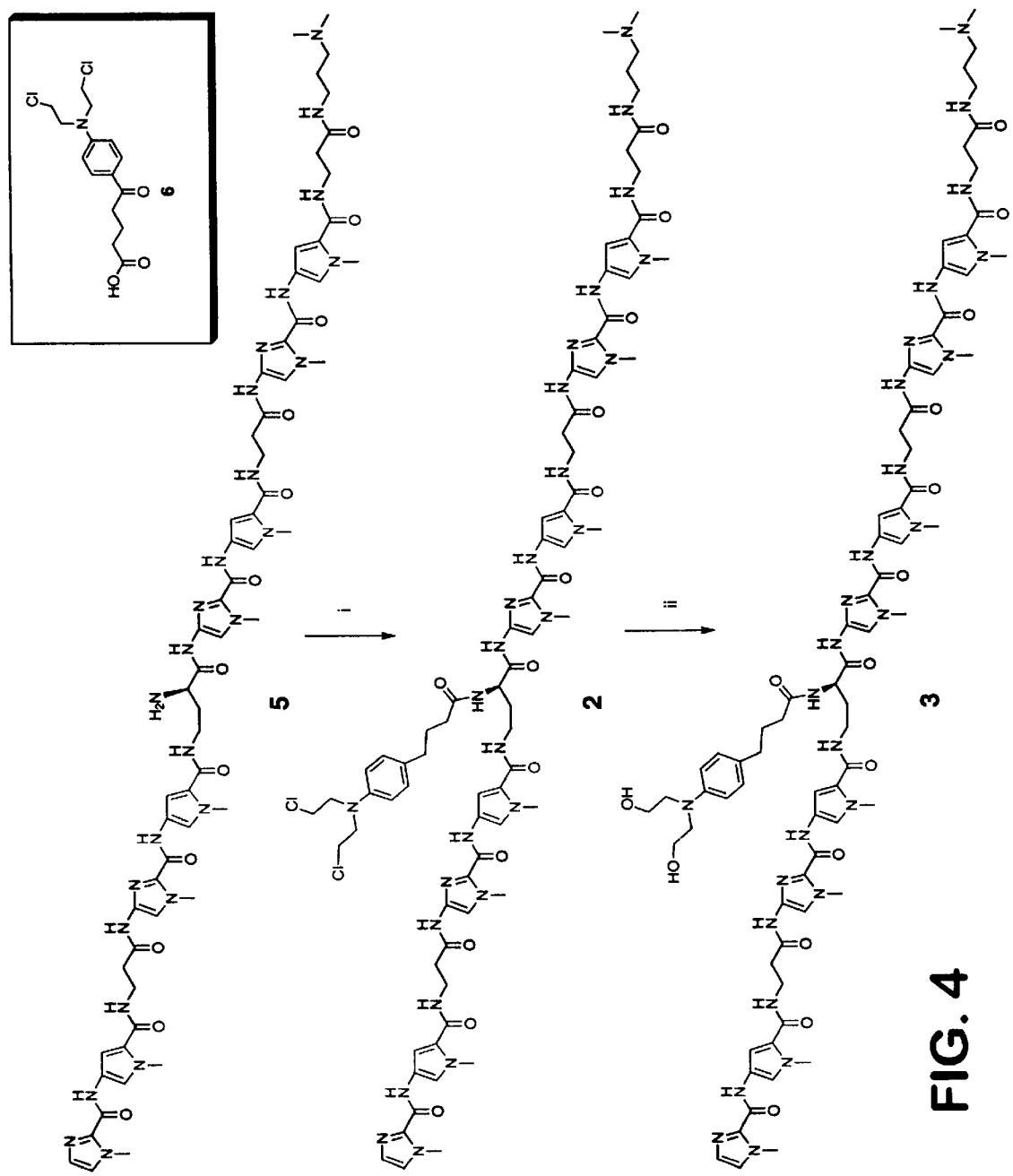
FIG. 4 shows the synthetic scheme for preparation of polyamide conjugate, ImPy-β-ImPy-(R)$^{CHL}$γ-ImPy-β-ImPy-β-Dp (2). The HOBt-activated nitrogen mustard 6 is coupled with standard DCC/HOBt activation to polyamide 5 and purified by reverse phase HPLC (step i). The hydrolyzed conjugate 3 is prepared by addition of 0.1 M NaOH (step ii).

Polyamide 5, ImPy-β-ImPy-(R)$^{H_2N}$γ-ImPy-β-ImPy-β-Dp, was prepared by manual solid phase polyamide synthesis. Reynolds, V. L., Molineux, I. J., Kaplan, D. J., Swenson, D. H. & Hurley, L. H. (1985), Biochemistry 24, 6228–6237. After purification by reverse phase high performance liquid chromatography (HPLC), the appropriate activated carboxylate derivative of bis(dichloroethylamino)benzene was coupled to the α-amino group on the γ-turn, using standard DCC/HOBt conditions, to yield polyamide-nitrogen mustard conjugates 2 (FIG. 4). Control conjugate 3 was synthesized by allowing 2 to react with 0.1 M NaOH, followed by neutralization and lyophilization. Control compound 4 was synthesized by coupling chlorambucil to (dimethylamino)-propylamine (Dp). All compounds were purified by reverse phase HPLC. MALDI-TOF mass spectrometry analysis of each compound was consistent with the calculated mass of the compounds.

VI. Polyamide Binding Affinity and Specificity is Unaltered by Substitution

Figure 5A:
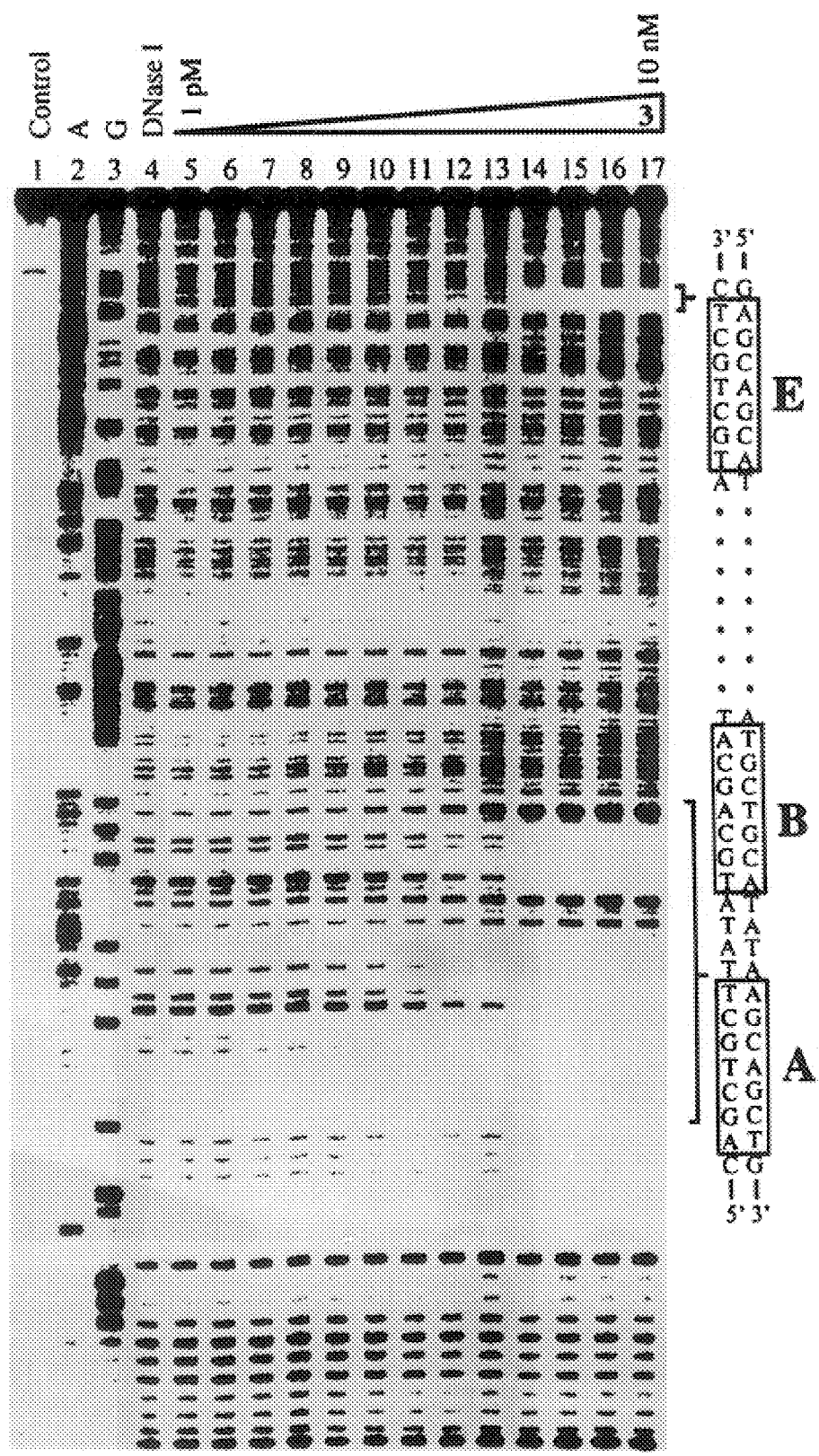
FIG. 5(a) shows the results of quantitative DNase I footprint titration experiments with ImPy-β-ImPy-(R)$^{CHL(OH)}$γ-ImPy-βImPy-β-Dp (3) on the 3'-$^{32}$P-end-labeled 241 base pair EcoRI/HindIII restriction fragment from plasmid pHIV-LTR. Jones, K. A. & Peterlin, B. M. (1994), *Annual Review of Biochemistry* 63, 717–743. Left, storage phosphor autodiograms of 8% denaturing polyacrylamide gels used to separate the fragments generated by DNase I digestion. All reactions contained 20,000 cpm restriction fragment, 10 mM Tris.HCl (pH 7.0), 10 mM KCl, 10 MM MgCl$_2$ and 5 mM CaCl and were performed at 22° C. Lane 1, intact DNA; lane 2, A-specific reaction; lane 3, G-specific reaction; lane 4, DNase I standard; lanes 5–17, 1 pM, 2 pM, 5 pM, 10 pM, 20 pM, 50 pM, 100 pM, 200 pM, 500 pM, 1 nM, 2 nM, 5 nM, 10 nM, respectively. The 5'-AGCTGCT-3' (A), 5'-TGCAGCA-3' (B), and 5'-TGCTGCT-3' (E) match sites are shown in boxes on the right side of the autoradiogram (SEQ ID NO:4).
Figure 5B:
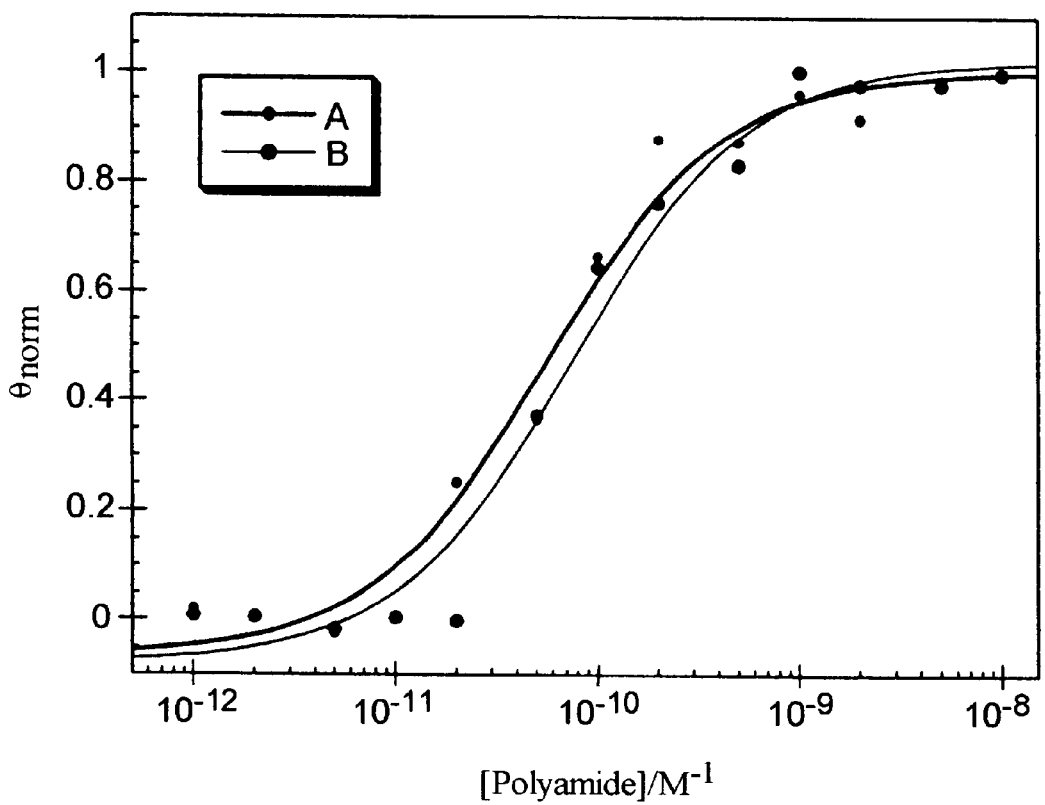
FIG. 5(b) depicts data from quantitative DNase I footprint titration experiments for ImPy-β-ImPy-(R)$^{CHL(OH)}$γ-ImPy-βImPy-β-Dp (3) binding to the 5'-AGCTGCT-3' (A) and 5'-TGCAGCA-3' sites (B). θ$_{norm}$ points were obtained using storage phosphor autoradiography and processed as described in the experimental section The data for the binding of 3 to 5'-AGCTGCT-3' is indicated by red circles and binding to 5'-TGCAGCA-3' by blue circles. The solid curves are best-fit Langmuir binding titration isotherms obtained from a nonlinear least-squares algorithm eq 2 (n=1).

Quantitative DNase I footprint titration experiments were performed on compound 3 to measure the equilibrium association constant for the match binding sites (5'-WGCWGCW-3') on a 241 bp restriction fragment derived from the HIV-1 promoter region (FIG. 5) (SEQ ID NO:4). The conjugate binds the match sites 5'-AGCTGCT-3' and 5'-TGCAGCA-3' with equilibrium association constants of $K_a=1.6\pm0.7\times10^{10}$ $M^{-1}$ and $1.3\pm0.7\times10^{10}$ $M^{-1}$, respectively. The binding affinity of unsubstituted polyamide 1 is $K_a=2.0\times10^{10}$ $M^{-1}$. Dickinson, L. A., et al. (1998), *Proc. Natl. Acad. Sci. U.S.A.* 95, 12890–12895. Affinities for the double base pair mismatch sites, 5'-TGTCGCC-3' and 5'-AGCAGCTC-3', were determined to be >100 fold lower that the for the match sites. Attachment of the benzene moiety to the γ turn does not appear to affect the DNA binding affinity or specificity of the polyamide.

VII. DNA Alkylation by Polyamide Conjugate Proceeds in High Yield

Figure 6A:
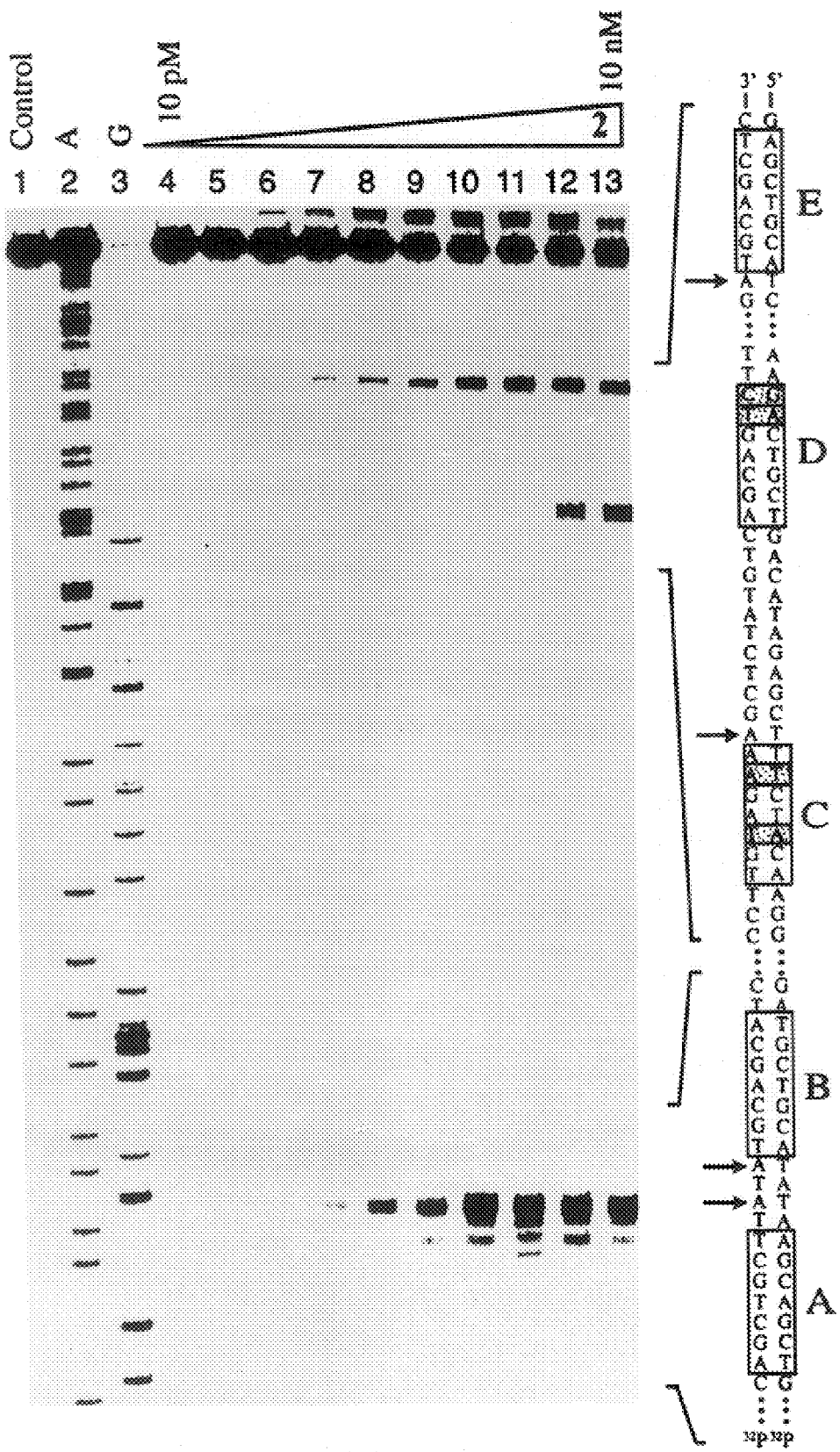
FIG. 6 shows the results of thermal cleavage assay experiments with ImPy-β-ImPy-(R)$^{CHL}$γ-ImPy-β-ImPy-β-Dp (4) on the 5'and 3'-$^{32}$P-end-labeled 241 base pair EcoRI/HindII restriction fragment from plasmid pHIV-LTR [Jones, K. A. & Peterlin, B. M. (1994), *Annual Review of Biochemistry* 63, 717–743]. Storage phosphor autodiograms of 8% denaturing polyacrylamide gels used to separate the fragments generated by heat induced DNA cleavage at alkylation sites. All reactions contained 10,000 cpm restriction fragment, 10 mM Tris.HCl (pH 7.0), 10 mM KCl, 10 mM MgCl and 5 mM CaCl and were performed at 37° C. Following 24 hour of equilibration, the DNA pellet was resuspended in sodium citrate buffer (pH=7.2) and heated to 90° C. for 15 min to thermally cleave at sites of adenine- or guanine-N3 lesions. (a) 5'-$^{32}$P-end-labeled restriction fragment (SEQ ID NO:5). (b) 3'-$^{32}$P-end-labeled restriction fragment. (a–b) Lane 1, intact DNA; lane 2, A-specific reaction; lane 3, G-specific reaction; lanes 5–13, 10 pM, 20 pM, 50 pM, 100 pM, 200 pM, 500 pM, 1 nM, 2 nM, 5 nM, 10 nM, respectively. (b) Lane 14, 10 µM CHL-Dp (5). Center, alkylation sites on the DNA fragment, indicate by arrows. Sites 5'-TCGTCGACGA-3' (SEQ ID NO:20) (A), 5'-ACGTCGA-3' (B), and 5'-ACGTCGA-3' (E) are match sites and 5'-ACATCTT-3' (C) and 5'-TCGTCAG-3' (D) are double base pair mismatches (mismatches indicated by gray boxes).
Figure 6B:
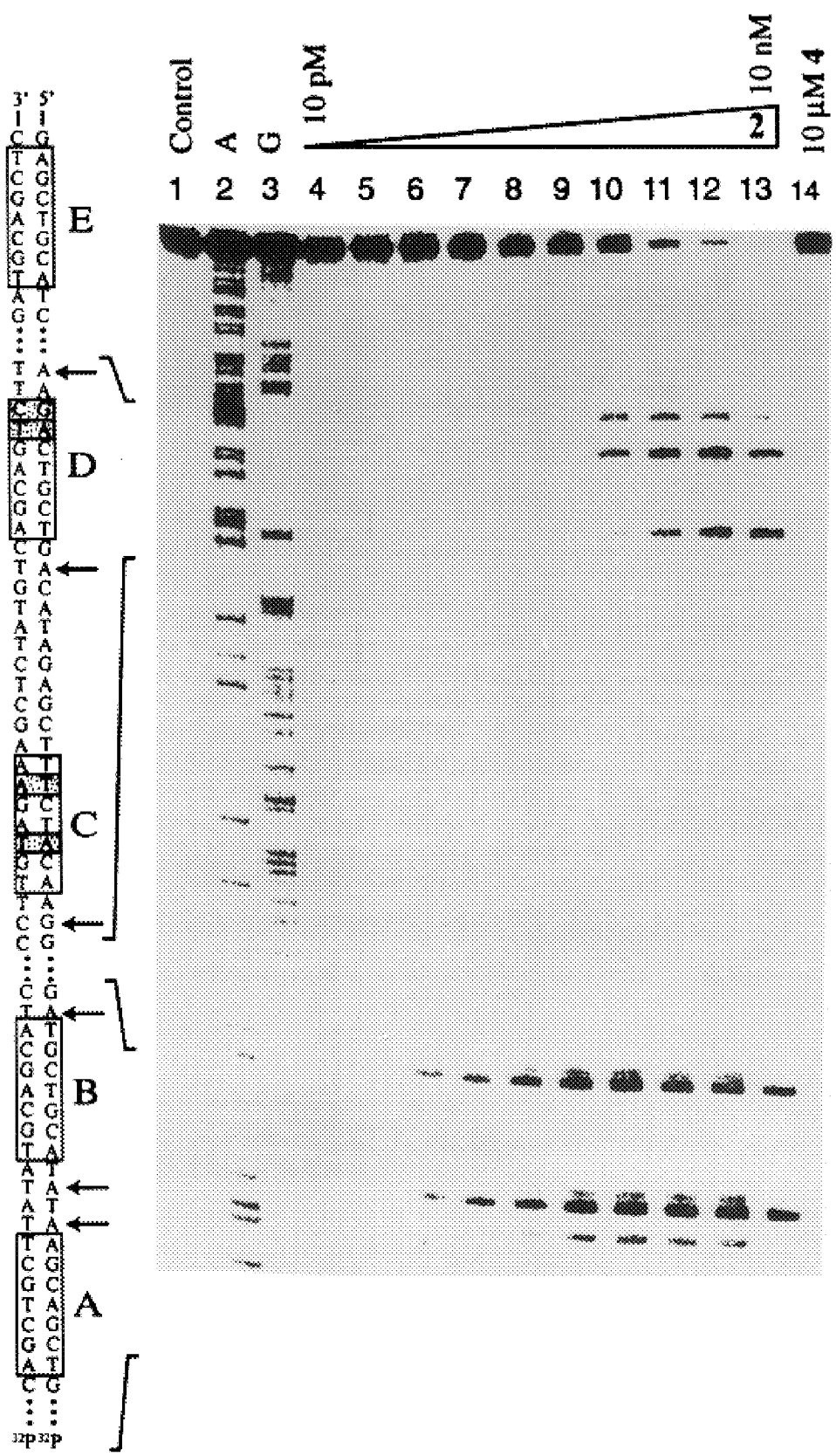

In order to measure DNA cleavage, thermal cleavage assays were performed on 3' and 5' $^{32}$P labeled 241 base pair, restriction fragments containing the HIV-1 promoter (FIG. 6) (SEQ ID NO:5) Reynolds, V. L., et. al., (1985), *Biochemistry* 24, 6228–6237. Alkylation in high yield was observed at subnanomolar concentrations for conjugate 2. In fact quantitative cleavage by conjugate 2 at 10 nM concentration was observed on one strand (bottom strand, FIG. 2) (SEQ ID NO:2). In contrast, no cleavage was observed at 10 μM concentration of the freely diffusing chlorambucil-(dimethylamino) propylamine derivative 4.

Figure 7A:
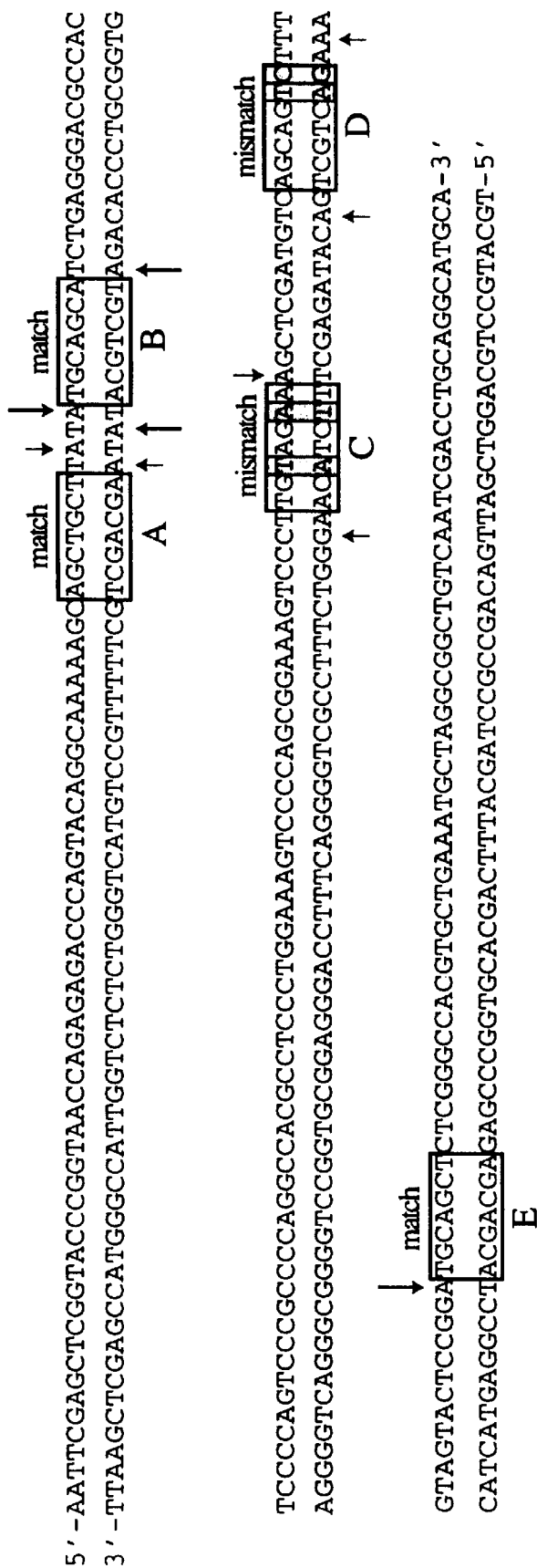
FIG. 7(a) shows the sequence of the 241 bp pHIV-LTR Eco RI/Hind III restriction fragment (SEQ ID NO:5). The five binding sites are indicated by boxes. Base pair mismatches are indicated by gray boxes. Cleavage sites of adenine- or guanine-N3 lesions at 10 nM are indicated by arrows. Large and small arrows indicate major and minor alkylation sites, respectively.
Figure 7B:
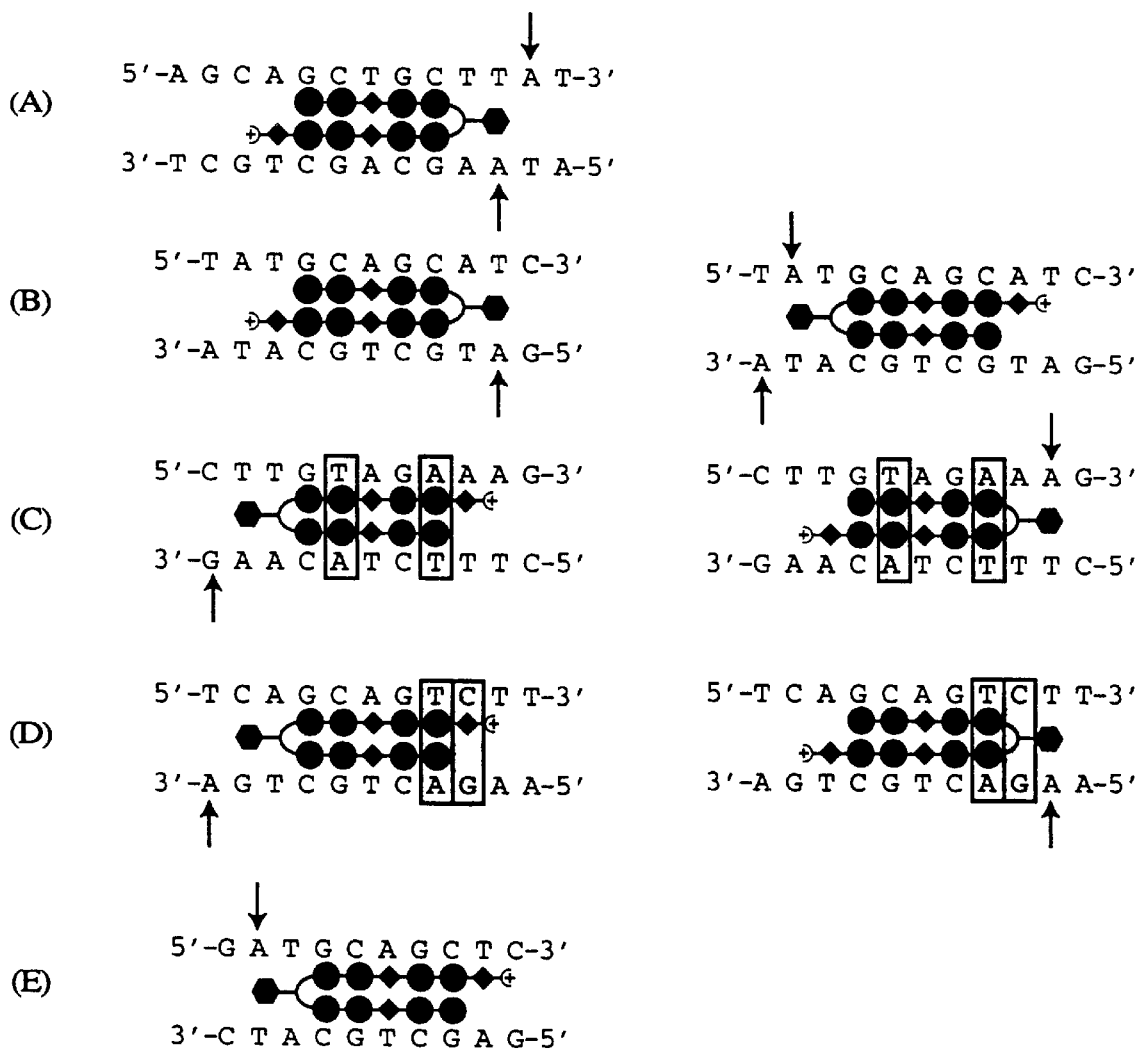
FIG. 7(b) shows binding models for alkylation are shown (SEQ ID NOS:7–11). Models are colored as in FIG. 1. Base pair mismatches are indicated by yellow boxes.

VIII. Polyamide Conjugate Specifically Alkylates Adenines Adjacent to Binding Sites Upon heat induced cleavage, all alkylation sites observed for conjugate 2 at subnanomolar concentrations were adjacent to target polyamide binding sites (FIG. 7) (SEQ ID NO:6). Due to the symmetry of the 5'-WGCWGCW-3' binding site, the polyamide binds in two orientations, alkylating adenine residues adjacent on either side of the polyamide binding site (FIG. 7b) (SEQ ID NOS:7–11). At concentrations greater than 1 nM, minor cleavage was observed proximal to double base pair mismatch sites as well. Specificity for reaction at match sites over mismatch sites is approximately 20 fold.

For the thermal cleavage assays, alkylation of adenine was observed at all but one interesting exception. The exception was cleavage of guanine at one of the mismatch sites. Reaction at N3 of guanines has previously been observed with tallimustine, a Py$_3$ conjugate with a bis (dichloroethylamino)benzene derivative Wyatt, M. D., Lee, et al., (1995), *Biochemistry* 34, 13034–13041; and Brooks, N., et al., (1997), *Bioorganic & Medicinal Chemistry* 5, 1497–1507.

IX. Alkylation of the Exocyclic Amine of Guanine by Polyamide Conjugates

When the thermal cleavage assays were carried out on the 5'-end labeled restriction fragment, a slower mobility fragment appears in the gel electrophoresis assay above the intact DNA indicating the presence of a stable adduct retarding the full-length fragment. The stability of the adduct to heat and piperidine workups suggested that the adduct was the result of alkylation of the exocyclic amine of guanine in the minor groove. To test this, inosine substitution at that position was employed.

Figure 8A:
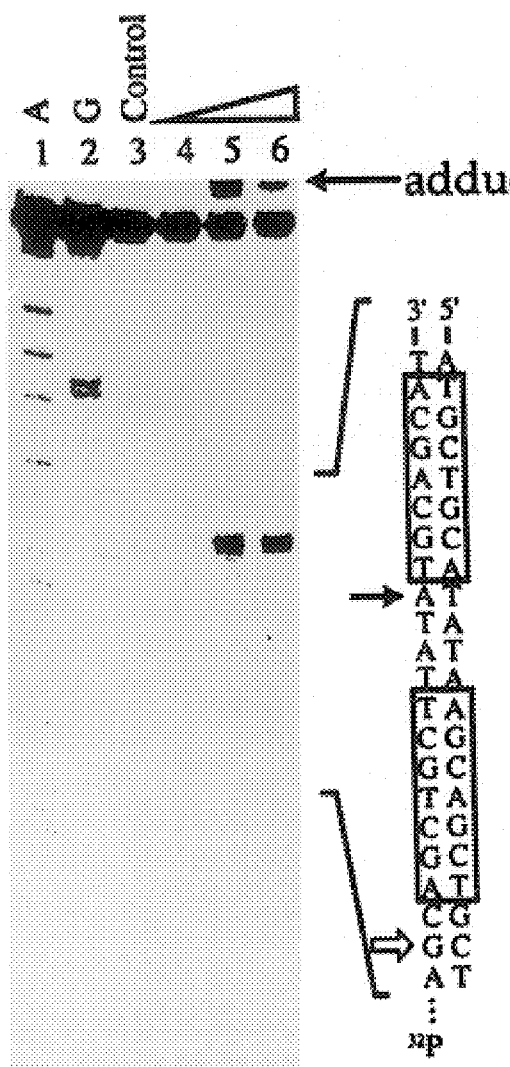
FIG. 8 shows results of thermal cleavage assay experiments with ImPy-β-ImPy-(R)$^{CHL}$γ-ImPy-β-ImPy-β-Dp (2) on 5'-$^{32}$P-end-labeled 120 base pair oligonucleotides with and without inosine substitutions. (a–b) Left, Storage phosphor autodiograms of 8% denaturing polyacrylamide gels used to separate the fragments generated by heat induced DNA cleavage at alkylation sites. All reactions contained 10,000 cpm restriction fragment, 10 mM Tris.HCl (pH 7.0), 10 mM KCl, 10 MM MgCl$_2$ and 5 mM CaCl$_2$ and were performed at 37° C. Following 24 hour of equilibration, the DNA pellet was resuspended in sodium citrate buffer (pH= 7.2) and heated to 90° C. for 15 min to thermally cleave at sites of adenine- or guanine-N3 lesions.. Right, cleavage sites of adenine-N3 lesions. The solid arrows indicate cleavage bands from cleavage sites of adenine-N3 lesions on the restriction fragment. The hollow arrow indicates alkylation at the exocyclic amine of guanine. (a) The fragment (SEQ ID NO:12) contains the site 5'-AGCAGCTGCT (SEQ ID NO:21). Lane 1, A-specific reaction; lane 2, G-specific reaction; lanes 3–6, 100 pM, 1 nM, 10 nM, respectively. (b) The fragments (SEQ ID NO:13) contain the site 5 5'-AGCTGCT-3' (SEQ ID NO:22). Lanes 1–4, 100 pM, 1 nM, 10 nM, respectively. (c) Model bound to match site 5'-AGCTGCT-3'. X indicates site of inosine substitution (SEQ ID NO:15). Models are colored as in FIG. 1.
Figure 8B:
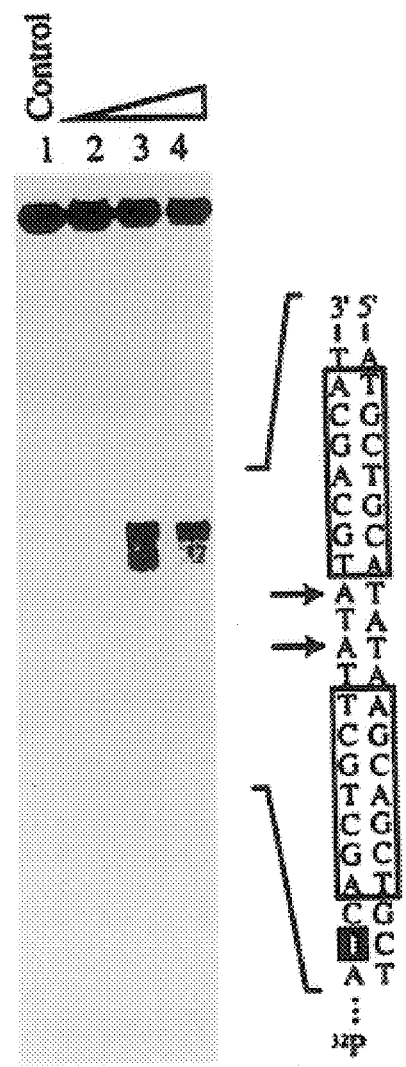
Figure 8C:
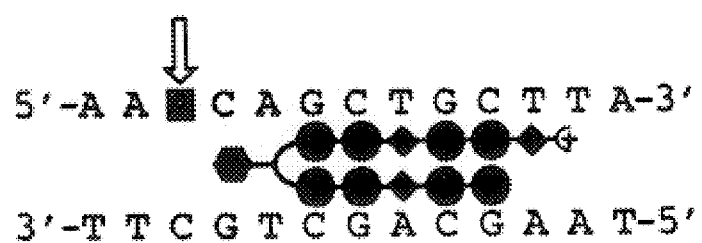
Figure 9:
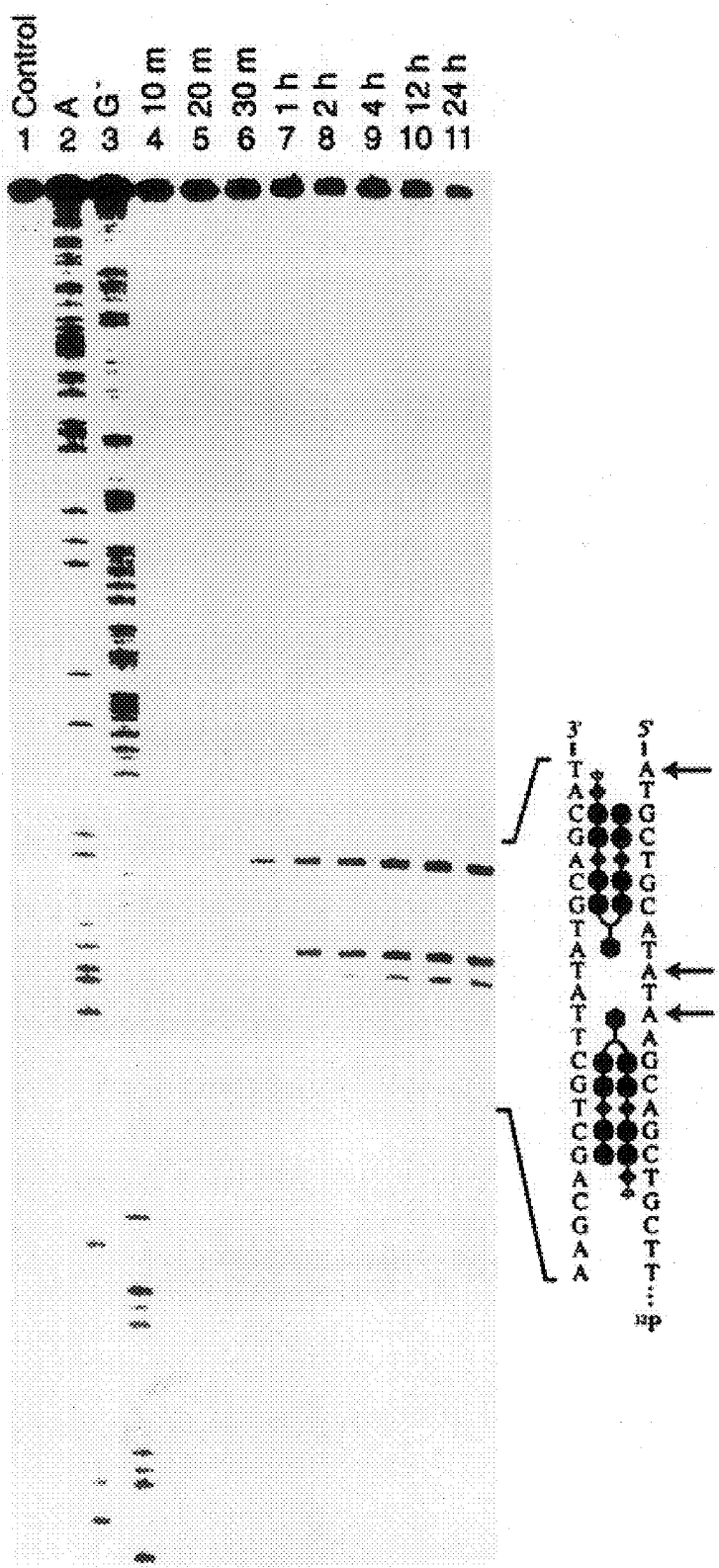
FIG. 9 shows the results of thermal cleavage assay experiments with ImPy-β-ImPy-(R)$^{CHL}$γ-ImPy-β-ImPy-β-Dp (2) on the 3'-$^{32}$P-end-labeled 241 base pair EcoRI/ HindIII restriction fragment from plasmid pHIV-LTR. Storage phosphor autodiogram of 8% denaturing polyacrylamide gels used to separate the fragments generated by heat induced DNA cleavage at alkylation sites. All reactions contained 10,000 cpm restriction fragment, 10 mM Tris.HCl (pH 7.0), 10 mM KCl, 10 mM MgCl$_2$ and 5 mM CaCl$_2$ and were performed at 37° C. Following of equilibrations of 10 minutes-24 hours, the DNA pellet was resuspended in sodium citrate buffer (pH=7.2) and heated to 90° C. for 15 min to thermally cleave at sites of adenine- or guanine-N3 lesions. Lane 1, intact DNA; lane 2, A-specific reaction; lane 3, G-specific reaction; lanes 4–11, 500 pM ImPy-β-ImPy-(R)$^{CHL}$γ-ImPy-β-ImPy-β-Dp (2), equilibrations for 10 min, 20 min, 30 min, 1 h, 2 h, 4 h, 12 h, 24 h, respectively. Right. models bound to match sites on the DNA fragment (SEQ ID NO:15). The polyamide is colored as in FIG. 7. The solid arrows indicate cleavage bands from cleavage sites of adenine- or guanine-N3 lesions on the restriction fragment.
Figure 11:
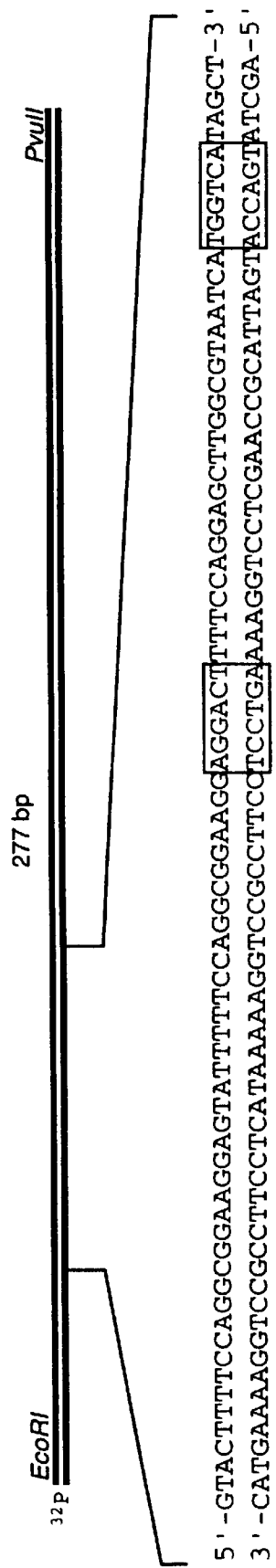
FIG. 11 shows the structures of polyamides and charged control compounds (SEQ ID NO:17). ImImPyPy-γ$^{(R-seco-CBI)}$-ImPyPyPy-β-Dp (1R), ImImPyPy-γ$^{(S-seco-CBI)}$-ImPyPyPy-β-Dp (1S), (R)-seco-CBI-β-dimethyl-γ (2R), and (S)-seco-CBI-γ-dimethyl-β (2S).
Figure 13:
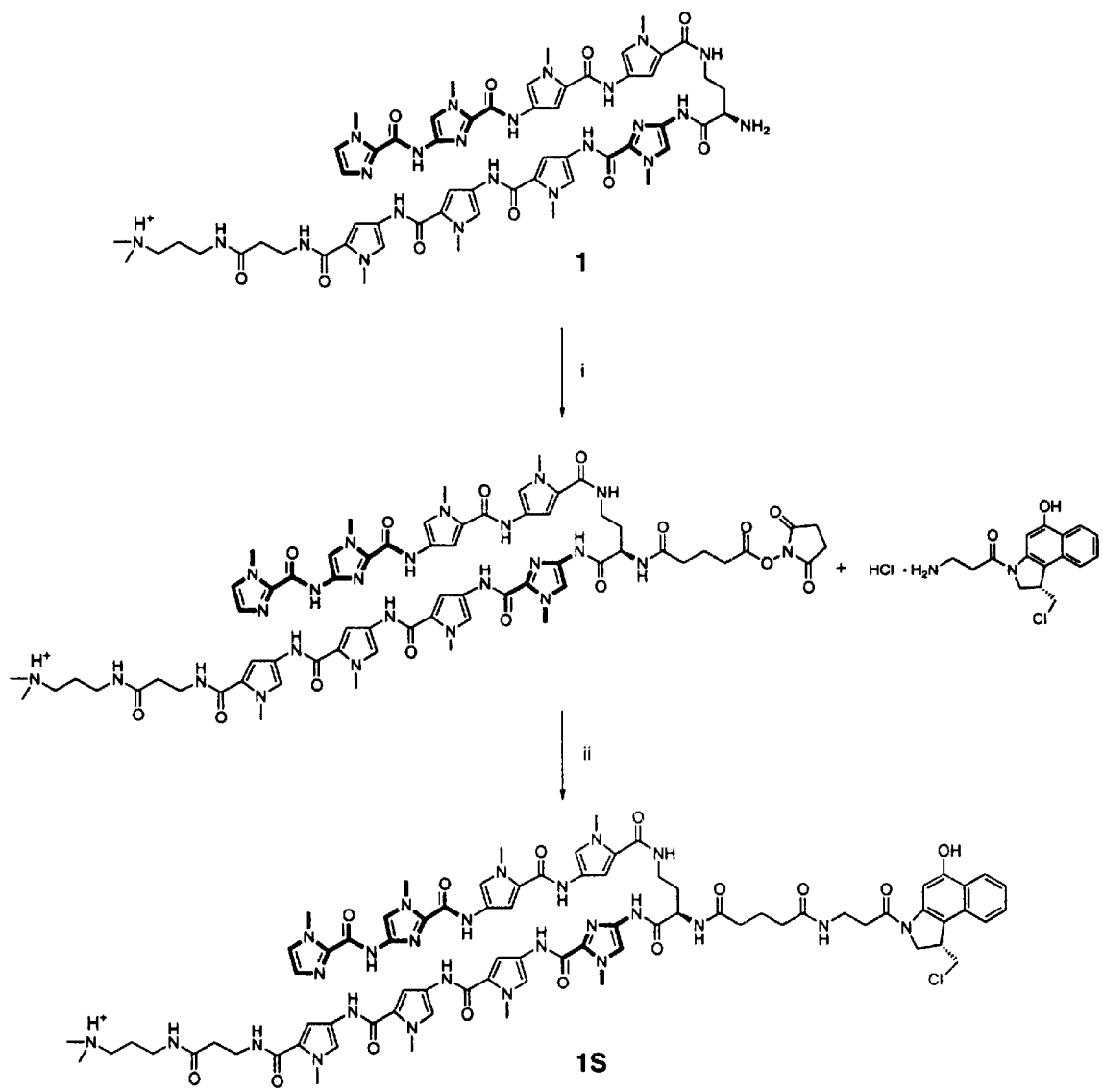
FIG. 13 depicts a synthetic scheme for preparation of seco-CBI-polyamide conjugates, exemplified for ImImPyPy-γ$^{(S-seco-CBI)}$-ImPyPyPy-β-Dp (1S). Polyamides were prepared by already disclosed methods. (i) Disuccinimidyl Glutarate, DMF, 2H, (ii) (S)-seco-CBI-β-Ala, DCC, NHS, DIEA, DMF, 3H.
Figure 14:
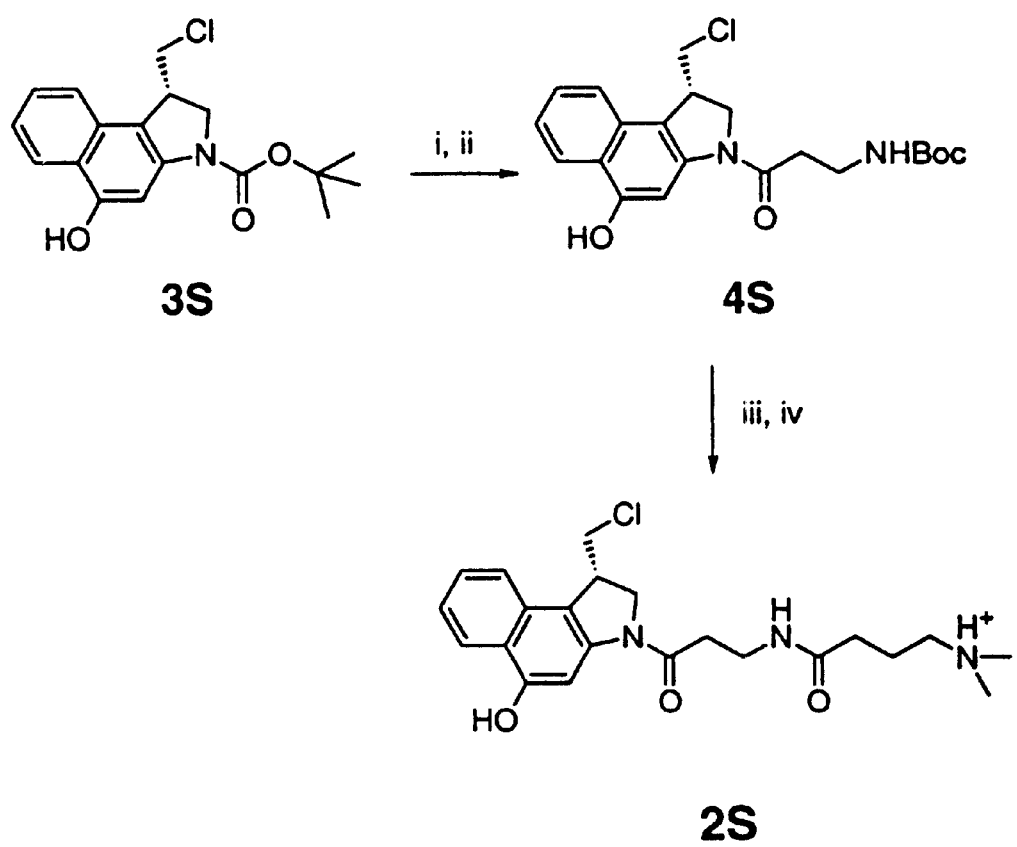
FIG. 14 depicts a synthetic scheme for charged control compounds, exemplified for 2S. (i) 3M HCl/EtOAc, 30 min; (ii) Boc-β-Alanine, HBTU, DIEA, DMF; (iii) 3M HCl/ EtOAc, 30 min; (iv) 4-Dimethylamino butyric acid, HBTU, DIEA, DMF.

Inosine which lacks the exocyclic NH$_2$ of guanine was incorporated into a 120 base-pair fragment at the putative guanine reaction site located adjacent to the match site. The strands with inosine substitutions (SEQ ID NOS:13–14), as well as a strand with no inosine substitutions (SEQ ID NO:12), were 5' end labeled and annealed to a complementary strand and thermal cleavage assays were performed. (FIG. 8) The results of the thermal cleavage assay of the 5' labeled synthetic oligonucleotides without inosine substitutions were identical to alkylation of the restriction fragment (FIG. 9A). Substitution of the guanine in the sequence 5'-A GCAGCTGCT-3' (SEQ ID NO:21) eliminated the anomalous band which results from the stable adduct (FIG. 8B). Thus, certain DNA sequences allow the covalent reaction of the exocyclic amine of guanine by the polyamide-bis (dichloroethylamino)benzene conjugate.

X. Time Dependence of Alkylation

The half life for hydrolysis of the bis(dichloroethylamino) benzene moiety of chlorambucil in water at pH 7.5 and 37° C. is approximately 1.3 hours Kundu, G. C., et al., (1994), *Pharmacology Biochemistry and Behavior* 49, 621–624. One would anticipate that at very low concentrations of polyamide conjugates there will be a competition between inactivation of the conjugate by hydrolysis and binding/ covalent reaction with DNA. Therefore the time dependence of alkylation reactions with the polyamide conjugate 2 at a 0.5 nM concentration were monitored for 24 hours (pH 7.0, 37° C.) (FIG. 9) (SEQ ID NO:15). Under these conditions, alkylation was half completed at match sites in 2.2 hours and the final cleavage yield on the bottom strand was 45%. Cleavage was detectable as early as 10 minutes and the yield did not increase after 24 hours.

XI. Utility

At subnanomolar concentrations the hairpin polyamide delivers the electrophilic bis(dichloroethylamino)benzene to the predetermined sequence and produces a specific covalent reaction in high yield in the minor groove of DNA. The attachment of the chlorambucil moiety at the γ-turn results in no significant alteration of the polyamide-DNA binding affinity. The parent eight-ring hairpin polyamide is cell permeable, and the next technical hurdle is to determine whether the new polyamide-bis(dichloroethylamino) benzene conjugates will also permeate eukaryotic cells. The parent hairpin polyamide 1 has been shown to inhbit HIV replication in cell culture, and this will form the basis of our next experiment. Conjugate 2 targeted to the same HIV-1 promoter can now be tested in cell culture, to determine its ability to inhibit transcription. Further downstream this should set the stage for site specific alkylation in "coding region" of genes in order to inhibit transcription during the elongation phase. Sequence-specific DNA cleavage by multiple polyamide conjugates could provide a basis for "genetic microsurgery," whereby undesired gene segments or integrated viral DNAs could be selectively removed from a host genome in vivo.

XII. Design Considerations for seco-CBI-Polyamide Conjugates

The design of sequence specific DNA alkylating agents requires the integration of two separate entities: recognition and functional reactivity. Pyrrole-imidazole hairpin polyamides are suitable due to their high affinity for DNA and the generality of the pairing rules which allow them to bind any predetermined DNA sequence. For successful bifunctional molecule design, the reactive moiety must specifically alkylate at the target site, and obtain cleavage yields that are quantitative under physiological conditions. In order to maximize stoichiometric reaction on the DNA, the 'cleaving functionality' must be sufficiently reactive with DNA at 37° C., be inert in aqueous media, not react with buffer components, and not suffer unimolecular decomposition in competition with the desired reaction with DNA. Because it meets these criteria, as well as being atom specific and a non-diffusible electrophilic species, we chose (+)-CC-1065 and its analogues for our design of small, bifunctional molecules for sequence specific alkylation.

XIII. Strand Selective Cleavage at a Single Adenine

Figure 17A:
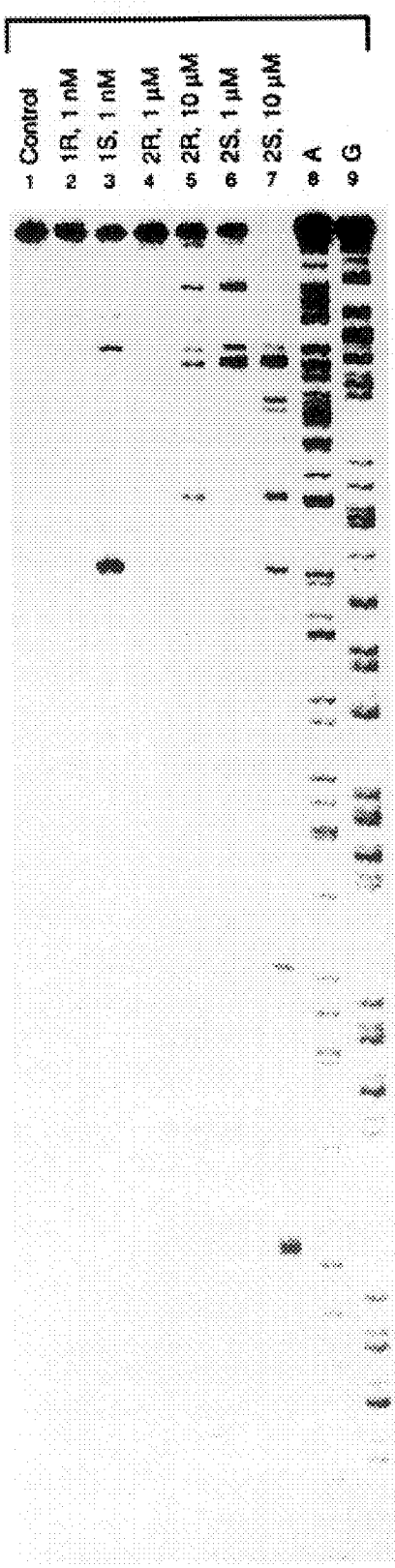
FIG. 17 shows the results of thermally induced strand cleavage on the 5'-end labeled and 3'-end labeled 277 base pair restriction fragment by ImImPyPy-$\gamma^{(R\text{-}sec\text{-}CBI)}$-ImPyPyPy-$\beta$-Dp (1R), ImImPyPy-$\gamma^{(S\text{-}sec\text{-}CBI)}$-ImPyPyPy-$\beta$-Dp (1S), (R)-seco-CBI-$\beta$-dimethyl-$\gamma$ (2R), (S)-seco-CBI-$\beta$-dimethyl-$\gamma$ (2S). Storage phosphor autoradiograms of 8% denaturing polyacrylamide gels used to separate the fragments generated by heat induced DNA cleavage at alkylation sites. All lanes contain 10 kcpm of either 5' or 3' radiolabeled DNA. Each reaction was equilibrated in TE, pH 7.5 at 37° C. for 12 H. The unbound polyamide or agent was removed by precipitation, and then strand cleavage was induced by heating at 95° C. for 30 min. (a) 5'-$^{32}$P-end labeled restriction fragment. (b) 3'-$^{32}$P-end labeled restriction fragment. (a–b) Lane 1, intact DNA; lane 2, 1R, 1 nM; lane 3 1S, 1 nM; lanes 4–5, 2R, 1 $\mu$M and 10 $\mu$M, respectively; lanes 6–7, 2S, 1 $\mu$M and 10 $\mu$M, respectively; lane 8, A-specific reaction; lane 9, G-specific reaction.
Figure 17B:
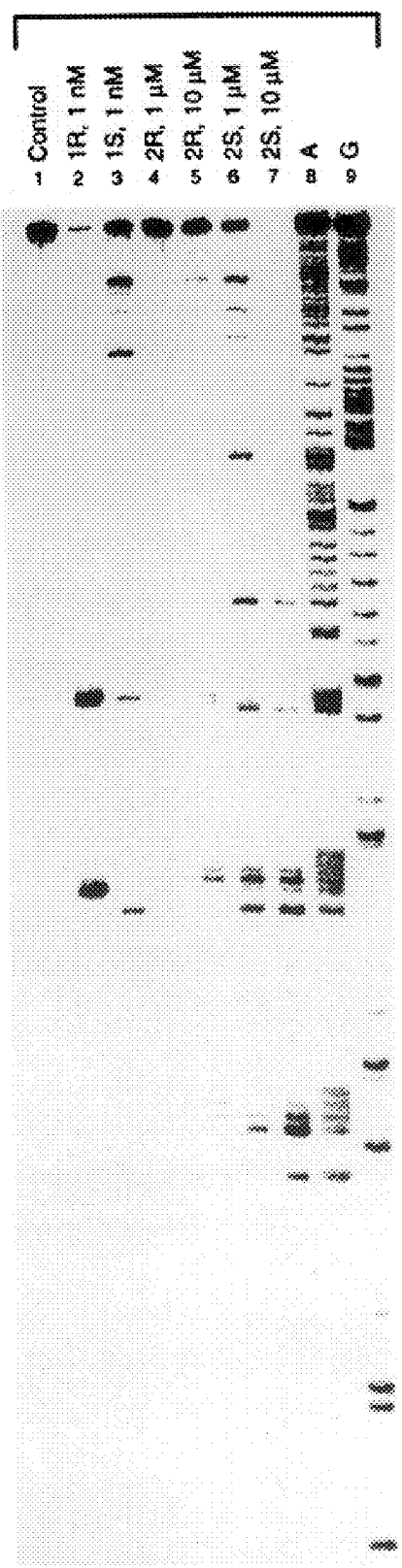

One of the most striking differences between polyamide conjugates 1R and 1S is the strand selectivity of alkylation shown by the respective enantiomers of seco-CBI. This exploits both the DNA binding properties of the polyamide and the binding orientation preferences for alkylation of CBI. From previous reports, polyamide 1' has subnanomolar binding affinity [White, S. et al. *Nature* 1998, 391, 468–471; and Bremer, R. E. et al. *Chem. Biol.* 1998, 5, 119–133] while the CBI control compounds 2R and 2S presented here alkylate only at micromolar concentrations (FIG. 17). The hairpin polyamide portion of the molecule is successfully directing both the DNA binding sequence context and the orientation preferences of the polyamide-CBI conjugate.

Figure 15A:
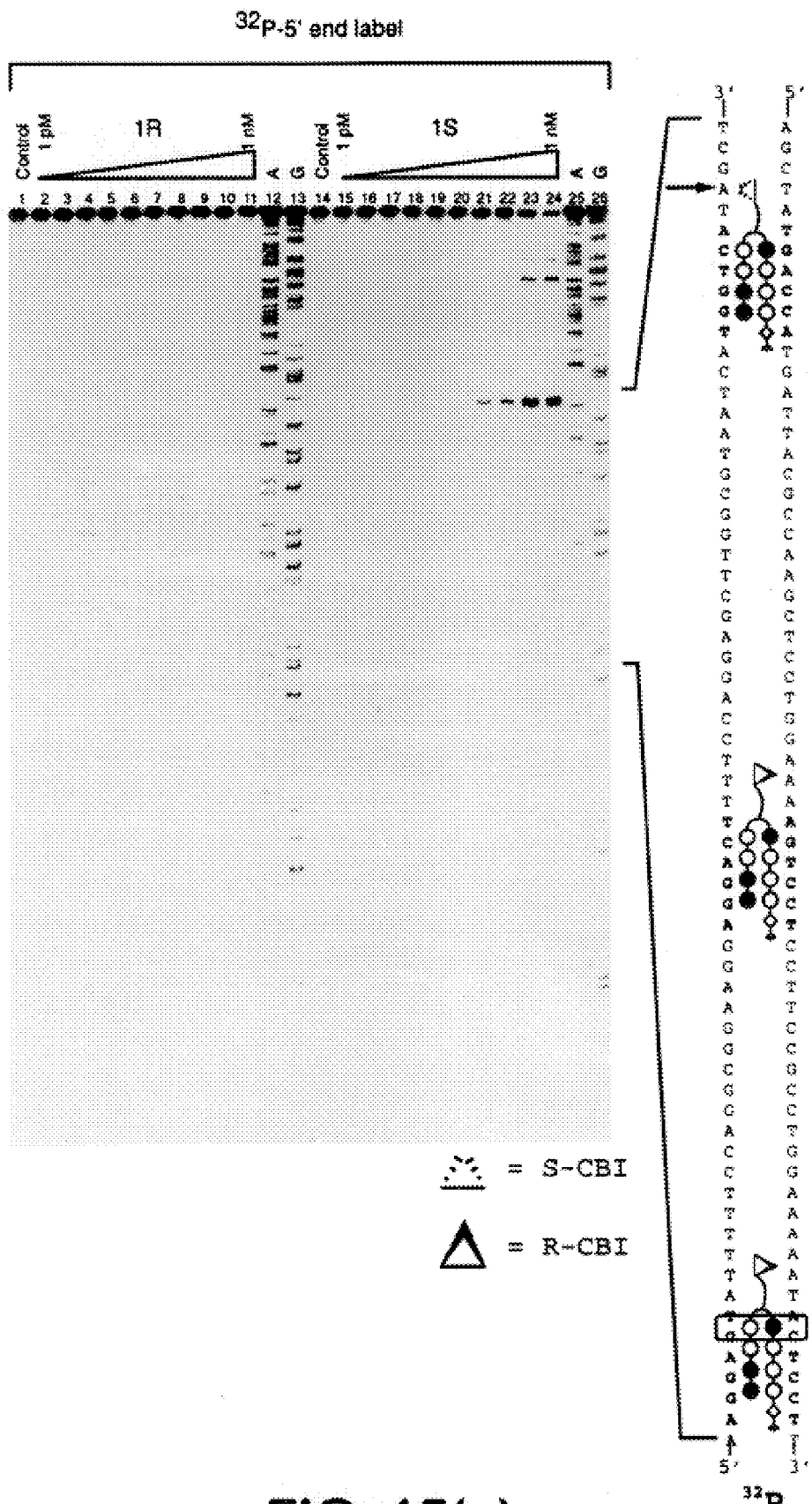
FIG. 15 shows the results of thermally induced strand cleavage on the 5'-end labeled and 3'-end labeled 277 base pair restriction fragment by ImImPyPy-γ$^{(R-secoCBI)}$-ImPyPyPy-β-Dp (1R) and ImImPyPy-γ$^{(S-seco-CBI)}$-ImPyPyPy-β-Dp (1S). Storage phosphor autoradiograms of 8% denaturing polyacrylamide gels used to separate the fragments generated by heat induced DNA cleavage at alkylation sites. All lanes contain 10 kcpm of either 5' or 3' radiolabeled DNA. Each reaction was equilibrated in TE, pH 7.5 at 37° C. for 12 H. The unbound polyamide was removed by precipitation, and then strand cleavage was induced by heating at 95° C. for 30 min. (a) 5'-$^{32}$P-end labeled restriction fragment (SEQ ID NO:18). (b) 3'-$^{32}$P-end labeled restriction fragment. (a–b) lanes 1 and 14, intact DNA; lanes 2–11, 15–24, 1 pM, 2 pM, 5 pM, 10 pM, 20 pM, 50 pM, 100 pM, 200 pM, 500 pM, 1 nM respectively of the corresponding polyamide; lanes 12 and 25, A-specific reaction; lanes 13 and 26, G-specific reaction. (a–b) Ball-and-stick models of polyamides bound to match and mismatch sites on the DNA fragment. Match sites 5'-TGGTCA-3' and 5'-AGGACT-3' and single base pair mismatch site 5'-AGGAGT-3' are indicated in bold on the sequence, with arrows indicating cleavage bands. The polyamide is colored as in FIG. 10, with the bold triangle representing (R)-CBI.
Figure 15B:
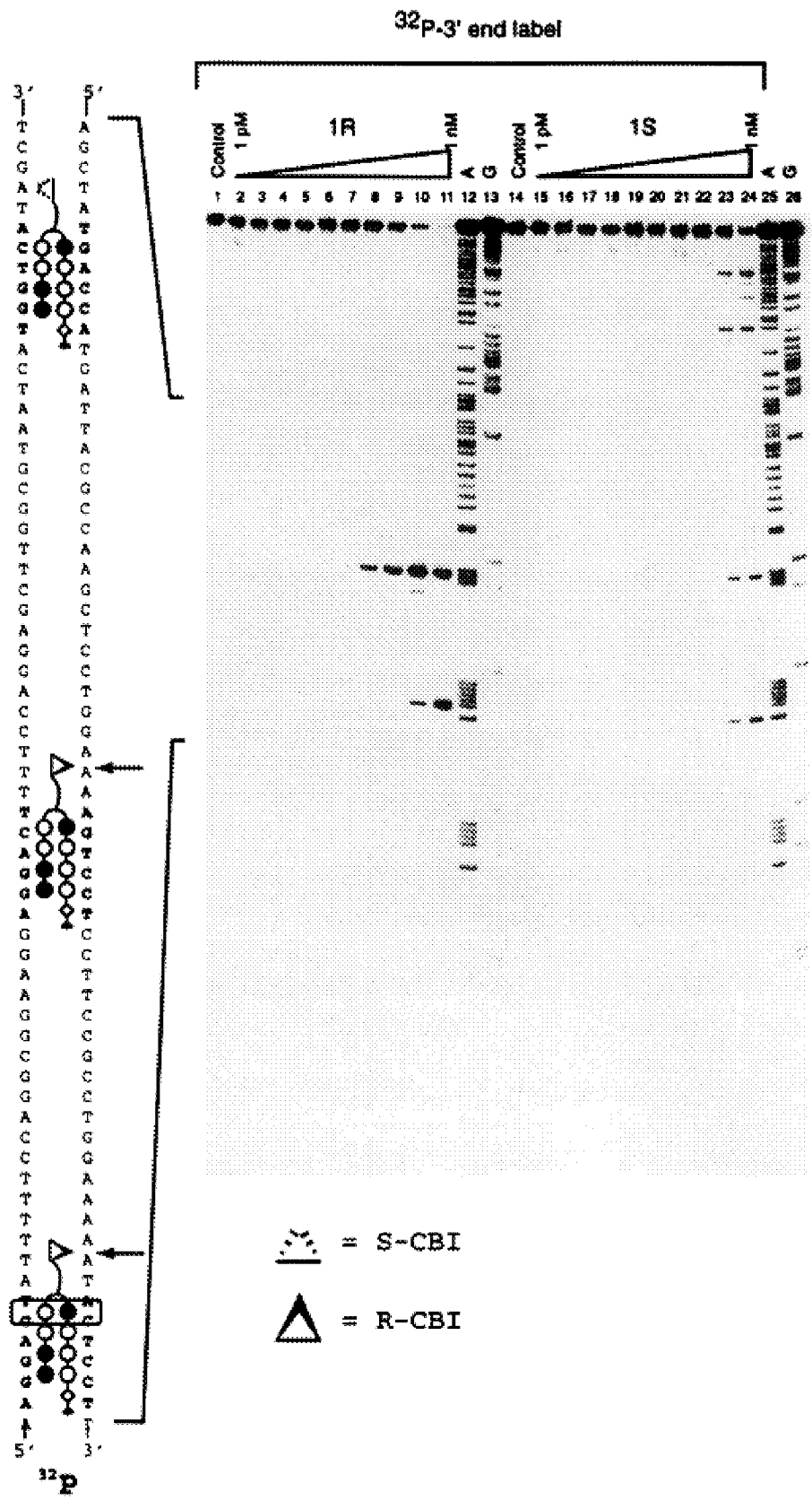
Figure 16A:
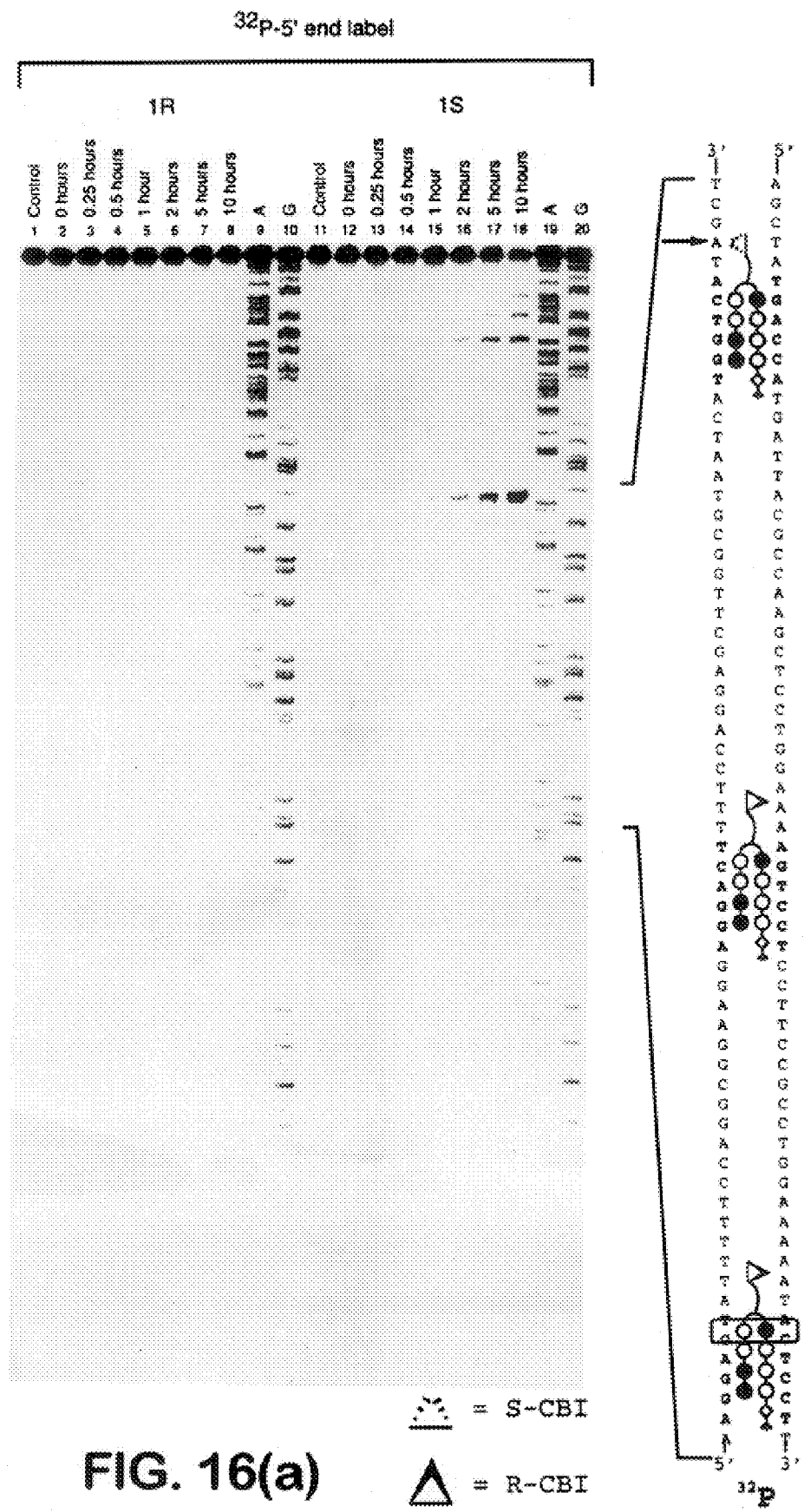
FIG. 16 shows the results of time course experiments of thermally induced strand cleavage on the 5'-end labeled and 3'-end labeled 277 base pair restriction fragment by ImImPyPy-γ$^{(R-seco-CBI)}$-ImPyPyPy-β-Dp (1R) and ImImPyPy-γ$^{(S-seco-CBI)}$-ImPyPyPy-β-Dp (1S). Storage phosphor autoradiograms of 8% denaturing polyacrylamide gels used to separate the fragments generated by heat induced DNA cleavage at alkylation sites. All lanes contain 10 kcpm of either 5' or 3' radiolabeled DNA. Each reaction was equilibrated in TE, pH 7.5 at 37° C. from 0 to 10 hours. The unbound polyamide was removed by precipitation, and then strand cleavage was induced by heating at 95° C. for 30 min. (a) 5'-$^{32}$P-end labeled restriction fragment (SEQ ID NO: 18). (b) 3'-$^{32}$P-end labeled restriction fragment. (a–b) lanes 1 and 11, intact DNA; lanes 2–8, 1 nM of corresponding polyamide, equilibrations for 0, 15 minutes, 30 minutes, 1 hour, 2 hours, 5 hours, and 10 hours, respectively; lanes 9 and 19, A-specific reaction; lanes 10 and 20, G-specific reaction. (a–b) Ball-and-stick models of polyamides bound to match and mismatch sites on the DNA fragment. Match sites 5'-TGGTCA-3' and 5'-AGGACT-3' and single base pair mismatch site 5'-AGGAGT-3' are indicated in bold on the sequence, with arrows indicating cleavage bands. The polyamide is colored as in FIG. 10, with the bold triangle representing (R)-CBI.
Figure 16B:
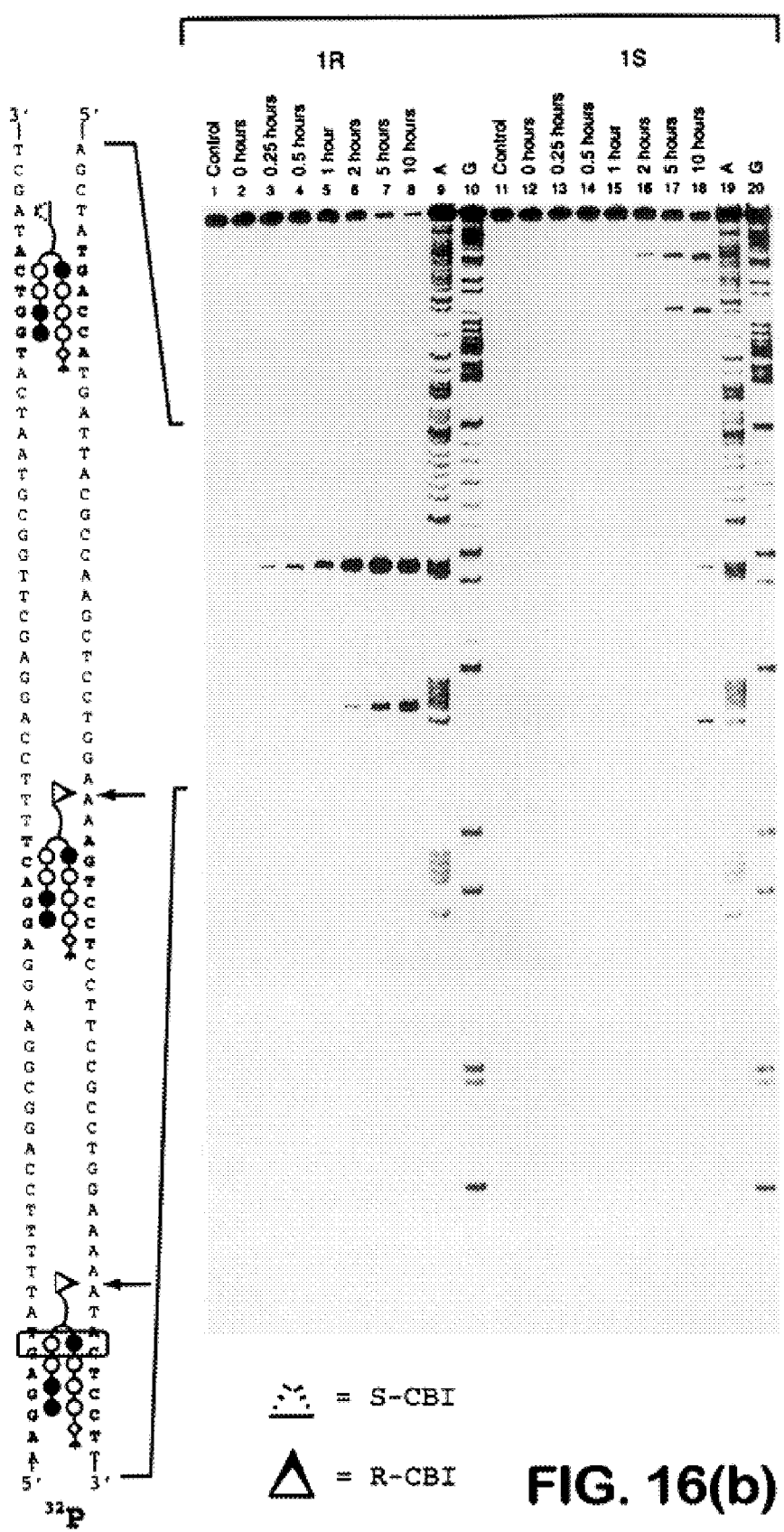

Tethering the alkylating CBI moiety to the hairpin polyamide results in a bifunctional molecule that will bind within the sequence context and orientation preferences of the polyamide, but will only alkylate when the sequence and orientation requirements of the alkylating agent are satisfied. In the strand cleavage experiments, 1S alkylates adjacent to a match site such that the polyamide. binds 5' to 3', N-terminus to C-terminus and the alkylated adduct formed by CBI has a 3' to 5' orientation from the site of alkylation (see FIGS. 15 and 16 for ball-and-stick models) (SEQ ID NO:18). These results are consistent with the known binding orientation preferences of CBI. The reactive cyclopropyl ring is placed properly for attack by the N3 of adenine when the S (+, naturally occurring) enantiomer of CBI is bound in a 3' to 5' direction from the site of alkylation. Likewise, studies from Boger and coworkers find that the R (−, unnatural) enantiomer of CBI binds in a 5' to 3' direction to accommodate the cyclopropyl ring in the opposite stereochemistry. Boger, D. L. and Johnson, D. S. *Angew. Chem., Int. Ed. Engl.* 1996, 35, 1438–1474. Conjugate 1R shows no alkylation anywhere on the 5'-labeled strand. 1R does show alkylation at the site which includes a match site for the polyamide, but with an adenine on the opposite strand, allowing it to have the proper orientation for alkylation. While the charged seco-CBI analogues alkylated at several adenines within the AT tracts, the conjugate alkylates at a single adenine at much lower concentrations, indicating that the polyamide is directing CBI to the appropriate adenine in the minor groove.

XIV. Effects of Sequence Composition on Rates and Yields of Alkylation

It has been shown for CC-1065 and other analogues that the S, or (+)-enantiomers are 10 times more reactive than the R, or (−)-enantiomers. Boger, D. L. and Munk, S. A. *J. Am. Chem. Soc.* 1992, 114, 5487–5496; Boger, D. L. et al. *Bioorg. Med. Chem. Lett.* 1992, 2, 759; Boger, D. L. et al. *Bioorgan. Med. Chem.* 1995, 3, 761–775; and Boger, D. L. et al. *J. Am. Chem. Soc.* 1997, 119, 4987–4998. The data shown for compounds 2R and 2S support this conclusion (FIG. 17). Polyamide conjugate 1R shows higher alkylation efficiency and faster rates of alkylation than 1S. Work by Lukhtanov and coworkers have shown that when an oligonucleotide-cyclopropapyrroloindole conjugate is hybridized to a variety of complementary oligonucleotide hairpins, rates of reaction can be quite rapid, and yields can be quantitative. Lukhtanov, E. A. et al. *J. Am. Chem. Soc.* 1997, 119, 6214–6225. But the results are sequence dependent. For both enantiomers, straight AT tracts allow for fast and efficient alkylation ($t_{1/2}$ as fast as 2 minutes), while mixed sequences seem to have slower and more unpredictable rates of reactivity. In the case of the polyamide-CBI conjugate, for 1R the flanking sequence outside its match alkylation site contains three adenines. The flanking sequence outside the match alkylation site for 1S is mixed, 5'-ATGGTCATAGC-3' (SEQ ID NO:23). The reactivity of the single CBI unit would predict that 1S would be a more efficient alkylating agent, but the sequence context of the alkylation site also plays a significant role in the rate and yield of alkylation efficiency.

Hairpin polyamide-CBI conjugates have been shown to efficiently and selectively alkylate a single adenine adjacent to a polyamide match site. Because of the high efficiency of alkylation, these molecules should be useful in the design of reagents that target a single gene. It has already been shown that triplex forming oligonucleotide-psoralen and nitrogen mustard conjugates form covalent adducts with the coding strand to inhibit elongation of transcription. Ebbinghaus, S. W. et al. *Biochemistry* 1999, 38, 1619–628. This class of polyamide-CBI conjugates will be a useful tool for functional genomics.

EXAMPLES

The following examples below are non-limiting and are offered merely for purposes of illustrating the practice of certain preferred embodiments of the invention herein described, specifically the design, synthesis, and testing of two representative polyamide-alkylator conjugates. Illustration of the techniques described in the examples and in the detailed description above may be found in any of several well-known references, such as: Sambrook, J., et al., *Molecular Cloning: A Laboratory Manual,* Cold Spring Harbor Laboratory Press (1989); Goeddel, D., ed., *Gene Expression Technology, Methods in Enzymology,* 185, Academic Press, San Diego, Calif. (1991); "Guide to Protein Purification" in Deutshcer, M. P., ed., *Methods in Enzymology,* Academic Press, San Diego, Calif. (1989); Innis, et al., PCR Protocols: *A Guide to Methods and Applications,* Academic Press, San Diego, Calif. (1990); Freshney, R. I., *Culture of Animal Cells: A Manual of Basic Technique,* $2^{nd}$ Ed., Alan Liss, Inc. New York, N.Y. (1987): Murray, E. J., ed., *Gene Transfer and Expression Protocols,* pp. 109–128, The Humana Press Inc., Clifton, N J and Lewin, B., *Genes VI,* Oxford University Press, New York (1997).

Part A

Materials $^1$H NMR spectra were recorded on a General Electric-QE NMR spectrometer at 300 MHz with chemical shifts reported in parts per million relative to residual solvent. UV spectra were measured in water on a Hewlett-Packard Model 8452A diode array spectrometer. Matrix assisted, laser desorption/ionization time-of-flight mass spectrometry (MALDI-TOF) was performed at the Protein and Peptide Microanalytical Facility at the California Institute of Technology. HPLC analysis was performed using a Beckman Gold Nouveau system using a Rainen C18, Microsorb MV, 5 $\mu$m, 300×4.6 mm reversed phase column on 0.1% (wt/v) TFA with acetonitrile as eluent and a flow rate of 1.0 ml/min, gradient elution 1.25% acetonitrile/min. Preparatory reverse phase HPLC was performed on a Beckman HPLC with a Waters DeltaPak 25×100 mm, 100-$\mu$m C18 column equipped with a guard, 0.1% (wt/v) TFA, 0.25% acetonitrile/min. Water was obtained from a Millipore MilliQ water purification system, and all buffers were 0.2 $\mu$m filtered. Reagent-grade chemicals were used unless otherwise stated.

Oligonucleotides were synthesized by the Caltech Biopolymer Synthesis and Analysis Resource Center. Restriction enzymes were purchased from either New England Biolabs or Boeringer-Mannhein and used accorded to the manufacturer's protocols. [$\alpha$-$^{32}$P]-Thymidine-5'-triphosphate ($\geq$3000 Ci. mmol) and [$\alpha$-$^{32}$P]-deoxyadenosine-5'-triphosphate ($\geq$6000 Ci. mmol) were purchased from DuPont/NEN. [$\gamma$-$^{32}$P]-Adenosine-5'-triphosphate ($\geq$7000 Ci. mmol) was obtained from ICN.

Example 1

Synthesis of Polyamide-bis(dichloroethylamino) benzene Conjugate

ImPy-$\beta$-ImPy-(R)$^{H_2N}\gamma$-ImPy-$\beta$-ImPy-$\beta$-Dp (5). ImPy-$\beta$-ImPy-(R)$^{H_2N}\gamma$-ImPy-$\beta$-ImPy-$\beta$-Pam-resin was synthesized in a stepwise fashion by Boc-chemistry manual solid phase protocols. Herman, D. M., et al., (1998); J. Am. Chem. Soc. 120, 1382–1391; and Baird, E. E. & Dervan, P. B. (1996), J. Am. Chem. Soc. 118, 6141–6146. A sample of the resin was treated with neat (dimethylamino)-propylamine (2 ml), heated (55° C., 48 hours) and purified by reversed phase HPLC. ImPy-$\beta$-ImPy-(R)$^{H_2N}\gamma$-ImPy-$\beta$-ImPy-$\beta$-Dp was recovered as a white powder upon lyophilization of the appropriate fraction (18 mg, 10.4% recovery). UV (H$_2$O) $\lambda_{max}$ ($\epsilon$), 306 (69,500); $^1$H NMR (DMSO-d$_6$): $\delta$10.97 (s, 1H), 10.39 (s, 1H), 10.25 (s, 1H), 10.00 (s, 1H), 9.97 (s, 1H), 9.90 (s, 1H), 9.24 (bs, 1H), 8.15 (m, 5H), 8.03 (bd, 3H, J=6.1 Hz), 7.47 (s, 1H), 7.42 (s, 1H), 7.40 (s, 1H), 7.35 (s, 1H), 7.18 (m, 4H), 7.01 (s, 1H), 6.97 (s, 1H), 6.92 (s, 1H), 6.90 (m, 2H), 3.91 (m, 13H), 3.75 (s, 12H), 3.33 (m, 6H), 3.24 (m, 2H), 3.06 (q, 2H, J=6.0), 2.95 (quintet, 2H, J=5.0), 2.54 (t, 4H, J=6.8 Hz), 2.30 (t, 2H, J=7.0), 1.94 (m, 2H), 1.68 (quintet, 2H, J=7.3 Hz); MALDI-TOF-MS (monoisotopic) [M+H] 1381.6 (1381.6 calcd for C$_{62}$H$_{81}$N$_{26}$O$_{12}$).

ImPy-$\beta$-ImPy-(R)$^{CHL}\gamma$-ImPy-$\beta$-ImPy-$\beta$-Dp (2). To a solution of chlorambucil (5.7 mg, Fluka) in 20 $\mu$l DMF was added DCC (7.7 mg) and HOBt (2.7 mg). The solution was stirred for 1 hour. The OBt ester solution was added to ImPy-$\beta$-ImPy-(R)$^{H_2N}\gamma$-ImPy-$\beta$-ImPy-$\beta$-Dp (4 mg) in 400 $\mu$l DMF followed by 200 $\mu$l DIEA. The reaction mixture was stirred for 2 hours. TFA (150 $\mu$l) was added to the reaction mixture and the mixture was purified by reversed phase HPLC. ImPy-$\beta$-ImPy-(R)$^{CHL}\gamma$-ImPy-$\beta$-ImPy-$\beta$-Dp was recovered as a white powder upon lyophilization of the appropriate fraction (1 mg, 21% recovery). UV (H$_2$O ) $\lambda_{max}$ ($\epsilon$) 306 (69,500); $^1$H NMR (DMSO-d$_6$): $\delta$10.43 (s, 1H), 10.31 (s, 1H), 10.30 (s, 1H), 10.25 (s, 1H), 10.09 (s, 1H), 9.96 (s, 1H), 9.52 (s, 1H), 8.09, (m, 8H), 7.47 (s, 2H), 7.45 (s, 1H), 7.40 (s, 1H), 7.25 (m, 4H), 7.05 (s, 2H), 7.02 (s, 1H), 6.96 (m, 4H), 6.67 (s, 1H), 6.64 (s, 1H), 3.98 (s, 3H), 3.95 (s, 6H), 3.81 (s, 6H), 3.79 (s, 1H), 3.69 (s, 6H), 3.52 (M, 8H), 3.12 (q, 2H, J=5.8 Hz), 3.01 (quintet, 2H, J=6.0 Hz), 2.75 (d, 6H, J=4.7 Hz), 2.61 (m, 4H), 2.37 t, (t, J=6.9 Hz), 2.03 (t, 6H, J=6.9 Hz), 2.01 (m, 8H), 1.74 (m, 4H), 1.63 (m, 2H), 1.47 (m, 2H); MALDI-TOF-MS (monoisotopic) [M+H] 1666.7 (1666.7 calcd for C$_{76}$H$_{98}$Cl$_2$N$_{27}$O$_{13}$)

Dp-CHL (4) To a solution of chlorambucil (304 mg) in 500 $\mu$l DMF was added DCC (208 mg) and HOBt (143 mg). The solution was stirred for 1 hour. The OBt ester solution was added to (dimethylamino)-propylamine (63 $\mu$l) in 500 $\mu$l DMF followed by 500 $\mu$l DIEA. The reaction mixture was stirred for 2 hours. TFA (0.01% (wt/v), 6 ml) was added to the reaction mixture and the mixture was purified by reversed phase HPLC. Dp-CHL is recovered as a yellow oil upon lyophilization of the appropriate fraction (50 mg, 12.9% recovery). NMR; MALDI-TOF-MS (monoisotopic) [M+H] 388.4 (388.4 calcd for C$_{19}$H$_{31}$Cl$_2$N$_3$O).

Example 2

Preparation of 3'- or 5'-$^{32}$P-labeled DNA Restriction Fragment

Plasmid pHIV-LTR [Jones, K. A. & Peterlin, B. M. (1994), *Annual Review of Biochemistry* 63, 717–743] was digested with EcoRI, labeled at either the 3' or 5' end and digested with HindIII. The 241-base-pair restriction fragment was isolated by nondenaturing gel electrophoresis. Chemical sequencing reactions were performed as described [Maxam, A. M. & Gilbert, W. (1986), *Molecular Biology* 20, 461–509; and Iverson, B. L. & Dervan, P. B. (1987), *Nucleic Acids Research* 15, 7823–7830]. Standard techniques were employed for DNA manipulation [Sambrook, J., Fritsch, E. F. & Maniatis, T. (1989). *Molecular Cloning*. Cold Spring Harbor Laboratory, Cold Spring Harbor, N.Y.].

Example 3

Detection of Heat-induced Single-strand DNA Cleavage

All reactions were executed in a total volume of 40 µl. A polyamide stock solution or H$_2$O was added to an assay buffer containing radiolabeled restriction fragment (10,000 cpm), affording final solution conditions of 10 mM Tris.HCl, 10 mM KCl, 10 mM MgCl$_2$, 5 mM CaCl$_2$, pH 7.0, and either 1 pM-10 nM nitrogen mustard-polyamide conjugate or no conjugate (for reference lanes). The solutions were equilibrated at 37° C. for the desired time period. The reactions were stopped by the addition of 60 µl of a solution containing 0.6 M NaOAc, 12.5 mM EDTA, 0.15 mM (bp) calf thymus DNA, 2.0 M NaCl, 0.8 mg/ml glycogen, and ethanol precipitated. Reactions were resuspended in 40 µl 10 nM sodium citrate buffer, pH 7.2, and heated for 30 minutes at 95° C. The reactions were ethanol precipitated and resuspended in 1×TBE/80% formamide loading buffer, denatured by heating at 85° C. for 10 minutes, and placed on ice. The reaction products were separated by electrophoresis on an 8% polyacrylamide gel (5% cross-link, 7 M urea) in 1×TBE at 2000 V. Gels were dried and exposed to a storage phosphor screen (Molecular Dynamics) [Johnston, R. F., Pickett, S. C. & Barker, D. L. (1990). Autoradiography using storage phosphor technology. *Electrophoresis* 11, 355–360].

Example 4

Quantitative DNase I Footprint Titration Experiments

All reactions were executed in a total volume of 400 µl. A polyamide stock solution or H$_2$O (for reference lanes) was added to an assay buffer containing radiolabeled restriction fragment (20,000 cpm) affording final solution conditions of 10 mM Tris.HCl, 10 mM KCl, 10 mM MgCl$_2$, 5 mM CaCl$_2$, pH 7.0, and either 1 pM-10 nM nitrogen mustard-polyamide conjugate or no conjugate (for reference lanes). The solutions were allowed to equilibrate at 22° C. for 18 hours. Footprinting reactions were initiated by the addition of 4 µl of a DNase I stock solution (at the appropriate concentration to give about 55% intact DNA) containing 1 mM DTT and allowed to proceed for 7 min at 22° C. The reactions were stopped by the addition of 50 µl of a solution containing 1.25 M NaCl, 100 mM EDTA, 0.2 mg/ml glycogen, and 28 µM (bp) calf thymus DNA, and ethanol precipitated. Reactions were resusperded in 1×TBE/80% formamide loading buffer, denatured by heating at 85° C. for 10 min, and placed on ice. The reaction products were separated by electrophoresis on an 8% polyacrylamide gel (5% cross link, 7M urea) in 1×TBE at 2000 V for 1.5 h. Gels were dried and exposed to a storage phosphor screen (Molecular Dynamics).

Example 5

Quantitation and Data Analysis

Data from the footprint titration gels were obtained using a Molecular Dynamics 400S PhosphorImager followed by quantitation using ImageQuant software (Molecular Dynamics). Background-corrected volume integration of rectangles encompassing the footprint sites and a reference site at which DNase I reactivity was invariant across the titration generated values for the site intensities ($I_{site}$) and the reference intensity ($I_{ref}$). The apparent fractional occupancy ($\theta_{app}$) of the sites were calculated using the equation:

$$\theta_{app} = 1 - \frac{Isite/Iref}{Isite°/Iref°}$$

where I°$_{site}$ and I°$_{ref}$ are the site and reference intensities, respectively, from a control lane to which no polyamide was added. The ([L]$_{tot}$, $\theta_{app}$) data points were fit to a Langmuir binding isotherm (eq 2, n=1) by minimizing the difference between $\theta_{app}$ and $\theta_{fit}$, using the modified Hill equation:

$$fit = \min + (\max - \min)\frac{K_a^n[L]_{tot}^n}{1 + K_a^n[L]_{tot}^n}$$

where [L]$_{tot}$ is the total polyamide concentration, K$_a$ is the equilibrium association constant, and $\theta_{min}$ and $\theta_{max}$ are the experimentally determined site saturation values when the site is unoccupied or saturated, respectively. The data were fit using a nonlinear least-squares fitting procedure with K$_a$, $\theta_{max}$, and $\theta_{min}$ as the adjustable parameters. All acceptable fits had a correlation coefficient of R>0.97. Five sets of data were used in determining each association constant. All lanes from each gel were used unless visual inspection revealed a data point to be obviously flawed relative to neighboring points.

Part B
Experimental
Materials $^1$H NMR spectra were recorded on a General Electric-QE NMR spectrometer at 300 MHz and a Varian Inova NMR spectrometer at 500 MHz with chemical shifts reported in parts per million relative to residual solvent. UV spectra were measured in water on a Hewlett-Packard Model 8452A diode array spectrophotometer. Optical rotations were recorded on a JASCO Dip 1000 digital polarimeter. Matrix-assisted, laser desorption/ionization time-of-flight mass spectrometry (MALDI-TOF) was performed at the Protein and Peptide Microanalytical Facility at the California Institute of Technology. Preparatory reversed phase HPLC was performed on a Beckman HPLC with a Waters DeltaPak 25×100 mm, 300 Å C18 column equipped with a guard, 0.1% (wt/v) TFA, 0.25% acetonitrile/min.

DNA Reagents and Materials. Enzymes were purchased from Boehringer-Mannheim and used with their supplied buffers. Deoxyadenosine and thymidine 5'-[α-$^{32}$P] triphosphates were obtained from Dupont/New England Nuclear, and deoxyadenosine 5'-[γ-$^{32}$P] triphosphates were purchased from I.C.N. Sonicated, deproteinized calf thymus DNA was acquired from Pharmacia. RNase free water was obtained from USB and used for all reactions. All other reagents and materials were used as received. All DNA manipulations were performed according to standard protocols.

Example 6

Synthesis of CBI-polyamide Conjugates

ImImPyPy-(R)$^{H_2N}$γ-ImPyPyPy-β-Dp (1'). ImImPyPy-(R)$^{H_2N}$γ-ImPyPyPy-β-Pam resin was synthesized in a stepwise fashion by Boc-chemistry manual solid phase protocols. A sample of resin was treated with neat (dimethylamino)-propylamine (2 ml), heated (55° C., 24 hours) and purified by reversed phase HPLC. ImImPyPy-(R)$^{H_2N}$γ-ImPyPyPy-β-Dp was recovered as a white powder upon lyophilization of the appropriate fraction (14.3 mg, 11.6 µmoles, 4.8% recovery). UV (H$_2$O) λ$_{max}$ (ε), 312 nm, (66, 600); $^1$H NMR (500 MHz, DMSO-d$_6$): δ=11.009 (s, 1H), 10.325 (s, 1H), 10.073 (s, 1H), 9.947 (s, 1H), 9.936 (s, 1H), 9.870 (s, 1H), 9.07 (s, 1H), 9.23 (br s, 1H, CF$_3$COOH), 8.334 (s, 3H), 8.173 (t, 1H, J=6 Hz), 8.040 (t, 1H, J=6 Hz), 8.012 (t, 1H, J=6 Hz), 7.567 (s, 1H), 7.530 (s, 1H), 7.457 (s, 1H), 7.270 (s, 1H), 7.256 (s, 1H), 7.200 (s, 1H), 7.177 (s, 1H), 7.164 (s, 1H), 7.155 (s, 1H), 7.142 (s, 1H), 7.071 (m, 2H), 6.964 (s, 1H), 6.876 (s, 1H), 4.002 (m, 6H), 3.978 (s, 3H), 3.853 (s, 3H), 3.842 (s, 3H), 3.833 (s, 3H), 3.807 (s, 3H), 3.792 (s, 3H), 3.375 (q, 2H, J=5.5 Hz), 3.294 (m, 2H, J=5.5 Hz), 3.106 (q, 2H, J=6.5 Hz), 2.997 (m, 3H), 2.735 (s, 3H), 2.725 (s, 3H), 2.343 (t, 2H, J=7 Hz), 1.738 (m, 2H), 1.633 (m, 2H). MALDI-TOF-MS (monoisotopic) [M+H] 1238.83 (calculated 1238.58 for C$_{57}$H$_{72}$N$_{23}$O$_{10}$.)

ImImPyPy-(R)$^{Glu-NHS}$γ-ImPyPyPy-β-Dp (1-NHS). To a solution of disuccinimidyl glutarate (41.9 mg, 120 µmoles) in 2.5 ml DMF was added 100 µl of a 14.3 mM solution of 1 (15.9 mg, 12.8 µmoles) in DMF (800 µl) and DIEA (100 µl). 100 µl of the solution was added every 15 minutes while stirring. Following the completion of the addition of 1, the reaction was stirred for 2 hours. The reaction was diluted with 0.1% TFA (15 ml) and the reaction was purified by reversed phase HPLC. ImImPyPy-(R)$^{Glu-NHS}$γ-ImPyPyPy-β-Dp was recovered as a white powder upon lyophilization of the appropriate fraction (8.8 mg, 6.1 µmoles, 47.3% recovery). UV (H$_2$O) λ$_{max}$ (ε), 312 nm, (66, 600); $^1$H NMR (500 MHz, DMSO-d$_6$, 25 C): δ=10.320 (s, 1H), 10.242 (s, 1H), 10.097 (s, 1H), 9.930 (s, 2H), 9.872 (s, 1H), 9.740 (s, 1H), 9.23 (br s, 1H, CF$_3$COOH), 8.183 (d, 1H, J=8 Hz), 8.034 (t, 1H, J=5.5 Hz), 8.010 (t, 1H, J=5.5 Hz), 7.946 (t, 1H, J=5.3 Hz), 7.563 (s, 1H), 7.454 (s, 1H), 7.272 (s, 1H), 7.263 (s, 1H), 7.215 (s, 1H), 7.181 (s, 1H), 7.144 (m, 4H), 7.080 (s, 1H), 7,061 (s, 1H), 6.887 (s, 1H), 6.870 (s, 1H), 4.001 (s, 6H), 3.957 (s, 3H), 3.848 (s, 3H), 3.842 (s, 3H), 3.833 (s, 3H), 3.793 (s, 3H), 3.790 (s, 3H), 3.7–3.9 (br, m, 3H), 3.378 (q, 2H, J=5.5 Hz), 3.228 (m, 2H), 3.107 (q, 2H, J=6 Hz), 2.998 (m, 2H), 2.741 (s, 3H), 2.731 (s, 3H), 2.345 (t, 2H, J=7 Hz), 2.228 (m, 2H), 1.728 (m, 4H). MALDI-TOF-MS (monoisotopic) [M+H] 1449.63 (calculated 1449.62 for C$_{66}$H$_{81}$N$_{24}$O$_{15}$.)

ImImPyPy-(R)$^{(R)-CBI}$γ-ImPyPyPy-β-Dp (1R). To a solution of 1-NHS (6.9 mg, 4.75 µmoles) in dry DMF was added 47.5 µl of a 1 µM solution of DCC (10 equiv.) and 9.5 µl of a 0.5 M solution of N-hydroxysuccinimide (1 equiv.). The solution was stirred for 2 hours. Separately, a solution of 4S (2 mg, 1 equiv.) was deprotected with 3M HCl/ethyl acetate (5 ml) for 30 minutes under argon. The ethyl acetate was then removed by vacuum and then coevaporated twice from dichloromethane. The gray solid was then dissolved in 50 µl of dry DMF and then added to the polyamide solution. DIEA (8 µl, 10 equiv.) was then added and the reaction was stirred for 3 hours under argon. Upon completion, the reaction was diluted with 0.1% TFA (2 ml) and the reaction was purified by reversed phase HPLC. ImImPyPy-(R)$^{(R)-CBI}$γ-ImPyPyPy-β-Dp was recovered as a white powder upon lyophilization of the appropriate fraction (1.4 mg, 17.8% recovery). UV (H$_2$O) λ$_{max}$ (ε), 314 nm, (73, 854); $^1$H NMR (500 MHz, DMSO-d$_6$, 25 C): δ=10.342 (s, 1H), 10.316 (s, 1H), 10.248 (s, 1H), 10.096 (s, 1H), 9.928 (s, 2H), 9.869 (s, 1H), 9.691 (s, 1H), 9.17 (br s, 1H, CF$_3$COOH), 8.172 (d, 1H, J=7.5 Hz), 8.063 (d, 1H, J=8 Hz) 8.029 (t, 1H, J=6 Hz), 8.008 (t, 1H, J=5.5 Hz), 7.962 (m, 2H), 7.894 (t, 1H, J=5.5 Hz), 7.747 (d, 1H, J=8 Hz), 7.556 (s, 1H), 7.464 (t, 1H, J=7.5 Hz), 7.449 (s, 2H), 7.299 (t, 1H, J=7), 7.267 (s, 1H), 7.254 (s, 1H), 7.206 (s, 1H), 7.172 (s, 1H), 7.145 (m, 3H), 7.059 (s, 2H), 6.892 (s, 1H), 6.870 (s, 1H), 4.526 (q, 1H. J=7 Hz), 4.287 (t, 1H, J=10.5 Hz), 4.111 (m, 2H), 3.998 (s, 6H), 3.948 (s, 3H), 3.844 (s, 3H), 3.837 (s, 3H), 3.831 (s, 3H), 3.791 (s, 3H), 3.787 (s, 3H), 3.106 (q, 2H, J=6.5 Hz), 3.004 (m, 4H), 2.739 (s, 3H), 2.729 (s, 3H), 2.343 (t, 2H, J=7.3 Hz), 2.181 (t, 2H, J=7 Hz), 2.098 (t, 2H, J=7.8 Hz), 1.981 (m, 2H), 1.741 (m, 4H), 1.631 (m, 2H), 1.540 (m, 1H). MALDI-TOF-MS (monoisotopic) [M+H] 1638.72 (calculated 1638.69 for C$_{78}$H$_{93}$N$_{25}$O$_{14}$).

ImImPyPy-(R)$^{(S)-CBI}$γ-ImPyPyPy-β-Dp (1S). ImImPyPy-(R)$^{(S)-CBI}$γ-ImPyPyPy-β-Dp was prepared from 1-NHS as described for 1R. (1.4 mg, 30.4% recovery). UV (H$_2$O)λ$_{max}$ (ε), 314 nm, (73, 854); $^1$H NMR (DMSO-d$_6$): $^1$H NMR (500 MHz, DMSO-d$_6$, 25 C): δ=10.343 (s, 1H), 10.316 (s, 1H), 10.248 (s, 1H), 10.095 (s, 1H), 9.929 (s, 2H), 9.870 (s, 1H), 9.689 (s, 1H), 9.19 (brs, 1H, CF$_3$COOH), 8.173 (d, 1H J=7.5 Hz), 8.064 (d, 1H, J=8 Hz), 8.029 (m, 2H), δ=7.963 (m, 2H, C4-H), 7.895 (t, 1H, J=5.5 Hz), 7.747 (d, 1H, J=8 Hz), 7.556 (s, 1H), 7.464 (t, 1H, J=8 Hz), 7.451 (s, 1H), 7.445 (s, 1H), 7.299 (t, 1H, J=7.8 Hz), 7.266 (s, 1H), 7.255 (s, 1H), 7.206 (s, 1H), 7.175 (s, 1H), 7.145 (m, 3H), 7.060 (s, 2H), 6.891 (s, 1H), 6.870 (s, 1H), 4.525 (q, 1H, J=7 Hz), 4.285 (t, 1H, J=10.5 Hz), 4.111 (d, 2H, J=8.5 Hz), 3.998 (s, 6H), 3.951 (s, 3H), 3.844 (s, 3H), 3.837 (s, 3H), 3.831 (s, 3H), 3.792 (s, 3H), 3.787 (s, 3H), 3.105 (q, 2H, J=6 Hz), 3.000 (m, 4H), 2.737 (s, 3H), 2.729 (s, 3H), 2.343 (t, 2H, J=6.8 Hz), 2.180 (t, 2H, J=8 Hz), 2.099 (t, 2H, J=8 Hz), 1.997 (m, 2H), 1.727 (m, 2H), 1.631 (m, 2H), 1.540 (m, 1H). MALDI-TOF-MS (monoisotopic) [M+H] 1638.71 (calculated 1638.69 for C$_{78}$H$_{93}$N$_{25}$O$_{14}$.)

3-(tert-Butoxycarbonyl)-1-(chloromethyl)-5-hydroxy-1,2-dihydro-3H-benz[e]indole (seco-CBI-BOC, 3') was synthesized and enantiomers separated by already published protocols. Boger, D. L.; et al., *J. Org. Chem.* 1992, 57, 2873–2876. Boger, D. L., and McKie, J. A. *J. Org. Chem.* 1995, 60, 1271–1275. Boger, D. L.; et al., O. *J. Org. Chem.* 1990, 55, 5823–5832.

Seco-CBI-β-alanine-BOC (4'). Seco-CBI-BOC (85 mg, 0.255 mmoles) was deprotected in 3M HCl/ethyl acetate (10 ml) for 30 minutes under argon. After the ethyl acetate was removed by evaporation, and the deprotected seco-CBI was coevaporated twice from dichloromethane. BOC-β-alanine (96.4 mg, 2 equiv.) and EDC (293.3 mg, 6 equiv.) were added with DMF (5 ml). The solution was stirred overnight under argon. After the reaction was complete, 15 ml of water was added, and the reaction was extracted 6 times with ethyl ether. The ether was washed with brine, and dried with Na$_2$SO$_4$, and purified by flash chromatography (5% methanol/dichloromethane) to yield an off-white powder. (R)-Seco-CBI-β-alanine-BOC (4R): 90 mg, 86%, $^1$H NMR (300 MHz, CDCl$_3$, 25 C): δ=9.37 (s, 1H), 8.27 (m, 2H), 7.62 (d, 1H, J=8.1 Hz), 7.52 (t, 1H, J=6.6 Hz), 7.38 (t, 1H, J=7.5 Hz), 5.55 (br t, 1H), 4.19 (d, 1H, J=10.2 Hz), 4.06 (t, 1H, J=9.9 Hz), 3.93 (m, 2H), 3.62 (m, 2H), 3.38 (t, 1H, J=10.5

Hz), 2.75 (m, 2H), 1.44 (s, 9H). $[\alpha]^{29}_D=+25.8$ (c=0.1) (S)-Seco-CBI-β-alanine-BOC (4S): $^1$H NMR (300 MHz, CDCl$_3$, 25 C): δ=9.37 (s, 1H), 8.27 (m, 2H), 7.63 (d, 1H, J=8.1 Hz), 7.53 (t, 1H, J=6.6 Hz), 7.40 (t, 1H, J=7.5 Hz), 5.55 (br t, 1H), 4.21 (d, 1H, J=10.2 Hz), 4.06 (t, 1H, J=9.9 Hz), 3.96 (m, 2H), 3.64 (m, 2H), 3.40 (t, 1H, J=10.5 Hz), 2.75 (m, 2H), 1.44 (s, 9H). $[\alpha]^{29}_D=-29.4$ (c=0.1)

Seco-CBI-β-alanine-(dimethyl)-γ-amino butyric acid (2'). Seco-CBI-β-alanine-BOC (5 mg, 12.3 μmoles) was deprotected in 3M HCl/ethyl acetate (5 ml) for 30 minutes under argon. The ethyl acetate was removed by evaporation, and the deprotected seco-CBI-β-alanine was coevaporated twice from dichloromethane. Separately, a solution of (dimethyl)-γ-aminobutyric acid (4.1 mg, 2 equiv.) in DMF (200 μl) was stirred in a flame dried flask with DCC (25.4 mg, 10 equiv) and N-hydroxysuccinimide (1.4 mg, 1 equiv) for 1 hour under argon. This was added to the deprotected seco-CBI-β-alanine and DIEA (7 μl, 3 equiv.) was added. The solution was stirred for 1 hour under argon, and purified by reversed phase HPLC. Seco-CBI-β-alanine-(dimethyl)-β-aminobutyric acid was recovered as a white powder upon lyophilization of the appropriate fraction. (R)-Seco-CBI-β-alanine-(dimethyl)-β-aminobutyric acid (2R): 2.5 mg, 48% (recovery) $^1$H NMR (300 MHz, CD$_3$CN, 25 C): δ=10.9 (br s, 1H), 8.12 (d, 1H, J=7.5 Hz), 8.02 (s, 1H), 7.69 (d, 1H, J=8.4 Hz), 7.48 (t, 1H, J=8.4 Hz), 7.33 (t, 1H, J=6.9 Hz), 7.09 (br s, 1H), 4.15 (m, 2H), 3.93 (d, 3H), 3.63 (t, 2H), 3.51 (m, 2H), 3.04 (m, 4H), 2.71 (s, 6H), Electrospray MS [M+H]: 418.2 (Calculated 418.2 for $C_{22}H_{29}ClN_3O_3$) (S)-Seco-CBI-β-alanine-(dimethyl)-γ-aminobutyric acid (2S): 3.4 mg, 66% (recovery). $^1$H NMR (300 MHz, CD$_3$CN, 25 C): δ=10.9 (br s, 1H), 8.13 (d, 1H, J=8.1 Hz), 8.00(s, 1H), 7.74(d, 1H, J=8.4 Hz), 7.50(t, 1H, J=7.5 Hz), 7.34 (t, 1H, J=7.5 Hz), 7.00 (br s, 1H), 4.23 (m, 2H). 4.20 (m, 1H), 3.93 (d, 2H), 3.67 (t, 2H), 3.51 (m, 2H), 3.04 (t, 2H), 2.75 (s, 6H). Electrospray MS [M+H]: 418.2 (Calculated 418.2 for $C_{22}H_{29}ClN_3O_3$)

Example 7

Construction of Plasmid DNA

The plasmid pAC1 was constructed using previously described methods. Fluorescent sequencing was performed at the DNA Sequencing Facility at the California Institute of Technology and was used to verify the presence of the desired insert. Concentration of the prepared plasmid was determined at 260 nm from the relationship of 1 OD unit=50 μg mL$^{-1}$ duplex DNA.

Example 8

PCR Labeling to Generate 5'-End-Labeled Restriction Fragments

Two 21 mer primers were synthesized for PCR amplification: primer A (labeled) 5'-AATTCGAGCTCGGTACCCGGG-3' (SEQ ID NO:24) and primer B (unlabeled) 5'-CTGGCACGACAGGTTTCCCGA-3' (SEQ ID NO:25). Primer A was treated with T4 polynucleotide kinase and deoxyadenosine 5'-[γ-$^{32}$P] triphosphate as previously described. PCR reactions containing 60 pmol each primer, 10 μl PCR buffer (Boehringer-Mannheim), 3.7 μl template (0.003 μg/mL), 2 μl dNTP mix (each at 10 mM), 1 μl 100×BSA (New England Biolabs) and 83 μl water were heated at 70 C. for 5 minutes. Four units of Taq Polymerase were added (Boehringer-Mannheim). Thirty amplification cycles were performed, each cycle consisting of the following segments:, 94° C. for 1 min, 54° C. for 1 minute, and 72° C. for 1.5 minutes. Following the last cycle, 10 minutes of extension at 72° C. completed the reaction. The PCR products were gel purified as previously reported for 3'-end labeling protocols.

Example 9

Cleavage Reactions

All reactions were carried out in a volume of 50 μl. A polyamide or seco-CBI-dimethyl gaba stock solution or water (for reference lane) was added to an assay buffer of TE (pH7.5) and 20 kcpm of 3'- or 5'-radiolabeled DNA. The solutions were allowed to equilibrate for 12 hours or the appropriate time (for time course reactions) at 37° C. The reactions were stopped with 60 μl of a solution containing NaOAc (600 mM), EDTA pH 8.0 (12.5 mM), calf thymus DNA (150 μM base pair), glycogen (0.8 mg mL$^{-1}$), and NaCl (2 M). Ethanol was added to remove unbound polyamide and precipitate the products. The reactions were resuspended in 20 μl of TE (pH 7.5) and cleavage was initiated by heating at 95° C. for 30 minutes. The cleavage products were precipitated with 150 μl ethanol and then resuspended in 100 mM trisborate-EDTA/80% formamide loading buffer, and denatured and loaded onto polyacrylamide gels as previously reported. The gels were quantitated by the use of storage phosphor technology. Yield or efficiency of alkylation was determined as the ratio between the volume integration assigned to the products and the sum of the volumes of all the products in the lane.

One skilled in the art will readily appreciate that the present invention is well adapted to carry out the objects and obtain the ends and advantages mentioned, as well as those inherent, therein. The compounds, methods, treatments, procedures, and applications described herein are presently representative of preferred embodiments, and are exemplary and not intended as limitations on the scope of the invention. Changes, modifications, and alternatives therein and other uses will occur to those skilled in the art upon review of the above description, which changes are encompassed within the spirit of the invention and the appended claims.

The invention illustratively described herein suitably may be practiced in the absence of any element or elements, or limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

All patents, patent applications, and other publications and references mentioned in the specification are hereby incorporated by reference in their entirety, and are indicative of the levels of those skilled in the art to which the invention pertains.

What is claimed is:

1. A polyamide-alkylator conjugate comprising an alkylator linked to a polyamide, wherein said polyamide comprises at least one pyrrole or imidazole amino acid and wherein (a) said polyamide comprises a γ-aminobutyric acid and said alkylator is linked to said γ-aminobutyric acid, (b) said alkylator selectively alkylates only one strand of a double-stranded DNA, or (c) said polyamide binds DNA with subnanomolar binding affinity.

2. The conjugate of claim 1, wherein said alkylator is linked to said γ-aminobutyric acid of said polyamide.

3. The conjugate of claim 2, wherein said alkylator is covalently linked to said γ-aminobutyric acid of said polyamide.

4. The conjugate of claim 1, wherein said alkylator selectively alkylates only one strand of a double-stranded DNA.

5. The conjugate of claim 4, wherein said polyamide portion of said conjugate interacts with said DNA.

6. The conjugate of claim 1, wherein said polyamide binds DNA with subnanomolar binding affinity.

7. The conjugate of claim 1, wherein said alkylator is reactive with DNA at about 37 degrees celsius.

8. The conjugate of claim 1, wherein said alkylator is substantially inert in aqueous media.

9. The conjugate of claim 1, wherein said conjugate is present in a buffer and said alkylator is non-reactive with said buffer.

10. The conjugate of claim 1, wherein said alkylator is a nitrogen mustard.

11. The conjugate of claim 1, wherein said alkylator is a derivative of chlorambucil.

12. The conjugate of claim 9, wherein said derivative is a bis(dichloroethylamino)benzene derivative.

13. The conjugate of claim 1, wherein said alkylator is seco-CBI.

14. The conjugate of claim 1, wherein said alkylator mitomycin or (+)-CC-1065.

15. The conjugate of claim 1, wherein said alkylator is covalently attached to an amino group on chiral $\chi$-carbon of said $\alpha$-aminobutyric acid of said polyamide.

16. The conjugate of claim 1, wherein said polyamide is a hairpin polyamide.

17. The conjugate of claim 16, wherein said hairpin polyamide comprises eight heterocyclic rings, wherein each of said heterocylic rings is a pyrrole ring or an imidazole ring.

18. The conjugate of claim 1, wherein said conjugate is capable of sequence specific alkylation of said DNA.

19. The conjugate of claim 18, wherein said DNA is in the minor groove.

20. The conjugate of claim 18, wherein said conjugate alkylates an adenine adjacent to the binding site.

21. The conjugate of claim 1, wherein said conjugate has sub-nanomolar binding affinity for said DNA.

22. The conjugate of claim 1, wherein said conjugate has at least 20-fold greater affinity for a target site than for a site differing from said target site by base pairs.

23. The conjugate of claim 19, said conjugate has about 100-fold greater affinity for a target site than for a site differing from said target site by two base pairs.

24. The conjugate of claim 1, wherein said conjugate alkylates said DNA at a rate whereby alkylation is at least half completed at one or more match sites in about 2.2 hours.

25. The conjugate of claim 1, wherein said conjugate alkylates said DNA at a rate whereby final cleavage yield on the bottom strand of said DNA is at least about 45%.

26. The conjugate of claim 1, wherein said conjugate alkylates said DNA at a rate whereby final cleavage yield on the bottom strand of said DNA is at least about 96%.

27. The conjugate of claim 1, wherein said conjugate comprises separate domains for DNA binding and DNA covalent attachment.

28. The conjugate of claim 1, wherein said conjugate has substantially the same binding affinity and specificity as said polyamide.

29. A composition comprising the conjugate of claim 1 in a pharmaceutically acceptable carrier.

30. A method of making the conjugate of claim 1, comprising the steps of coupling said alkylator to said polyamide under conditions whereby said polyamide links to said alkylator and forms said polyamide-alkylator conjugate.

31. A method of making the composition of claim 29 comprising the step of providing the conjugate of claim 1 in a pharmaceutically acceptable carrier.

* * * * *

SEQUENCE LISTING

<160> NUMBER OF SEQ ID NOS: 25

<210> SEQ ID NO 1
<211> LENGTH: 12
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 1
agctgcttat at                                                         12

<210> SEQ ID NO 2
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 2
aaaagcagct gcttatatgc agcatct                                         27

<210> SEQ ID NO 3
<211> LENGTH: 13
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 3
ggatgcagct ctc                                                        13

<210> SEQ ID NO 4
<211> LENGTH: 29
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 4
cagctgctta tatgcagcat atgctgctc                                       29

<210> SEQ ID NO 5
<211> LENGTH: 59
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 5
cagctgctta tatgcagcat ccctgtagaa agcttatgtc agcagtcttg atgcagctc      59

<210> SEQ ID NO 6
<211> LENGTH: 241
<212> TYPE: DNA
<213> ORGANISM: Artificial Sequence

```
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 6
aattcgagct cggtacccgg taaccagaga gacccagtac aggcaaaaag cagctgctta    60
tatgcagcat ctgagggacg ccactcccca gtcccgcccc aggccacgcc tccctggaaa   120
gtccccagcg gaaagtccct tgtagaaagc tcgatgtcag cagtctttgt agtactccgg   180
tgcagctctc gggccacgtg ctgaaatgct aggcggctgt caatcgacct gcaggcatgc   240
a                                                                   241

<210> SEQ ID NO 7
<211> LENGTH: 13
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 7
agcagctgct tat                                                       13

<210> SEQ ID NO 8
<211> LENGTH: 11
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 8
tatgcagcat c                                                         11

<210> SEQ ID NO 9
<211> LENGTH: 11
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 9
cttgtagaaa g                                                         11

<210> SEQ ID NO 10
<211> LENGTH: 11
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 10
tcagcagtct t                                                         11

<210> SEQ ID NO 11
<211> LENGTH: 10
<212> TYPE: DNA
<213> ORGANISM: Artificial Sequence
<220> FEATURE:
```

```
<221> NAME/KEY: misc_feature
<223> OTHER INFORMATION: Description of Artificial Sequence:
      Polyamide-Alkylator Conjugate Target Sequence

<400> SEQUENCE: 11
gatgcagctc                                                           10

<210> SEQ ID NO 12
<211> LENGTH: 22
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 12
agcagctgct tatatgcagc at                                             22

<210> SEQ ID NO 13
<211> LENGTH: 22
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence
<221> NAME/KEY: misc_feature
<222> LOCATION: (2)..(2)
<223> OTHER INFORMATION: n represents i at the site of inosine
      substitution

<400> SEQUENCE: 13
ancagctgct tatatgcagc at                                             22

<210> SEQ ID NO 14
<211> LENGTH: 13
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence
<221> NAME/KEY: misc_feature
<222> LOCATION: (3)..(3)
<223> OTHER INFORMATION: n represents X at the site of inosine
      substitution

<400> SEQUENCE: 14
aancagctgc tta                                                       13

<210> SEQ ID NO 15
<211> LENGTH: 23
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 15
aagcagctgc ttatatgcag cat                                            23

<210> SEQ ID NO 16
<211> LENGTH: 10
<212> TYPE: DNA
<213> ORGANISM: Artificial Sequence
<220> FEATURE:
<221> NAME/KEY: misc_feature
```

```
<223> OTHER INFORMATION: Description of Artificial Sequence:
      Polyamide-Alkylator Conjugate Target Sequence

<400> SEQUENCE: 16
atggtcatag                                                                10

<210> SEQ ID NO 17
<211> LENGTH: 81
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 17
gtacttttcc aggcggaagg agtattttc caggcggaag gaggactttt ccaggagctt        60
ggcgtaatca tggtcatagc t                                                  81

<210> SEQ ID NO 18
<211> LENGTH: 65
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 18
aaggagtatt tttccaggcg gaaggaggac ttttccagga gcttggcgta atcatggtca        60
tagct                                                                    65

<210> SEQ ID NO 19
<211> LENGTH: 81
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII restriction fragment

<400> SEQUENCE: 19
gtacttttcc aggcggaagg agtattttc caggcggaag gaggactttt ccaggagctt        60
ggcgtaatca tggtcatagc t                                                  81

<210> SEQ ID NO 20
<211> LENGTH: 10
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 20
tcgtcgacga                                                                10

<210> SEQ ID NO 21
<211> LENGTH: 10
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence
```

```
<400> SEQUENCE: 21
agcagctgct                                                                  10

<210> SEQ ID NO 22
<211> LENGTH: 10
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence
<221> NAME/KEY: misc_feature
<222> LOCATION: (2)..(2)
<223> OTHER INFORMATION: n reperesents i at the site of inosine
      substitution

<400> SEQUENCE: 22 ancagctgct                                                                  10

<210> SEQ ID NO 23
<211> LENGTH: 11
<212> TYPE: DNA
<213> ORGANISM: Artificial Sequence
<220> FEATURE:
<221> NAME/KEY: misc_feature
<223> OTHER INFORMATION: Description of Artificial Sequence:
      Polyamide-Alkylator Conjugate Target Sequence

<400> SEQUENCE: 23
atggtcatag c                                                                11

<210> SEQ ID NO 24
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII primer A restriction fragment

<400> SEQUENCE: 24
aattcgagct cggtacccgg g                                                     21

<210> SEQ ID NO 25
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence:
      pHIV-LTR EcoRI/HindIII primer B restriction fragment

<400> SEQUENCE: 25
ctggcacgac aggtttcccg a                                                     21
```